(12) United States Patent
Swantner et al.

(10) Patent No.: US 10,512,721 B2
(45) Date of Patent: *Dec. 24, 2019

(54) SYSTEM AND METHOD FOR SYRINGE PLUNGER ENGAGEMENT WITH AN INJECTOR

(71) Applicant: BAYER HEALTHCARE LLC, Whippany, NJ (US)

(72) Inventors: Michael J. Swantner, Saxonburg, PA (US); Richard A. Seman, Delmont, PA (US); Barry L. Tucker, Verona, PA (US); Arthur E. Uber, III, Pittsburgh, PA (US); Kevin P. Cowan, Allison Park, PA (US); James A. Dedig, Pittsburgh, PA (US); Christopher D. Capone, Pittsburgh, PA (US); Jaroslaw Wlodarczyk, Lower Burrell, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 278 days.

This patent is subject to a terminal disclaimer.

(21) Appl. No.: 15/334,644

(22) Filed: Oct. 26, 2016

(65) Prior Publication Data
US 2017/0119963 A1    May 4, 2017

Related U.S. Application Data

(63) Continuation of application No. 14/925,722, filed on Oct. 28, 2015, now Pat. No. 9,480,797.

(51) Int. Cl.
*A61M 5/145* (2006.01)
*A61M 5/315* (2006.01)

(52) U.S. Cl.
CPC .... *A61M 5/14566* (2013.01); *A61M 5/31515* (2013.01); *A61M 5/14546* (2013.01); *A61M 2005/14573* (2013.01)

(58) Field of Classification Search
CPC .......... A61M 5/31511; A61M 5/31513; A61M 5/31515; A61M 5/5066; A61M 5/14566
See application file for complete search history.

(56) References Cited

U.S. PATENT DOCUMENTS 1,265,537 A    5/1918 Ivan
1,687,323 A    10/1928 Cook
(Continued)

FOREIGN PATENT DOCUMENTS

AU    317487    1/2008
DE    2919978 A1    11/1980
(Continued)

OTHER PUBLICATIONS

Non-Final Office Action dated May 6, 2013 in related case U.S. Appl. No. 12/710,293.
(Continued)

*Primary Examiner* — Laura A Bouchelle
(74) *Attorney, Agent, or Firm* — Joseph L. Kent; David Schramm; James R. Stevenson

(57) ABSTRACT

A plunger for use with a syringe has a plunger body with a proximal end, a distal end, and a circumferential sidewall extending between the proximal end and the distal end along a plunger longitudinal axis. The plunger further has at least one resiliently deflectable retaining member having a first segment attached to the plunger body and a second segment protruding toward the distal end of the plunger body and deflectable relative to the first segment. The plunger further has at least one actuation member associated with the at least one resiliently deflectable retaining member. The at least one actuation member interacts with a piston to deflect the at least one resiliently deflectable retaining member upon rotation of the plunger relative to the piston. The plunger is
(Continued)

engagable with the piston regardless of a rotational orientation of the piston relative to the plunger.

19 Claims, 54 Drawing Sheets

(56) References Cited

U.S. PATENT DOCUMENTS

| | | |
|---|---|---|
| 1,988,480 A | 1/1935 | Campkin |
| 2,392,196 A | 1/1946 | Smith |
| 2,419,401 A | 4/1947 | Hinds |
| 2,702,547 A | 2/1955 | Glass |
| 2,842,126 A | 7/1958 | Brown |
| 3,051,173 A | 8/1962 | Johnson et al. |
| D203,730 S | 2/1966 | Coanda |
| 3,270,483 A | 9/1966 | Smoyer et al. |
| 3,348,545 A | 10/1967 | Sarnoff et al. |
| 3,468,471 A | 9/1969 | Frtiz |
| 3,604,417 A | 9/1971 | Stolzenberg |
| 3,623,474 A | 11/1971 | Marlin et al. |
| 3,645,262 A | 2/1972 | Harrigan |
| 3,701,345 A | 10/1972 | Heilman et al. |
| 3,705,582 A | 12/1972 | Stumpf et al. |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,809,082 A | 5/1974 | Hurschman |
| 3,812,843 A | 5/1974 | Wootten et al. |
| 3,902,491 A | 9/1975 | Lajus |
| 3,964,139 A | 6/1976 | Kleinmann et al. |
| 3,987,940 A | 10/1976 | Tischlinger |
| 3,998,224 A | 12/1976 | Chiquiar-Arias |
| 4,006,736 A | 2/1977 | Kranys et al. |
| 4,030,498 A | 6/1977 | Tompkins |
| 4,080,967 A | 3/1978 | O'Leary |
| 4,148,316 A | 4/1979 | Xanthopoulos |
| 4,155,490 A | 5/1979 | Glenn |
| 4,159,713 A | 7/1979 | Prais |
| 4,180,006 A | 12/1979 | Ross |
| 4,180,069 A | 12/1979 | Walters |
| 4,226,236 A | 10/1980 | Genese |
| 4,252,118 A | 2/1981 | Richard et al. |
| 4,278,086 A | 7/1981 | Hodgins et al. |
| 4,303,070 A | 12/1981 | Ichikawa et al. |
| 4,345,595 A | 8/1982 | Whitney et al. |
| 4,351,335 A | 9/1982 | Whitney et al. |
| 4,356,822 A | 11/1982 | Winstead-Hall |
| 4,424,720 A | 1/1984 | Bucchianeri |
| 4,452,251 A | 6/1984 | Heilman |
| 4,453,934 A | 6/1984 | Gahwiler et al. |
| 4,464,265 A | 8/1984 | Joyner |
| 4,465,472 A | 8/1984 | Urbaniak |
| 4,465,473 A | 8/1984 | Rueegg |
| 4,475,666 A | 10/1984 | Bilbrey et al. |
| 4,476,381 A | 10/1984 | Rubin |
| 4,490,256 A | 12/1984 | Nussbaumer et al. |
| 4,493,646 A | 1/1985 | Lacour et al. |
| 4,500,310 A | 2/1985 | Christinger |
| 4,529,401 A | 7/1985 | Leslie et al. |
| 4,562,844 A | 1/1986 | Carpenter et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,628,969 A | 12/1986 | Jurgens, Jr. et al. |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,677,981 A | 7/1987 | Coursant |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,718,463 A | 1/1988 | Jurgens, Jr. et al. |
| 4,722,734 A | 2/1988 | Kolln |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,852,768 A | 8/1989 | Bartsch |
| 4,853,521 A | 8/1989 | Claeys et al. |
| 4,854,324 A | 8/1989 | Hirschman et al. |
| 4,863,427 A | 9/1989 | Cocchi |
| 4,869,720 A | 9/1989 | Chernack |
| 4,878,896 A | 11/1989 | Garrison et al. |
| 4,908,022 A | 3/1990 | Haber |
| 4,911,695 A | 3/1990 | Lindner |
| 4,923,443 A | 5/1990 | Greenwood |
| 4,929,238 A | 5/1990 | Baum |
| 4,931,043 A | 6/1990 | Ray et al. |
| 4,932,941 A | 6/1990 | Min et al. |
| 4,936,833 A | 6/1990 | Sams |
| 4,943,279 A | 7/1990 | Samiotes et al. |
| 4,950,243 A | 8/1990 | Estruch |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur, III |
| 4,988,337 A | 1/1991 | Ito |
| 4,997,423 A | 3/1991 | Okuda et al. |
| 5,000,735 A | 3/1991 | Whelan |
| 5,007,904 A | 4/1991 | Densmore et al. |
| 5,019,045 A | 5/1991 | Lee |
| 5,024,663 A | 6/1991 | Yum |
| 5,033,650 A | 7/1991 | Colin et al. |
| 5,034,004 A | 7/1991 | Crankshaw |
| 5,047,014 A | 9/1991 | Mosebach et al. |
| 5,059,179 A | 10/1991 | Quatrochi et al. |
| 5,062,832 A | 11/1991 | Seghi |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,090,962 A | 2/1992 | Landry, Jr. et al. |
| 5,093,079 A | 3/1992 | Bakaitis et al. |
| 5,094,148 A | 3/1992 | Haber et al. |
| 5,104,374 A | 4/1992 | Bishko et al. |
| 5,106,372 A | 4/1992 | Ranford |
| 5,106,379 A | 4/1992 | Leap |
| 5,122,118 A | 6/1992 | Haber et al. |
| 5,135,507 A | 8/1992 | Haber et al. |
| 5,147,311 A | 9/1992 | Pickhard |
| 5,153,827 A | 10/1992 | Coutre |
| 5,176,642 A | 1/1993 | Clement |
| 5,181,912 A | 1/1993 | Hammett |
| 5,226,897 A | 7/1993 | Nevens et al. |
| 5,236,416 A | 8/1993 | McDaniel et al. |
| 5,242,408 A | 9/1993 | Jhuboo et al. |
| 5,246,423 A | 9/1993 | Farkas |
| 5,254,086 A | 10/1993 | Palmer et al. |
| 5,254,101 A | 10/1993 | Trombley, III |
| 5,256,154 A | 10/1993 | Liebert et al. |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,282,858 A | 2/1994 | Bisch et al. |
| 5,300,031 A | 4/1994 | Neer et al. |
| 5,308,330 A | 5/1994 | Grimard |
| 5,314,415 A | 5/1994 | Liebert et al. |

(56) References Cited

U.S. PATENT DOCUMENTS

| | | |
|---|---|---|
| 5,317,506 A | 5/1994 | Coutre et al. |
| 5,324,273 A | 6/1994 | Discko, Jr. |
| 5,336,189 A | 8/1994 | Sealfon |
| 5,338,309 A | 8/1994 | Imbert |
| 5,342,298 A | 8/1994 | Michaels et al. |
| 5,353,691 A | 10/1994 | Haber et al. |
| 5,354,287 A | 10/1994 | Wacks |
| 5,356,375 A | 10/1994 | Higley |
| 5,356,393 A | 10/1994 | Haber et al. |
| 5,373,684 A | 12/1994 | Vacca |
| 5,380,285 A | 1/1995 | Jenson |
| 5,383,858 A | 1/1995 | Reilly et al. |
| 5,389,075 A | 2/1995 | Vladimirsky |
| 5,397,313 A | 3/1995 | Gross |
| 5,411,488 A | 5/1995 | Pagay et al. |
| 5,413,563 A | 5/1995 | Basile et al. |
| 5,425,716 A | 6/1995 | Kawasaki et al. |
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| 5,478,314 A | 12/1995 | Malenchek |
| 5,484,413 A | 1/1996 | Gevorgian |
| 5,512,054 A | 4/1996 | Morningstar |
| 5,520,653 A | 5/1996 | Reilly et al. |
| 5,531,698 A | 7/1996 | Olsen |
| 5,531,710 A | 7/1996 | Dang et al. |
| 5,533,981 A | 7/1996 | Mandro et al. |
| 5,535,746 A | 7/1996 | Hoover et al. |
| 5,540,660 A | 7/1996 | Jenson |
| 5,545,140 A | 8/1996 | Conero et al. |
| 5,573,515 A | 11/1996 | Wilson et al. |
| 5,593,386 A | 1/1997 | Helldin |
| 5,624,408 A | 4/1997 | Helldin |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,688,252 A | 11/1997 | Matsuda et al. |
| 5,695,477 A | 12/1997 | Sfikas |
| 5,722,951 A | 3/1998 | Marano |
| 5,735,825 A | 4/1998 | Stevens et al. |
| 5,738,655 A | 4/1998 | Vallelunga et al. |
| 5,738,659 A | 4/1998 | Neer et al. |
| 5,741,227 A | 4/1998 | Sealfon |
| 5,741,232 A | 4/1998 | Reilly et al. |
| 5,779,675 A | 7/1998 | Reilly et al. |
| 5,782,803 A | 7/1998 | Jentzen |
| 5,785,682 A | 7/1998 | Grabenkort |
| 5,795,333 A | 8/1998 | Reilly et al. |
| 5,807,334 A | 9/1998 | Hodosh et al. |
| 5,808,203 A | 9/1998 | Nolan, Jr. et al. |
| 5,827,219 A | 10/1998 | Uber, III et al. |
| 5,827,262 A | 10/1998 | Neftel et al. |
| 5,840,026 A | 11/1998 | Uber, III et al. |
| RE35,979 E | 12/1998 | Reilly et al. |
| 5,865,805 A | 2/1999 | Ziemba |
| 5,873,861 A | 2/1999 | Hitchins et al. |
| 5,879,336 A | 3/1999 | Brinon |
| 5,882,343 A | 3/1999 | Wilson et al. |
| 5,899,885 A | 5/1999 | Reilly et al. |
| 5,902,276 A | 5/1999 | Namey, Jr. |
| 5,913,844 A | 6/1999 | Ziemba et al. |
| 5,919,167 A | 7/1999 | Mulhauser et al. |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |
| 5,954,697 A | 9/1999 | Srisathapat et al. |
| 5,954,700 A | 9/1999 | Kovelman |
| 5,997,502 A | 12/1999 | Reilly et al. |
| 5,997,511 A | 12/1999 | Curie et al. |
| 6,004,300 A | 12/1999 | Butcher et al. |
| 6,017,330 A | 1/2000 | Hitchins et al. |
| 6,042,565 A | 3/2000 | Hirschman et al. |
| 6,048,334 A | 4/2000 | Hirschman et al. |
| 6,059,756 A | 5/2000 | Yeh |
| 6,080,136 A | 6/2000 | Trull et al. |
| 6,083,197 A | 7/2000 | Umbaugh |
| 6,083,200 A | 7/2000 | Grimm et al. |
| 6,090,064 A | 7/2000 | Reilly et al. |
| 6,099,502 A | 8/2000 | Duchon et al. |
| 6,129,712 A | 10/2000 | Sudo et al. |
| 6,162,200 A | 12/2000 | Sawa et al. |
| 6,196,999 B1 | 3/2001 | Goethel et al. |
| 6,221,045 B1 | 4/2001 | Duchon et al. |
| 6,224,577 B1 | 5/2001 | Dedola et al. |
| 6,267,749 B1 | 7/2001 | Miklos et al. |
| 6,315,758 B1 | 11/2001 | Neer et al. |
| 6,322,535 B1 | 11/2001 | Hitchins et al. |
| RE37,487 E | 12/2001 | Reilly et al. |
| 6,336,913 B1 | 1/2002 | Spohn et al. |
| 6,339,718 B1 | 1/2002 | Zatezalo et al. |
| 6,345,262 B1 | 2/2002 | Madden |
| 6,432,089 B1 * | 8/2002 | Kakimi ............ A61M 5/14546 604/218 |
| 6,447,487 B1 | 9/2002 | Cane' |
| 6,511,459 B1 | 1/2003 | Fago |
| 6,517,516 B1 | 2/2003 | Caizza |
| 6,533,758 B1 | 3/2003 | Staats et al. |
| 6,582,399 B1 | 6/2003 | Smith et al. |
| 6,585,700 B1 | 7/2003 | Trocki et al. |
| 6,652,489 B2 | 11/2003 | Trocki et al. |
| 6,659,979 B2 | 12/2003 | Neer et al. |
| 6,669,663 B1 | 12/2003 | Thompson |
| 6,733,477 B2 | 5/2004 | Cowan et al. |
| 6,733,478 B2 | 5/2004 | Reilly et al. |
| 6,752,789 B2 | 6/2004 | Duchon et al. |
| 6,764,466 B1 | 7/2004 | Staats et al. |
| 6,808,513 B2 | 10/2004 | Reilly et al. |
| 6,817,990 B2 | 11/2004 | Yap et al. |
| 6,958,053 B1 | 10/2005 | Reilly |
| 7,018,363 B2 | 3/2006 | Cowan et al. |
| 7,029,459 B2 | 4/2006 | Reilly |
| 7,300,417 B1 | 11/2007 | Goethel et al. |
| 7,337,538 B2 | 3/2008 | Moutafis et al. |
| 7,399,293 B2 | 7/2008 | Oyibo et al. |
| 7,419,478 B1 | 9/2008 | Reilly et al. |
| 7,455,659 B2 | 11/2008 | Nemoto et al. |
| 7,462,166 B2 | 12/2008 | Kowan et al. |
| 7,465,290 B2 | 12/2008 | Reilly |
| 7,497,843 B1 | 3/2009 | Castillo et al. |
| 7,501,092 B2 | 3/2009 | Chen |
| 7,540,856 B2 | 6/2009 | Trocki et al. |
| 7,553,294 B2 | 6/2009 | Lazzaro et al. |
| 7,566,326 B2 | 7/2009 | Duchon et al. |
| 7,666,169 B2 | 2/2010 | Cowan et al. |
| 7,682,345 B2 | 3/2010 | Savage |
| 7,803,134 B2 | 9/2010 | Sharifi et al. |
| 7,972,306 B2 | 7/2011 | Shearn |
| 8,012,124 B1 | 9/2011 | Fago et al. |
| 8,012,125 B1 | 9/2011 | Fago et al. |
| 8,038,656 B2 * | 10/2011 | Lloyd ............... A61M 5/31515 604/218 |
| 8,070,732 B2 | 12/2011 | Rochette |
| 8,105,293 B2 | 1/2012 | Pickhard |
| 8,172,814 B2 | 5/2012 | Cane et al. |
| 8,177,757 B2 | 5/2012 | Nemoto et al. |
| 8,308,689 B2 | 11/2012 | Lewis |
| 8,353,879 B2 | 1/2013 | Goethel et al. |
| 8,475,415 B2 | 7/2013 | Schiller et al. |
| 8,480,631 B2 | 7/2013 | Wotton et al. |
| 8,585,658 B2 | 11/2013 | Forstreuter |
| 8,613,730 B2 | 12/2013 | Hieb et al. |
| 8,628,495 B2 | 1/2014 | Horton et al. |
| 8,721,596 B2 | 5/2014 | Trocki et al. |
| 8,740,854 B2 | 6/2014 | Schiller et al. |
| 8,740,856 B2 | 6/2014 | Quinn et al. |

(56) References Cited

U.S. PATENT DOCUMENTS

| | | |
|---|---|---|
| 8,845,596 B2 | 9/2014 | Berman et al. |
| 8,851,866 B2 | 10/2014 | Moutafis et al. |
| 8,857,674 B2 | 10/2014 | Nighy et al. |
| 8,864,712 B1 | 10/2014 | Fago et al. |
| 8,926,569 B2 | 1/2015 | Bisegna et al. |
| 8,932,255 B1 | 1/2015 | Fago et al. |
| 9,173,995 B1 | 11/2015 | Tucker et al. |
| 9,174,003 B2 | 11/2015 | Cowan et al. |
| 9,199,033 B1 | 12/2015 | Cowan et al. |
| 9,480,797 B1* | 11/2016 | Swantner .......... A61M 5/14566 |
| 9,736,635 B2 | 8/2017 | Quatrini |
| 9,844,622 B2 | 12/2017 | Savage et al. |
| 2001/0047153 A1 | 11/2001 | Trocki et al. |
| 2002/0022807 A1 | 2/2002 | Duchon et al. |
| 2002/0068905 A1 | 6/2002 | Cowan et al. |
| 2002/0128606 A1 | 9/2002 | Cowan et al. |
| 2002/0165491 A2 | 11/2002 | Reilly |
| 2002/0177811 A1 | 11/2002 | Reilly et al. |
| 2003/0004468 A1 | 1/2003 | Righi et al. |
| 2003/0009133 A1 | 1/2003 | Ramey |
| 2003/0060754 A1 | 3/2003 | Reilly et al. |
| 2003/0120219 A1 | 6/2003 | Nielsen et al. |
| 2003/0153877 A1 | 8/2003 | Huang et al. |
| 2003/0163089 A1 | 8/2003 | Bynum |
| 2003/0216683 A1 | 11/2003 | Shekalim |
| 2003/0236800 A1 | 12/2003 | Goeltzenleuchter et al. |
| 2004/0006314 A1 | 1/2004 | Campbell et al. |
| 2004/0039368 A1 | 2/2004 | Reilly et al. |
| 2004/0064041 A1 | 4/2004 | Lazzaro et al. |
| 2004/0068223 A1 | 4/2004 | Reilly |
| 2004/0074453 A1 | 4/2004 | Roelle et al. |
| 2004/0116861 A1 | 6/2004 | Trocki et al. |
| 2004/0133153 A1 | 7/2004 | Trocki et al. |
| 2004/0133161 A1 | 7/2004 | Trocki et al. |
| 2004/0133162 A1 | 7/2004 | Trocki et al. |
| 2004/0133183 A1 | 7/2004 | Trocki et al. |
| 2004/0158205 A1 | 8/2004 | Savage |
| 2004/0186437 A1 | 9/2004 | Frenette et al. |
| 2004/0243022 A1 | 12/2004 | Carney et al. |
| 2004/0243067 A1 | 12/2004 | Sibbitt |
| 2005/0015056 A1 | 1/2005 | Duchon et al. |
| 2005/0113754 A1 | 5/2005 | Cowan et al. |
| 2005/0240149 A1 | 10/2005 | Lu |
| 2006/0129104 A1 | 6/2006 | Cowan et al. |
| 2006/0173411 A1 | 8/2006 | Barere |
| 2007/0123830 A1 | 5/2007 | Johannes Fierkens, Sr. et al. |
| 2007/0191785 A1 | 8/2007 | Barere et al. |
| 2009/0247957 A1 | 10/2009 | Heutschi |
| 2010/0016796 A1 | 1/2010 | Derichs |
| 2010/0057014 A1 | 3/2010 | Cane et al. |
| 2010/0222674 A1 | 9/2010 | Cowan et al. |
| 2010/0318030 A1 | 12/2010 | Jenkins |
| 2011/0034882 A1 | 2/2011 | Quinn et al. |
| 2011/0178500 A1 | 7/2011 | Shang et al. |
| 2011/0224611 A1 | 9/2011 | Lum et al. |
| 2012/0039809 A1 | 2/2012 | Levinson et al. |
| 2012/0136298 A1* | 5/2012 | Bendix ............... A61M 5/2448 604/89 |
| 2012/0184920 A1 | 7/2012 | Okihara et al. |
| 2013/0211325 A1 | 8/2013 | Wang et al. |
| 2013/0317427 A1 | 11/2013 | Brereton et al. |
| 2013/0317480 A1 | 11/2013 | Reber et al. |
| 2013/0338605 A1 | 12/2013 | Chen |
| 2014/0027009 A1 | 1/2014 | Riley et al. |
| 2014/0031763 A1 | 1/2014 | Soma et al. |
| 2014/0094749 A1 | 4/2014 | Cowan et al. |
| 2014/0200483 A1 | 7/2014 | Fojtik |
| 2014/0243746 A1 | 8/2014 | Trocki et al. |
| 2014/0330216 A1 | 11/2014 | Weaver et al. |

FOREIGN PATENT DOCUMENTS

| | | |
|---|---|---|
| DE | 3227417 A1 | 2/1983 |
| DE | 4017920 A1 | 12/1991 |
| DE | 19601214 A1 | 8/1996 |
| DE | 19633530 A1 | 2/1998 |
| EP | 011724 A2 | 6/1984 |
| EP | 0160303 A2 | 11/1985 |
| EP | 0164904 A2 | 12/1985 |
| EP | 0308380 A2 | 3/1989 |
| EP | 0319275 A1 | 6/1989 |
| EP | 0320168 A1 | 6/1989 |
| EP | 0323321 A1 | 7/1989 |
| EP | 0346950 A2 | 12/1989 |
| EP | 0364010 A2 | 4/1990 |
| EP | 0384657 A1 | 8/1990 |
| EP | 0482677 A1 | 4/1992 |
| EP | 0523343 A1 | 1/1993 |
| EP | 0523434 A1 | 1/1993 |
| EP | 0567944 A1 | 11/1993 |
| EP | 0567945 A1 | 11/1993 |
| EP | 0584531 A2 | 3/1994 |
| EP | 0736306 A1 | 10/1996 |
| EP | 0749757 A2 | 12/1996 |
| EP | 0900573 A2 | 3/1999 |
| EP | 0919251 A2 | 6/1999 |
| EP | 0951306 A2 | 10/1999 |
| EP | 1002551 A2 | 5/2000 |
| EP | 1166807 A1 | 1/2002 |
| EP | 0951306 B1 | 7/2005 |
| EP | 1166807 B1 | 11/2005 |
| GB | 847914 A | 9/1960 |
| GB | 1380873 A | 1/1975 |
| GB | 2108852 A | 5/1983 |
| JP | S61500415 A | 3/1986 |
| JP | S6327770 A | 2/1988 |
| JP | S6368177 A | 3/1988 |
| JP | 2001029466 A | 2/2001 |
| JP | 4462798 B2 | 5/2010 |
| JP | D1398129 | 10/2010 |
| JP | D1398130 | 10/2010 |
| JP | D1400385 | 11/2010 |
| JP | D1400386 | 11/2010 |
| JP | D1400551 | 11/2010 |
| JP | D1400552 | 11/2010 |
| WO | 8002376 A1 | 11/1980 |
| WO | 8500292 A1 | 1/1985 |
| WO | 8502256 A1 | 5/1985 |
| WO | 8906145 A1 | 7/1989 |
| WO | 8909071 A1 | 10/1989 |
| WO | 8911310 A1 | 11/1989 |
| WO | 9001962 A1 | 3/1990 |
| WO | 9104759 A1 | 4/1991 |
| WO | 9221391 A1 | 12/1992 |
| WO | 9413336 A1 | 6/1994 |
| WO | 9425089 A1 | 11/1994 |
| WO | 9632975 A1 | 10/1996 |
| WO | 9707841 A2 | 3/1997 |
| WO | 9736635 A1 | 10/1997 |
| WO | 9820920 A2 | 5/1998 |
| WO | 9965548 A1 | 12/1999 |
| WO | 0137903 A2 | 5/2001 |
| WO | 0137905 A2 | 5/2001 |
| WO | 0204049 A1 | 1/2002 |
| WO | 03101527 A1 | 12/2003 |
| WO | 2004035289 A1 | 4/2004 |
| WO | 2005053771 A2 | 6/2005 |
| WO | 2007130061 A1 | 11/2007 |
| WO | 2010139793 A1 | 12/2010 |
| WO | 2012124028 A1 | 9/2012 |
| WO | 2012155035 A1 | 11/2012 |
| WO | 2014139913 A1 | 9/2014 |
| WO | 2015006430 A1 | 1/2015 |
| WO | 2016069711 A1 | 5/2016 |
| WO | 2016069714 A1 | 5/2016 |

OTHER PUBLICATIONS

"Extended European Search Report and Opinion from EP15823049", dated Feb. 1, 2017.

Brochure for "Angiomat 6000" of Liebel-Farsheim, 2111 E. Galbraith Road, Cincinnati, OH 45215, © 1987.

(56) References Cited

OTHER PUBLICATIONS

Brochure for "Angiomat CT" of Liebel-Farsheim, 2111 E. Galbraith Road, Cincinnati, OH 45215, © 1988.
Brochure for "Cordis Lymphography Injector," Cordis Corporation, Miami, FL 33137 (1972).
Brochure for "PercuPump 1A" of E-Z-Em, Inc, 717 Main Street, Westbury, NY 11590, © 1990.
Brochure for the "The First and Only True Injection System," Medrad Mark V System, Control No. 85106-00-BA-02, Nov. 1988.
Non-Final Office Action dated Mar. 28, 2013 in related case U.S. Appl. No. 12/728,869.
Feb. 23, 2015 ISR and WO from PCT/US2014/067435.
FOA mailed Mar. 28, 2013 from U.S. Appl. No. 12/728,869.
Injektron 82 MRT User Instructions, Version MR2, CE0535, Mediron GmbH(Mar. 10, 1999).
"International Preliminary Report of Patentability dated Jan. 12, 2016 from PCT/US2014/045923".
International Search Report & Written Opinion for International Application No. PCT/US2004/039225, ISA/US, dated May 12, 2006.
International Search Report for Counterpart PCT Application No. PCT/US00/32271.
International Search Report for International Application No. PCT/AU01/00830, dated Nov. 1, 2001.
International Search Report for International Application No. PCT/US03/17305, dated Oct. 21, 2003.
IPRP dated Jan. 12, 2016 from PCT/US2014/045923.
ISR dated Oct. 30, 2014 from PCT/US2014/045923.
ISR dated May 12, 2006 by PCT/US2004/039225.
ISR from PCT/US97/20122, dated Jun. 30, 1998.
Liebel-Flarsheim company—Angiomat 6000 Digital Injection System Operator's Manual, 600950 Rev 1 (1990); p. 3-6 to 3-8, 4-52 to 4-56.
Medrad Envision CT Injector Operation Manual, EOM 700E, 92401-T-123 Rev E, Copyright 1995.
Medrad Envision CT Injector Operation Manual, EOM 700E, 92401-T-123 Rev E, pp. 2-10 to 2-11 and pp. 2-30 to 2-35(Copyright 1995).
Medrad, Mark V/Mark V Plus Injector Operation Manual,KMP 805P Rev. B (1990); pp. 1-18 to 1-28, 3-7 to 3-13, 14-1 to 14-4.
Supplementary ESR from EP 01949108 dated Apr. 13, 2007.
Supplementary ESR from EP 01949108 dated Apr. 25, 2007.
Supplementary Partial European Search Report for EP 01949108 dated Apr. 13, 2007.
Supplementary Partial European Search Report for EP 01949108 dated Apr. 25, 2007.
The European Search Report dated Apr. 27, 2015 from corresponding EP Application No. EP14174725.
The International Preliminary Report on Patentability dated Apr. 9, 2015 from corresponding PCT Application No. PCT/US2013/061384.
International Search Report from corresponding PCT Application PCT/US2013/061384 dated Feb. 20, 2014.
"Supplementary European Search Report dated Apr. 14, 2016 from EP13842045".
U.S. Appl. No. 09/448,835, filed Nov. 24, 1999.
U.S. Appl. No. 09/731,108, filed Dec. 6, 2000.
U.S. Appl. No. 10/159,592, filed May 30, 2002.
U.S. Appl. No. 10/166,848, filed Jun. 10, 2002.
U.S. Appl. No. 10/174,631, filed Jun. 19, 2002.
U.S. Appl. No. 10/174,639, filed Jun. 19, 2002.
U.S. Appl. No. 10/287,167, filed Nov. 4, 2002.
U.S. Appl. No. 10/380,188, filed Mar. 10, 2003.
U.S. Appl. No. 10/606,157, filed Jun. 25, 2003.
U.S. Appl. No. 10/606,157, filed Nov. 25, 2003.
U.S. Appl. No. 10/619,137, filed Jul. 14, 2003.
U.S. Appl. No. 10/668,643, filed Sep. 23, 2003.
U.S. Appl. No. 10/668,673, filed Sep. 23, 2003.
U.S. Appl. No. 10/669,144, filed Sep. 23, 2003.
U.S. Appl. No. 10/669,148, filed Sep. 23, 2003.
U.S. Appl. No. 10/670,154, filed Sep. 23, 2003.
U.S. Appl. No. 10/722,370, filed Nov. 25, 2003.
WO dated Oct. 30, 2014 from PCT/US2014/045923.
"International Search Report and Written Opinion from PCT Application No. PCT/US2016/059245", dated Mar. 10, 2017.
"International Search Report and Written Opinion from PCT Application No. PCT/US2016/059246", dated Dec. 1, 2016.
"Extended European Search Report from EP Application No. EP16860850", dated Mar. 6, 2019.

* cited by examiner

SYSTEM AND METHOD FOR SYRINGE PLUNGER ENGAGEMENT WITH AN INJECTOR

CROSS REFERENCE TO RELATED APPLICATIONS

The present application is a continuation of U.S. Ser. No. 14/925,722, filed Oct. 28, 2015, the disclosure of which is incorporated in its entirety by this reference.

BACKGROUND OF THE DISCLOSURE

Field of the Disclosure

The present disclosure relates generally to a system including a front-loading or front-installing syringe for use with a fluid injector and, further, to a connection interface for securing a syringe plunger to a piston of the fluid injector and to a method for engaging and disengaging the syringe plunger to and from the piston of the fluid injector.

Description of Related Art

In many medical diagnostic and therapeutic procedures, a medical practitioner, such as a physician, injects a patient with one or more medical fluids. In recent years, a number of injector-actuated syringes and fluid injectors for pressurized injection of fluids, such as a contrast solution (often referred to simply as "contrast"), a flushing agent, such as saline, and other medical fluids have been developed for use in procedures such as angiography, computed tomography (CT), ultrasound, magnetic resonance imaging (MRI), nuclear medicine, positron emission tomography (PET), and other imaging procedures. In general, these fluid injectors are designed to deliver a preset amount of fluid at a preset flow rate.

Various connection interfaces have been developed to facilitate the engagement of a syringe plunger to and from a piston of the fluid injector. In some aspects, the syringe having a retention feature is inserted into a syringe port on the fluid injector by aligning the syringe with a corresponding locking feature provided on the fluid injector. Such alignment also aligns the plunger in the syringe with the piston on the fluid injector such that the piston can engage the plunger and drive the plunger through the syringe barrel to draw fluid into the syringe barrel or deliver fluid from the syringe barrel. In other aspects, upon initial engagement with the plunger, the piston may be rotated, in a clockwise or counter-clockwise direction, until the piston engages a catch on the plunger. In further aspects, the piston has one or more radially-extendable pins that engage a lip on the plunger.

Many of the existing connection interfaces have construction that requires a complex piston head with various sensor elements and active engagement structures. There is a need in the art for an improved connection interface that allows for a simpler and easier engagement and disengagement of the syringe plunger to and from the piston of the fluid injector. There is a further need in the art for reducing or eliminating the need for the operator to rotationally align the syringe with the fluid injector to allow for a proper engagement of the syringe plunger with the piston of the fluid injector. There is a further need in the art for reducing the angle of rotation through which the operator rotates the syringe to release the syringe plunger from the piston for removal of the syringe. While various syringe plunger connection interfaces and methods are known in the medical field, improved connection interfaces between the syringe plunger and the piston of the fluid injector and methods for engaging and disengaging the syringe plunger to and from the piston of the fluid injector continue to be in demand.

SUMMARY OF DISCLOSURE

In view of the disadvantages of the existing connection interfaces between a syringe plunger and a piston of a fluid injector, there is a need in the art for an improved connection interface between a syringe plunger and a piston of a fluid injector that overcomes the deficiencies of the prior art. There is an additional need for improved methods for engaging and disengaging a syringe plunger to and from a piston of a fluid injector to allow easy loading or removal of a syringe to and from a fluid injector.

In accordance with some aspects, plunger for use with a syringe may have a plunger body having a proximal end, a distal end, and a circumferential sidewall extending between the proximal end and the distal end along a plunger longitudinal axis. The plunger may have at least one resiliently deflectable retaining member having a first segment attached to the plunger body and a second segment protruding toward the distal end of the plunger body and deflectable relative to the first segment, and at least one actuation member associated with the at least one resiliently deflectable retaining member. The at least one actuation member may interact with a piston used to engage the plunger to deflect the at least one resiliently deflectable retaining member upon rotation of the plunger relative to the piston.

In accordance with other aspects, at least one alignment member may be associated with the plunger body or the at least one resiliently deflectable retaining member. The at least one alignment member may have an alignment surface for guiding the piston into self-orienting alignment with the plunger. The at least one alignment member may have a plurality of alignment members spaced apart around the plunger longitudinal axis. The plurality of alignment members may be spaced apart at equal radial intervals around the plunger longitudinal axis. The second segment of the at least one resiliently deflectable retaining member may be deflectable radially relative to the first segment away from the plunger longitudinal axis. The at least one resiliently deflectable retaining member may be linearly or curvilinearly contiguous between the first segment and the second segment. The second segment of the at least one resiliently deflectable retaining member may be angled toward the plunger longitudinal axis.

In accordance with other aspects, the at least one actuation member may be provided on a surface of the at least one resiliently deflectable retaining member. The at least one actuation member may be at the second segment of the at least one resiliently deflectable retaining member. The at least one actuation member may be angled relative to a plane defined by a body of the at least one resiliently deflectable retaining member. The at least one resiliently deflectable retaining member may have a plurality of resiliently deflectable retaining members spaced apart around the plunger longitudinal axis. The plurality of resiliently deflectable retaining members may be spaced apart at equal radial intervals around the plunger longitudinal axis. A terminal surface of the second segment of the at least one resiliently deflectable retaining member may engage a surface of the piston to releasably lock the plunger with the piston. The terminal surface may be linear. The terminal surface may be perpendicular or angled relative to a direction of the plunger longitudinal axis.

In accordance with other aspects, the plunger body may define an interior cavity with a conical-shaped portion at the distal end of the plunger body and a cylindrical-shaped portion at the proximal end of the plunger body. The first segment of the at least one resiliently deflectable member may be attached to an inner surface of the plunger body. The at least one resiliently deflectable retaining member may protrude from the inner surface of the plunger body into the interior cavity. A plunger cover may be disposed over at least a portion of an outer surface of the plunger body. The plunger cover may have a resilient seal disposed around at least a portion of a circumferential sidewall of the plunger cover. The resilient seal may have an inner surface at least partially seated in a groove in the circumferential sidewall of the plunger body and an outer surface adapted to slidably engage with a barrel of a syringe. The actuating member may be a cam member.

In accordance with other aspects, a plunger for use with a syringe may have a plunger body having a proximal end, a distal end, and a circumferential sidewall extending between the proximal end and the distal end along a plunger longitudinal axis. The plunger may have at least one resiliently deflectable retaining member having a first segment attached to the plunger body and a second end protruding toward the distal end of the plunger body and deflectable relative to the first segment and at least one alignment member associated with the plunger body or the at least one resiliently deflectable retaining member. The at least one alignment member may guide a piston into self-orienting alignment with the plunger during engagement of the plunger with the piston. The plunger may have at least one actuation member associated with the at least one resiliently deflectable retaining member. The at least one actuation member may interact with the piston to deflect the at least one resiliently deflectable retaining member upon rotation of the plunger relative to the piston during disengagement of the plunger from the piston. A terminal surface of the second segment of the at least one resiliently deflectable retaining member may engage a surface of the piston to releasably lock the plunger with the piston. The at least one actuation member may be at the second segment of the at least one resiliently deflectable retaining member. The second segment of the at least one resiliently deflectable retaining member may be deflectable radially relative to the first segment away from the plunger longitudinal axis.

In accordance with other aspects, a plunger for use with a syringe may have a plunger body having a proximal end, a distal end, and a circumferential sidewall extending between the proximal end and the distal end along a plunger longitudinal axis. The plunger may have at least one resiliently deflectable retaining member having a first segment attached to the plunger body and a second segment deflectable relative to the first segment, at least one alignment member associated with the plunger body or the at least one resiliently deflectable retaining member, and at least one actuation member associated with the at least one resiliently deflectable retaining member. The at least one alignment member may guide a piston into self-orienting alignment with the plunger during engagement of the plunger with the piston. The at least one actuation member may interact with the piston to deflect the at least one resiliently deflectable retaining member upon rotation of the plunger relative to the piston during disengagement of the plunger from the piston. The second segment of the at least one resiliently deflectable retaining member may protrude towards the distal end of the plunger body and wherein the second end of the at least one resiliently deflectable retaining member is deflectable radially relative to the first end away from the plunger longitudinal axis. The second end of the at least one resiliently deflectable retaining member may protrude in a direction circumferentially around the longitudinal axis of the plunger body and wherein the second end of the at least one resiliently deflectable retaining member is deflectable circumferentially relative to the first end.

In accordance with other aspects, a syringe may have a barrel having a barrel proximal end, a barrel distal end having a discharge nozzle, and a barrel sidewall extending between the barrel proximal end and the barrel distal end. The syringe may have a plunger slidably disposed within the barrel and reciprocally movable between the barrel proximal end and the barrel distal end. The plunger may have a plunger body having a proximal end, a distal end, and a circumferential sidewall extending between the proximal end and the distal end along a plunger longitudinal axis, at least one resiliently deflectable retaining member having a first segment attached to the plunger body and a second segment protruding toward the distal end of the plunger body and deflectable relative to the first segment, and at least one actuation member associated with the at least one resiliently deflectable retaining member. The at least one actuation member may interact with a piston used to engage the plunger to radially deflect the at least one resiliently deflectable retaining member upon rotation of the plunger relative to the piston.

Various aspects of the present disclosure may be further characterized by one or more of the following clauses:

Clause 1. A plunger for use with a syringe, the plunger comprising:

a plunger body having a proximal end, a distal end, and a circumferential sidewall extending between the proximal end and the distal end along a plunger longitudinal axis;

at least one resiliently deflectable retaining member having a first segment attached to the plunger body and a second segment protruding toward the distal end of the plunger body and deflectable relative to the first segment; and at least one actuation member associated with the at least one resiliently deflectable retaining member, wherein the at least one actuation member interacts with a piston used to engage the plunger to deflect the at least one resiliently deflectable retaining member upon rotation of the plunger relative to the piston.

Clause 2. The plunger according to clause 1, further comprising at least one alignment member associated with the plunger body or the at least one resiliently deflectable retaining member, the at least one alignment member having an alignment surface for guiding the piston into self-orienting alignment with the plunger.

Clause 3. The plunger according to clause 2, wherein the at least one alignment member comprises a plurality of alignment members spaced apart around the plunger longitudinal axis.

Clause 4. The plunger according to clause 3, wherein the plurality of alignment members is spaced apart at equal radial intervals around the plunger longitudinal axis.

Clause 5. The plunger according to any of clauses 1-4, wherein the second segment of the at least one resiliently deflectable retaining member is deflectable radially relative to the first segment away from the plunger longitudinal axis.

Clause 6. The plunger according to any of clauses 1-5, wherein the at least one resiliently deflectable retaining member is linearly or curvilinearly contiguous between the first segment and the second segment.

Clause 7. The plunger according to any of clauses 1-6, wherein the second segment of the at least one resiliently deflectable retaining member is angled toward the plunger longitudinal axis.

Clause 8. The plunger according to any of clauses 1-7, wherein the at least one actuation member is provided on a surface of the at least one resiliently deflectable retaining member.

Clause 9. The plunger according to clause 8, wherein the at least one actuation member is at the second segment of the at least one resiliently deflectable retaining member.

Clause 10. The plunger according to any of clauses 1-9, wherein the at least one actuation member is angled relative to a plane defined by a body of the at least one resiliently deflectable retaining member.

Clause 11. The plunger according to any of clauses 1-10, wherein the at least one resiliently deflectable retaining member comprises a plurality of resiliently deflectable retaining members spaced apart around the plunger longitudinal axis.

Clause 12. The plunger according to clause 11, wherein the plurality of resiliently deflectable retaining members is spaced apart at equal radial intervals around the plunger longitudinal axis.

Clause 13. The plunger according to any of clauses 1-12, wherein a terminal surface of the second segment of the at least one resiliently deflectable retaining member engages a surface of the piston to releasably lock the plunger with the piston.

Clause 14. The plunger according to clause 13, wherein the terminal surface is linear.

Clause 15. The plunger according to clause 13 or clause 14, wherein the terminal surface is perpendicular or angled relative to a direction of the plunger longitudinal axis.

Clause 16. The plunger according to any of clauses 1-15, wherein the plunger body defines an interior cavity with a conical-shaped portion at the distal end of the plunger body and a cylindrical-shaped portion at the proximal end of the plunger body.

Clause 17. The plunger according to clause 16, wherein the first segment of the at least one resiliently deflectable member is attached to an inner surface of the plunger body.

Clause 18. The plunger according to clause 17, wherein the at least one resiliently deflectable retaining member protrudes from the inner surface of the plunger body into the interior cavity.

Clause 19. The plunger according to any of clauses 1-18, further comprising a plunger cover disposed over at least a portion of an outer surface of the plunger body, the plunger cover comprising a resilient seal disposed around at least a portion of a circumferential sidewall of the plunger cover.

Clause 20. The plunger according to clause 19, wherein the resilient seal comprises an inner surface at least partially seated in a groove in the circumferential sidewall of the plunger body and an outer surface adapted to slidably engage with a barrel of a syringe.

Clause 21. The plunger according to any of clauses 1-20, wherein the actuating member is a cam member.

Clause 22. A plunger for use with a syringe, the plunger comprising:
a plunger body having a proximal end, a distal end, and a circumferential sidewall extending between the proximal end and the distal end along a plunger longitudinal axis;
at least one resiliently deflectable retaining member having a first segment attached to the plunger body and a second end protruding toward the distal end of the plunger body and deflectable relative to the first segment; and
at least one alignment member associated with the plunger body or the at least one resiliently deflectable retaining member,
wherein the at least one alignment member guides a piston into self-orienting alignment with the plunger during engagement of the plunger with the piston.

Clause 23. The plunger according to clause 22, further comprising at least one actuation member associated with the at least one resiliently deflectable retaining member, wherein the at least one actuation member interacts with the piston to deflect the at least one resiliently deflectable retaining member upon rotation of the plunger relative to the piston during disengagement of the plunger from the piston.

Clause 24. The plunger according to clause 23, wherein a terminal surface of the second segment of the at least one resiliently deflectable retaining member engages a surface of the piston to releasably lock the plunger with the piston.

Clause 25. The plunger according to clause 23 or clause 24, wherein the at least one actuation member is at the second segment of the at least one resiliently deflectable retaining member.

Clause 26. The plunger according to any of clauses 23-25, wherein the second segment of the at least one resiliently deflectable retaining member is deflectable radially relative to the first segment away from the plunger longitudinal axis.

Clause 27. A plunger for use with a syringe, the plunger comprising:
a plunger body having a proximal end, a distal end, and a circumferential sidewall extending between the proximal end and the distal end along a plunger longitudinal axis;
at least one resiliently deflectable retaining member having a first segment attached to the plunger body and a second segment deflectable relative to the first segment;
at least one alignment member associated with the plunger body or the at least one resiliently deflectable retaining member; and
at least one actuation member associated with the at least one resiliently deflectable retaining member,
wherein the at least one alignment member guides a piston into self-orienting alignment with the plunger during engagement of the plunger with the piston, and
wherein the at least one actuation member interacts with the piston to deflect the at least one resiliently deflectable retaining member upon rotation of the plunger relative to the piston during disengagement of the plunger from the piston.

Clause 28. The plunger according to clause 27, wherein the second segment of the at least one resiliently deflectable retaining member protrudes towards the distal end of the plunger body and wherein the second end of the at least one resiliently deflectable retaining member is deflectable radially relative to the first end away from the plunger longitudinal axis.

Clause 29. The plunger according to clause 27 or clause 28, wherein the second end of the at least one resiliently deflectable retaining member protrudes in a direction circumferentially around the longitudinal axis of the plunger body and wherein the second end of the at least one resiliently deflectable retaining member is deflectable circumferentially relative to the first end.

Clause 30. A syringe comprising:
a barrel having a barrel proximal end, a barrel distal end having a discharge nozzle, and a barrel sidewall extending between the barrel proximal end and the barrel distal end; and
a plunger slidably disposed within the barrel and reciprocally movable between the barrel proximal end and the barrel distal end, the plunger comprising:
a plunger body having a proximal end, a distal end, and a circumferential sidewall extending between the proximal end and the distal end along a plunger longitudinal axis;

at least one resiliently deflectable retaining member having a first segment attached to the plunger body and a second segment protruding toward the distal end of the plunger body and deflectable relative to the first segment; and at least one actuation member associated with the at least one resiliently deflectable retaining member, wherein the at least one actuation member interacts with a piston used to engage the plunger to radially deflect the at least one resiliently deflectable retaining member upon rotation of the plunger relative to the piston.

These and other features and characteristics of syringes, syringe plungers, and systems having syringes and/or syringe plungers, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

DETAILED DESCRIPTION

Figure 1:
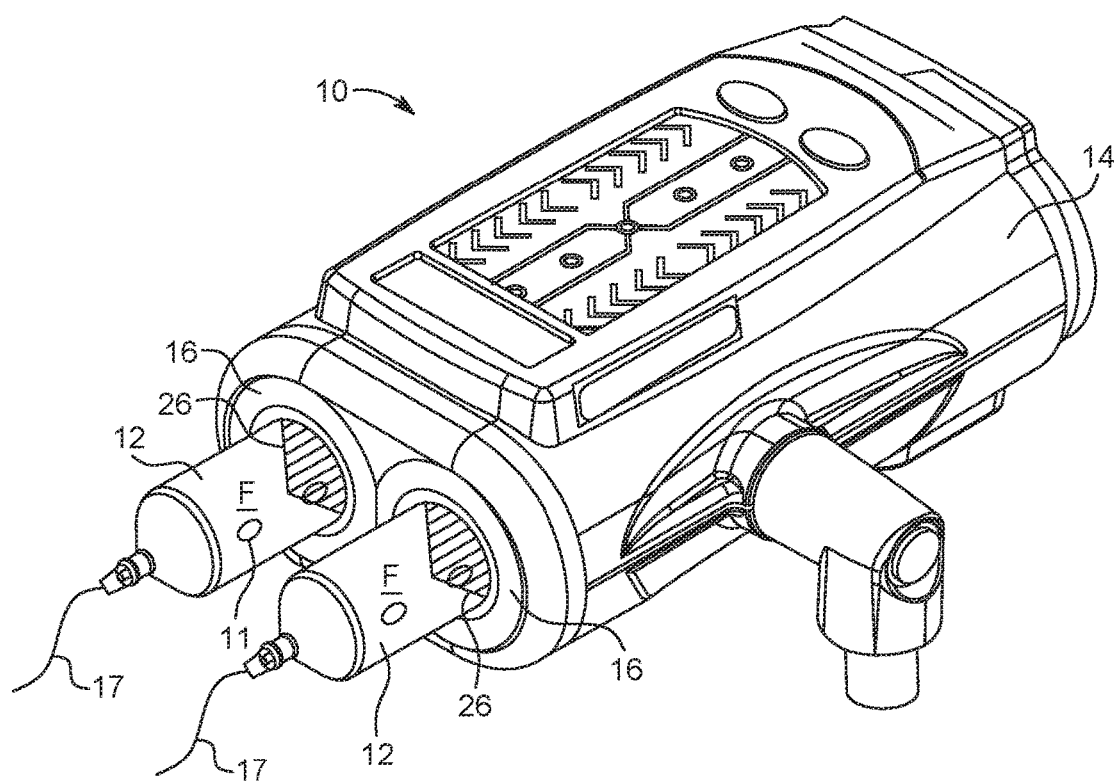
FIG. 1 is a top perspective view of a system including a fluid injector and at least one syringe according to an aspect of the present disclosure.

For purposes of the description hereinafter, the terms "upper", "lower", "right", "left", "vertical", "horizontal", "top", "bottom", "lateral", "longitudinal", and derivatives thereof shall relate to the components as they are oriented in the drawing/figures. When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "self-orienting" means that a piston head or a plunger orients itself to a correct orientation relative to a plunger or piston head, respectively, without a rotational effort by a technician or a fluid injector. The term "curvi-linear" refers to a shape of a surface that has one or more curved lines, one or more straight lines with one or more curved lines, and/or one or more straight line segments arranged non-linearly. It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

Referring to the drawings in which like reference characters refer to like parts throughout the several views thereof, the present disclosure is generally directed to a syringe plunger and a connection interface for connecting the syringe plunger to a piston of a fluid injector. Various aspects are directed to syringe plungers that may be connected to and disconnected from the piston. In various aspects, such plungers may be manually, hydraulically, or electrically activated. Furthermore, the present disclosure provides a quick and easy solution for engaging and disengaging the syringe plunger to and from the piston without a specific rotational orientation of the plunger about the plunger longitudinal axis relative to a longitudinal axis of the piston. For example, the piston may be advanced forward until it engages with the plunger, regardless of rotational orientation of the piston relative to the plunger about a longitudinal axis of the syringe, as described herein. In addition, a simple angular rotation of the plunger relative to the piston about a longitudinal axis of the syringe may allow for detachment of the two elements. In certain aspects, the syringe and the plunger may be engaged with a syringe port and piston extending from the syringe port, respectively. Concomitant disengagement of the syringe from the syringe port and the plunger from the piston may require the operator or technician to manually rotate the syringe. According to various aspects, rotation of the syringe may first result in disengagement of the plunger from the piston, as described herein, followed by disengagement of the syringe from the syringe port, for example as described in U.S. patent application Ser. Nos. 14/526,294 and 14/526,395, both of which were filed on Oct. 28, 2014, U.S. Pat. No. 6,652,489, issued Nov. 25, 2003, and U.S. Pat. No. 7,540,856, issued Jun. 2, 2009, the disclosures of each of which are incorporated by reference herein. In specific aspects, since rotation of the syringe also results in rotation of the plunger, due to frictional fit of plunger within the syringe, to affect disengagement of the plunger from the piston prior to disengagement of the syringe from the injector port, the rotational distance that the plunger must turn relative to the piston to cause disengagement of the plunger from the piston must be less than the rotational distance that the syringe must turn relative to the injector port to cause disengagement of the syringe from the port. Various aspects of the present disclosure provide a piston/plunger interface mechanism with features that provide this sequential disengagement requirement.

With reference to FIG. 1, a fluid injector 10 (hereinafter referred to as "injector 10"), such as an automated or powered fluid injector, is adapted to interface with and actuate at least one syringe 12, each of which may be independently filled with a medical fluid F, such as contrast media, saline solution, or any desired medical fluid. The injector 10 may be used during a medical procedure to inject the medical fluid into the body of a patient by driving a plunger 26 of the at least one syringe 12 with at least one piston. The injector 10 may be a multi-syringe injector, wherein several syringes 12 may be oriented in a side-byside or other arrangement and include plungers 26 separately actuated by respective pistons associated with the injector 10. In aspects with two syringes arranged in a side-by-side relationship and filled with two different medical fluids, the injector 10 may deliver fluid from one or both of the syringes 12.

The injector 10 may be enclosed within a housing 14 formed from a suitable structural material, such as plastic or metal. The housing 14 may have various shapes and sizes depending on a desired application. For example, the injector 10 may be a free-standing structure configured to be placed on the floor with a stationary or movable platform. Alternatively, the injector 10 may be configured for placement on a suitable table or support frame. The injector 10 includes at least one syringe port 16 for connecting the at least one syringe 12 to respective piston elements. In some aspects, the at least one syringe 12 includes at least one syringe retaining member for retaining the syringe 12 within the syringe port 16 of the injector 10. The at least one syringe retaining member operatively engages a locking mechanism provided on or in the syringe port 16 of the injector 10 to facilitate loading and/or removal of the syringe 12 to and from the injector 10, as described herein. The syringe retaining member and the locking mechanism together define a connection interface for connecting the syringe 12 to the injector 10.

At least one fluid path set 17 may be fluidly connected with the at least one syringe 12 for delivering medical fluid F from the at least one syringe 12 to a catheter, needle, or other fluid delivery device (not shown) inserted into a patient at a vascular access site. Fluid flow from the at least one syringe 12 may be regulated by a fluid control module (not shown). The fluid control module may operate various pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. One example of a suitable front-loading fluid injector 10 that may be modified for use with the above-described system including at least one syringe 12 and at least one syringe interface for self-oriented loading and releasable retaining of the at least one syringe 12 with the fluid injector 10 described herein with reference to FIG. 1 are disclosed in U.S. Pat. No. 5,383,858 to Reilly et al. and U.S. patent application Ser. Nos. 14/526,294 and 14/526,395, both of which were filed on Oct. 28, 2014 which are incorporated by reference in their entirety. Another example of relevant multi-fluid delivery systems that may be modified for use with the present system are found in U.S. Pat. No. 7,553,294 to Lazzaro et al.; U.S. Pat. No. 7,666,169 to Cowan et al.; International Patent Publication No. WO 2012/155035; and United States Patent Application Publication No. 2014/0027009 to Riley et al.; the disclosures of which are incorporated herein by reference. Other aspects may include new fluid injector systems designed to include various aspects of the piston plunger interfaces described herein.

Figure 2:
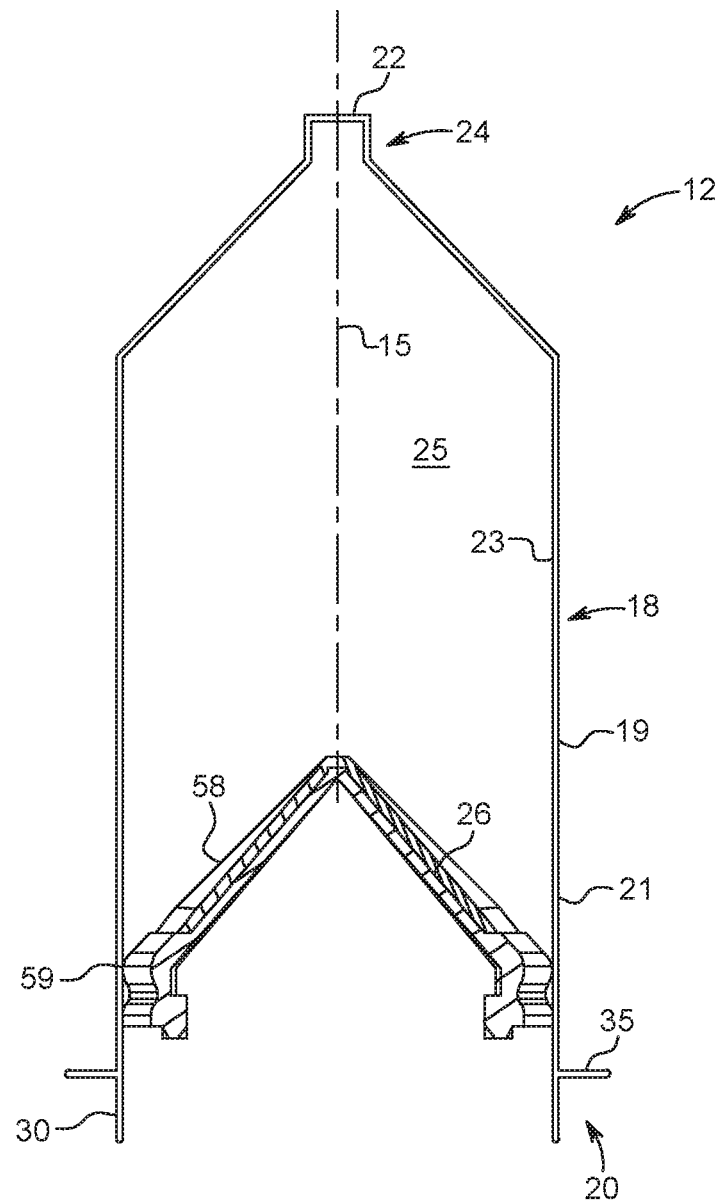
FIG. 2 is a side cross-sectional view of a syringe according to one aspect of the present disclosure.

Having described the general structure and function of the injector 10, the at least one syringe 12 will now be discussed in greater detail. With reference to FIG. 2, the syringe 12 generally has a cylindrical syringe barrel 18 formed from glass, metal, or a suitable medical-grade plastic. The barrel 18 has a proximal end 20 and a distal end 24, with a sidewall 19 extending therebetween along a syringe longitudinal axis 15 extending through a center of the barrel 18. The barrel 18 may be made from a transparent or translucent material, and may include at least one fluid verification member 11 (shown in FIG. 1) for verifying a presence of the fluid F within the syringe barrel 18. A nozzle 22 extends from the distal end 24 of the barrel 18. The barrel 18 has an outer surface 21 and an inner surface or wall 23 that defines an interior volume 25 for receiving the fluid therein. The proximal end 20 of the barrel 18 may be sealed with the plunger 26 that is slidable through the barrel 18. The plunger 26 may have a plunger cover 58 that forms a liquid-tight seal against the inner surface 23 of sidewall 19 of the barrel 18 as the plunger 26 is advanced therethrough. Details of various aspects of the plunger body and plunger cover are set forth herein.

A drip flange 35 may extend radially outwardly from the outer surface 21 of the syringe barrel 18 relative to the longitudinal axis 15. The drip flange 35 may extend around at least a portion of the outer circumference of the barrel 18. The drip flange 35 may prevent fluid that drips from the nozzle 22 from entering the syringe port 16 on the injector 10. In this manner, the drip flange 35 helps reduce the amount of fluid that may enter the syringe port 16 and jam or otherwise interfere with the connection interface and/or the interior mechanics and electronics of the injector 10. In some aspects, the drip flange 35 defines a stop surface that delimits the depth at which an insertion section 30 of the syringe 12 may be inserted into the syringe port 16 (shown in FIG. 1). The drip flange 35 may be formed integrally with the barrel 18 or it may be affixed or otherwise secured to the outer surface 21 of the barrel 18 using, for example, a frictional fit and/or an adhesive, welding, or by molding. In other aspects, the drip flange 35 may be formed on the outer surface 21 of the barrel 18 by etching, laser cutting, or machining.

With continued reference to FIG. 2, the proximal end 20 of the syringe 12 is sized and adapted for being removably inserted in the syringe port 16 of the injector 10 (shown in FIG. 1). In some aspects, the proximal end 20 of the syringe 12 defines the insertion section 30 that is removably insertable into the syringe port 16 of the injector 10 while the remaining portion of the syringe 12 remains outside of the syringe port 16. In certain aspects, the proximal end 20 of the syringe 12 includes one or more syringe retaining members (not shown) adapted to form a locking engagement with a corresponding locking mechanism in the syringe port 16 of the injector 10 for releasably retaining the syringe 12 in the syringe port 16. Various retaining members for releasably locking the syringe 12 with the injector 10 are described in, for example, U.S. patent application Ser. No. 14/526,294, filed on Oct. 28, 2014 and entitled "Self-Orienting Syringe and Syringe Interface", and U.S. patent application Ser. No. 14/526,395, filed on Oct. 28, 2014 and entitled "Self-Orienting Syringe and Syringe Interface", the disclosures of which are incorporated herein by reference in their entirety.

Exemplary syringes suitable for use with the injector 10 depicted in FIG. 1 and which can be adopted for use with a fluid verification system are described in U.S. Pat. No. 5,383,858 to Reilly et al., which is assigned to the assignee of the present application, the disclosure of which is incorporated by reference in its entirety. Additional exemplary syringes are disclosed in, for example, U.S. Pat. No. 6,322,535 to Hitchins et al. and U.S. Pat. No. 6,652,489 to Trocki et al., both of which are assigned to the assignee of the present application, and the disclosures of which are both incorporated by reference in their entireties.

Figure 3A:
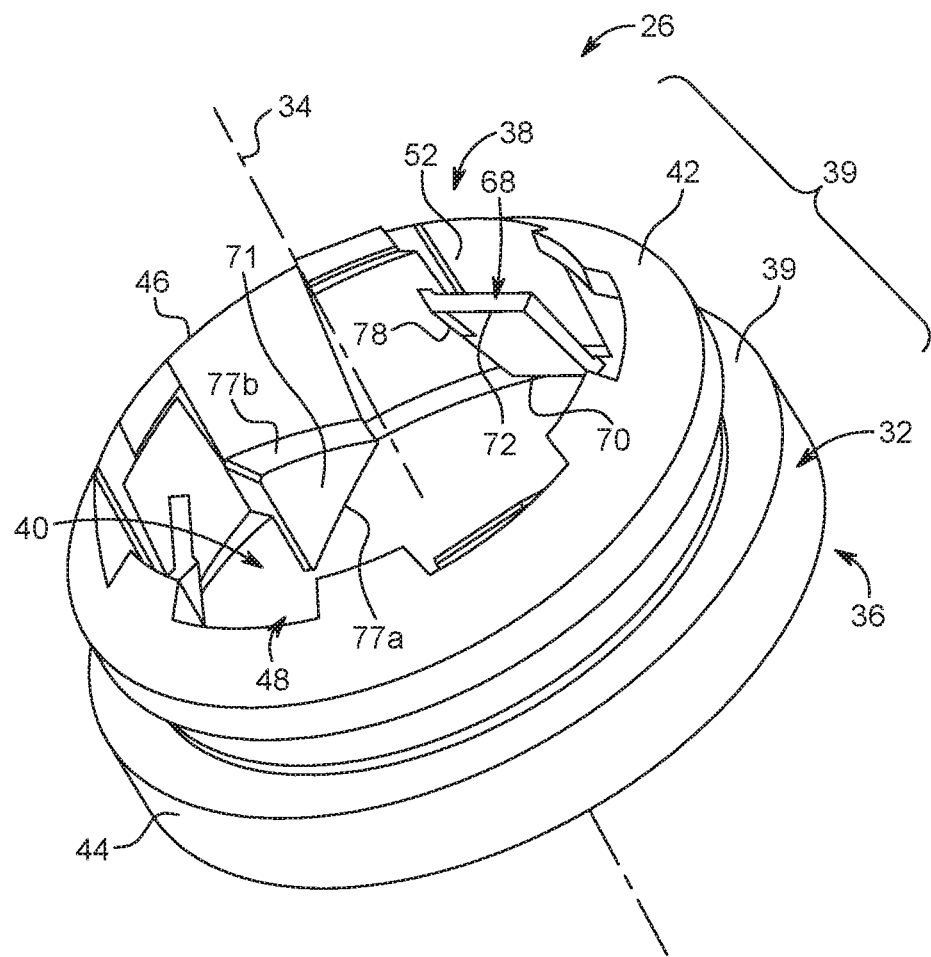
FIG. 3A is a top perspective view of a plunger according to one aspect of the present disclosure.
Figure 3B:
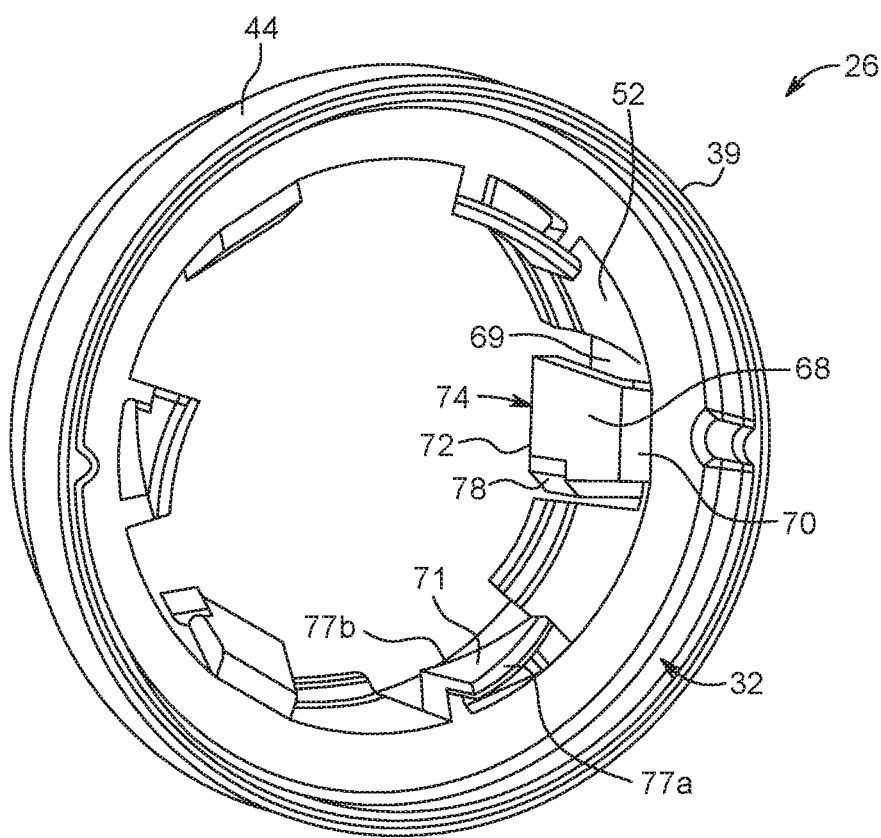
FIG. 3B is a bottom perspective view of the plunger shown in FIG. 3A.

With reference to FIGS. 3A-3B, the plunger 26 is shown in accordance with one aspect of the present disclosure. The barrel 18 of the syringe 12 is omitted from FIGS. 3A-3B for clarity. The plunger 26 includes a plunger body 32 defining a plunger longitudinal axis 34 (shown in FIG. 3A) and having a proximal end 36, a distal end 38, and a circumferential sidewall 39 connecting the proximal end 36 and the distal end 38. The sidewall 39 may have a uniform or non-uniform thickness between the proximal end 36 and the distal end 38. The sidewall 39 may have a continuous outer surface. In some aspects, the sidewall 39 may have a discontinuous outer surface having one or more portions of sidewall 39 separated by one or more voids or openings. The plunger body 32 may be formed from glass, metal, plastic, or other suitable material, including medical grade versions.

With continued reference to FIGS. 3A-3B, the plunger body 32 has an interior cavity 40 defined by a conical-shaped portion 42 at the distal end 38 of the plunger body 32 and a cylindrical-shaped portion 44 at the proximal end 36 of the plunger body 32. The conical-shaped portion 42 may be monolithically formed with the cylindrical-shaped portion 44. In some aspects, the conical-shaped portion 42 may be affixed or otherwise secured to the cylindrical-shaped portion 44 of the plunger body 32 using, for example, a frictional fit and/or an adhesive, welding, or by molding. The conical-shaped portion 42 may have a truncated end 46 that has a central opening 48. In some aspects, the distal end 38 of the plunger body 32 may be partially or fully enclosed such that the plunger 26 does not have a central opening 48. In other aspects, the distal end 38 of the plunger body 32 may have one or more radial openings, such as the openings 49 shown in FIG. 20B.

Figure 3C:
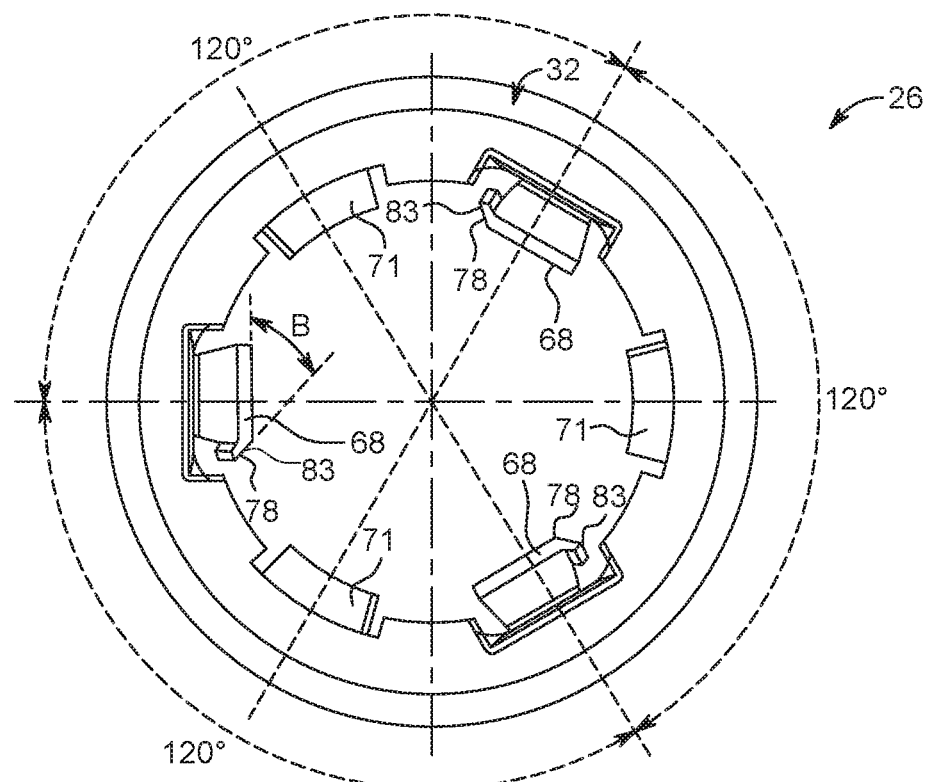
FIG. 3C is a bottom view of the plunger shown in FIG. 3A.
Figure 3D:
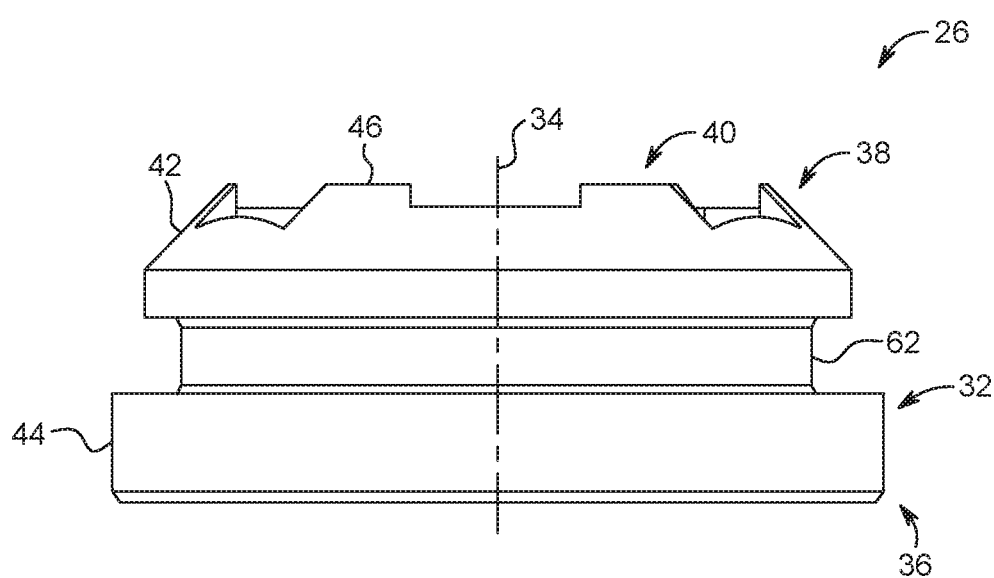
FIG. 3D is a side view of the plunger shown in FIG. 3A.
Figure 3E:
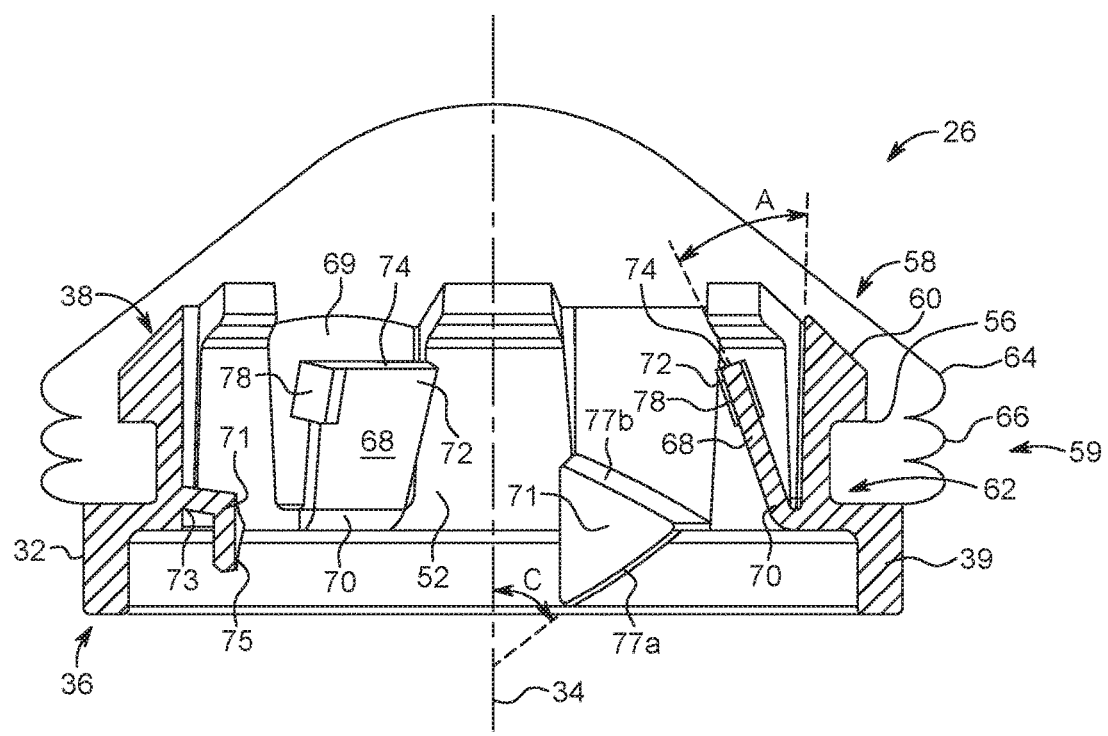
FIG. 3E is a side cross-sectional view of the plunger shown in FIG. 3A.

With reference to FIG. 3E, the plunger 26 may have a plunger cover 58 with a resilient seal 59 that covers at least a portion of an outer surface 60 of the plunger body 32. The seal 59 may be a resilient and flexible seal that engages the inner surface 23 of the syringe barrel 18 (shown in FIG. 2) such that the seal 59 seals the interior volume 25 of the syringe barrel 18 in a liquid-tight manner. The plunger cover 58 may be provided separately from the plunger body 32, or it may be integrally formed with the plunger body 32, such as by co-molding. In some aspects, the outer surface 60 of the plunger body 32 may have a circumferential groove 62. At least a portion of the plunger cover 58 may be retained within the circumferential groove 62. The exterior surface 64 of the seal 59 may have one or more lips, projections, or other sealing elements 66 that engage the inner surface 23 of the syringe barrel 18. In some aspects, the one or more sealing elements 66 of the seal 59 may be made from an elastomeric material that resiliently engages the inner surface 23 of the syringe barrel 18 (shown in FIG. 2). The at least one extension 56 on the plunger body 32 may prevent the seal 59 from coming out of axial engagement with the syringe 12 as the plunger 26 is moved through the syringe barrel 18.

Referring again to FIGS. 3A-3B, the plunger 26 may have at least one resiliently deflectable retaining member 68 (hereinafter "retaining member 68") protruding from the plunger body 32. In some aspects, the at least one retaining member 68 may protrude in a direction from the proximal end 36 toward the distal end 38 of the plunger body 32. In some aspects, the at least one retaining member 68 may protrude distally and radially inward from an inner surface 52 of the plunger body 32 into the interior cavity 40. In various aspects, the at least one retaining member 68 may be formed as a cantilever spring element, a coil spring element, or an elastomeric portion of the plunger body 32.

With reference to FIG. 3E, the at least one retaining member 68 has a first segment or a first end 70 connected to the plunger body 32 and a second segment or a second end 72 protruding distally from the first end 70. The second end 72 may deflect or twist relative to the first end 70. As described herein, the second end 72 may be radially deflectable relative to the first end 70 when the at least one retaining member 68 engages a piston of the fluid injector 10. In some aspects, the retaining member 68 may be radially deflected outwards, away from the longitudinal axis 34 when deflected by a portion of a piston during the engagement process. The resiliently deflectable retaining member 68 may then move radially inwards under the restoring force of the retaining member 68 to engage a portion of the piston to releasably lock the plunger body 32 with the piston. In some aspects where the retaining member 68 is circumferential with the plunger body 32 (described herein), the second end 72 may be circumferentially deflectable relative to the first end 70. The first end 70 and the second end 72 may be spaced apart in a direction that extends substantially along a direction of the plunger longitudinal axis 34 of the plunger 26. The at least one retaining member 68 may be linearly, stepwise, or curvilinearly contiguous between the first end 70 and the second end 72. In some aspects, one or more retaining members 68 may generally extend in a direction parallel to a direction of the plunger longitudinal axis 34. In other aspects, one or more retaining members 68 may extend in a direction that is angled relative to the direction of the plunger longitudinal axis 34. For example, one or more retaining members 68 may be angled at an angle A toward or away from the plunger longitudinal axis 34 from the inner surface 52 of the plunger body 32. The inner surface 52 of the plunger body 32 may have one or more pockets 69 that are recessed in a radially outward direction into the sidewall 39 to allow for an increased deflection of the second end 72 relative to the first end 70 of the at least one retaining member 68.

With reference to FIG. 3A, the at least one retaining member 68 may include a plurality of retaining members 68 spaced apart radially relative to the plunger longitudinal axis 34 along a circumference of the inner surface 52 of the interior cavity 40. The retaining members 68 may be separated from each other by portions of the inner surface 52 of the interior cavity 40. In aspects where two or more retaining members 68 are provided, the retaining members 68 may be evenly spaced apart from each other. In one exemplary and non-limiting aspect with three retaining members 68 having equal angular center-to-center separation therebetween, such as shown in FIG. 3C, each retaining member 68 is separated by 120 degrees from the retaining members 68 adjacent on either side. In another exemplary and non-limiting aspect with six retaining members 68 having equal angular separation therebetween, each retaining member 68 is separated by 60 degrees from the retaining members 68 adjacent on either side. In some aspects, the retaining members 68 may have unequal angular extension and/or unequal angular spacing between the retaining members 68 about the inner surface 52 of the interior cavity 40. The radial spacing of the at least one retaining member 68 relative to the plunger longitudinal axis 34 is selected to correspond to or operably interact with an outer shape of the piston, as described herein. In another exemplary and non-limiting aspect with two or more retaining members 68, each retaining member 68 has a center to center separation from the retaining members 68 adjacent on either side of an integer number of 60 degrees and furthermore each retaining member 68 has an angular extent less than 60 degrees, for example 15 to 45 degrees. This enables the release of the plunger 26 from the piston 88 with a relative rotation of 15 to 45 degrees. Optionally the relative rotation is less than 30 degrees.

With reference to FIG. 3E, the second end 72 of the retaining member 68 has at least one catch 74. The at least one catch 74 may be a terminal surface of the second end 72 of the retaining member 68. As described herein, the at least one catch 74 is shaped to be received within at least a portion of a recess, lip, or ledge on the piston to releasably lock the at least one retaining member 68, along with the plunger 26, to the piston with respect to motion in at least one direction. In some aspects, the at least one catch 74 may be linear or curvilinear to fit within a recess, lip, or ledge on the piston to releasably lock the at least one retaining member 68 and resist disconnecting from the piston 88 during reciprocal movement of the plunger 26 through the barrel 18 of the syringe 12 (shown in FIG. 2). In some aspects, the at least one catch 74 may be oriented in a direction substantially perpendicular to a direction of the plunger longitudinal axis 34. In other aspects, the at least one catch 74 may be angled relative to a direction of the plunger longitudinal axis 34. The at least one catch 74 may be continuous or discontinuous. In some aspects, the at least one catch 74 may protrude radially inward or outward relative to a body of the retaining member 68. The at least one catch 74 may be formed integrally with the second end 72 of the at least one retaining member 68 or it may be comolded, affixed, or otherwise secured to the second end 72 of the at least one retaining member 68 using, for example, a frictional fit and/or an adhesive, welding, or by molding. In other aspects, the at least one catch 74 may be formed on the second end 72 of the at least one retaining member 68 by etching, laser cutting, or machining.

At least one retaining member 68 may have at least one actuation member associated therewith. In various aspects, the at least one actuation member on the retaining member 68 of the plunger 26 is configured to interact with a corresponding actuation surface, such as an actuation surface on the piston 88 (shown in FIG. 4A), when the plunger 26 is connected to the piston 88. The at least one actuation member may interact with the corresponding actuation surface on the piston 88 to cause the at least one retaining member 68 to be released from the piston 88, such as when it is desired to disconnect the plunger 26 from the piston 88. Relative rotation between the piston 88 and the plunger 26 about the plunger longitudinal axis 34 causes at least a portion of the actuation member to engage at least a portion of the piston 88, such as the corresponding actuation surface on the piston 88. For example, the piston may be substantially fixed against rotation in the direction of the plunger 26, while the plunger 26 is rotated about the plunger longitudinal axis 34, by frictional contact with an inner wall of a syringe during rotation of the syringe, to cause the actuation member on the plunger 26 to engage, through rotational contact, the corresponding actuation surface on the piston 88. Alternatively, the plunger 26 may be fixed, while the piston 88 is rotated about the piston longitudinal axis 115 (shown in FIG. 4A) to cause the actuation surface on the plunger 26 to engage, through rotational contact, the corresponding actuation surface on the piston 88. As a further alternative, the piston 88 and the plunger 26 may be rotated in opposite directions relative to one another about their respective longitudinal axes, or the piston 88 and the plunger 26 may be rotated in a same direction, such as clockwise or counter-clockwise direction, about their respective longitudinal axes at different rotation rates. The engagement between the actuation member on the plunger 26 and the corresponding actuation surface on the piston may be through sliding contact occurring when the rotational position of the actuation member on the plunger 26 is rotationally aligned with the rotational position of the corresponding actuation surface on the piston 88. In some aspects, a sliding contact between the actuation member on the plunger 26 and the corresponding actuation surface on the piston 88 during relative rotational movement between the piston 88 and the plunger 26 causes a movement of the at least one retaining member 68 to a disengaged position to release the plunger 26 from the piston 88.

With reference to FIGS. 3A-3B, the plunger 26 may have at least one actuation member, such as at least one first cam member 78. In some aspects, the first cam member 78 may be provided directly on the retaining member 68, or it may be provided on a portion of the plunger body 32 or an extension therefrom such that movement of the cam member 78 causes a corresponding disengagement of the retaining member 68. In some aspects, the at least one first cam member 78 may be provided between the first end 70 and the second end 72 of the retaining member 68. The at least one first cam member 78 interacts with a piston of the fluid injector 10 (shown in FIG. 1) to radially deflect the at least one retaining member 68 upon rotation of the plunger 26 relative to the piston, as described herein. In some aspects, the position of the at least one first cam member 78 may be selected to allow for an increased radial deflection of the at least one first cam member 78 upon relative rotation between the plunger 26 and the piston. In such aspects, the at least one first cam member 78 may be provided closer to the second end 72 of the retaining member 68.

In some aspects, the at least one retaining member 68 may have the catch 74 formed thereon, while the actuation member, such as the cam member 78, may be formed as a separate component that interacts with the at least one retaining member 68. The actuation member, for example, the cam member 78 used to disengage the at least one retaining member 68, may be a second, separate member attached to the plunger body 32. Alternatively, the actuation member may be formed on a second separate member which is attached to the plunger body 32 and interacts with the piston 88 and the at least one retaining member 68 to transmit force, motion, or displacement from the piston 88 to the at least one retaining member 68 to deflect it for disengagement from the plunger 26.

In some aspects, the at least one first cam member 78 may protrude at an angle relative to a plane defined by a body of the retaining member 68. With reference to FIG. 3C, the at least one first cam member 78 may be angled at an angle B relative to the plane defined by the body of the retaining member 68. In various aspects, the at least one first cam member 78 may be formed as a sidewall, lip, extension, or protrusion that is associated with the body of the retaining member 68. The at least one first cam member 78 may be planar, curved, or a combination thereof. The at least one first cam member 78 may be formed as a continuous surface or a discontinuous surface formed from two or more separate surfaces that together form the at least one first cam member 78. The at least one first cam member 78 may have an angled engagement surface 83 that interacts with the piston to disengage the plunger 26 from the piston, as described herein. The position of the at least one first cam member 78 between the first end 70 and the second end 72 of the retaining member 68 minimizes the radial protrusion of the at least one first cam member 78 while still allowing a full radial deflection of the at least one retaining member 68 upon rotation of the plunger 26 relative to the piston 88 to allow disengagement of the plunger 26 from the piston 88, as described herein. In some aspects, the at least one first cam member 78 may be provided on at least a portion of the at least one catch 74. A plurality of first cam members 78 may be axially spaced apart along a length of the retaining member 68 between the first end 70 and the second end 72. The at least one first cam member 78 may be formed integrally with the at least one retaining member 68 or it may be affixed or otherwise secured to the at least one retaining member 68 using, for example, a frictional fit and/or an adhesive, welding, or by molding. In other aspects, the at least one first cam member 78 may be formed on the at least one retaining member 68 by etching, laser cutting, or machining.

With reference to FIG. 3A, according to certain aspects, the plunger 26 may have at least one first alignment member 71 protruding radially inward from the plunger body 32. In some aspects, the at least one first alignment member 71 may protrude in a direction from the distal end 38 toward the proximal end 36 of the plunger body 32. In some aspects, the at least one first alignment member 71 may protrude proximally from the inner surface 52 of the interior cavity 40 of the plunger body 32.

With reference to FIG. 3E, the at least one first alignment member 71 has a first end 73 connected to the plunger body 32 and a second end 75 protruding radially inward from the first end 73. The at least one first alignment member 71 is shaped and/or configured for facilitating self-orienting alignment of the piston 88 with the plunger 26. In some aspects, at least a portion of the at least one first alignment member 71 may extend in a direction that is angled relative to the direction of the plunger longitudinal axis 34. For example, at least one first alignment member 71 may have a proximal alignment surface 77a that is angled at an angle C relative to the longitudinal axis 34 to facilitate positioning of the retaining member 68 during connection of the plunger 26 to a piston. The at least one first alignment member 71 may have a distal alignment surface 77b that is angled in a direction opposite to the proximal alignment surface 77a to facilitate positioning of the retaining member 68 when the plunger 26 is being disconnected from the piston. The proximal alignment surface 77a helps guide the piston 88 into self-orienting alignment with the plunger 26, as described herein, for example by rotation of a portion of the piston 88 relative to the plunger 26 utilizing a one-way clutch associated with the piston 88.

With reference to FIG. 3C, a plurality of first alignment members 71 may be spaced apart radially relative to the plunger longitudinal axis 34 along a circumference of the inner surface 52 of the interior cavity 40. In some aspects, the number of first alignment members 71 may be equal or unequal to the number of retaining members 68. When equal in number, the first alignment members 71 may be disposed between the retaining members 68 such that each first alignment member 71 has a retaining member 68 on either side of the first alignment member 71. The first alignment members 71 may be separated from each other by portions of the inner surface 52 of the interior cavity 40. In aspects where two or more first alignment members 71 are provided, the first alignment members 71 may be evenly spaced apart from each other. In one exemplary and non-limiting aspect with three first alignment members 71 having equal angular separation therebetween, such as shown in FIG. 3C, each first alignment member 71 is separated by 120 degrees from the first alignment members 71 adjacent on either side. In another exemplary and non-limiting aspect with six first alignment members 71 having approximately equal angular center-to-center separation therebetween, each first alignment member 71 is separated by 60 degrees from the first alignment members 71 adjacent on either side. In some aspects, the first alignment members 71 may have unequal angular extension and/or unequal angular spacing between adjacent first alignment members 71 about the inner surface 52 of the interior cavity 40. The radial spacing of the at least one first alignment member 71 relative to the plunger longitudinal axis 34 is selected to correspond to or operably interact with an outer shape of the piston 88 to allow for alignment of the plunger 26 with the piston 88, as described herein. The at least one first alignment member 71 may be constituted from or composed of multiple members, optionally separately attached to the inner surface 52 of the plunger body 32, whose alignment surfaces, both real and virtual, interact to perform the alignment function. Similarly, an at least one retaining member 68 may be constituted from or composed of multiple members, optionally separately attached to the inner surface 52 of the plunger body 32, whose catches 74, interact to perform the engagement, connection, attachment, or retention functions. Similarly, an at least one actuation member may be constituted from or composed of multiple members, optionally separately attached to the inner surface 52 of the plunger body 32, which interact to provide the activation of the at least one retaining member 68 to perform the disengagement, disconnect, separation, or release function. Optionally, the at least one alignment member 71, the at least one retaining member 68, and/or the at least one actuation member may be attached to each other and interact or transmit force directly from one to another, or optionally may be separate and interact with each other through surfaces between them that transmit force, motion, or deflection from one to another, directly or indirectly, or through their action on the plunger body 32. Similarly, the force, motion, or deflection for activation to accomplish release of a retaining member 68 may occur through the movement of or force transmitted from a second retaining member 68 or intermediate linkage or mechanism.

Figure 4A:
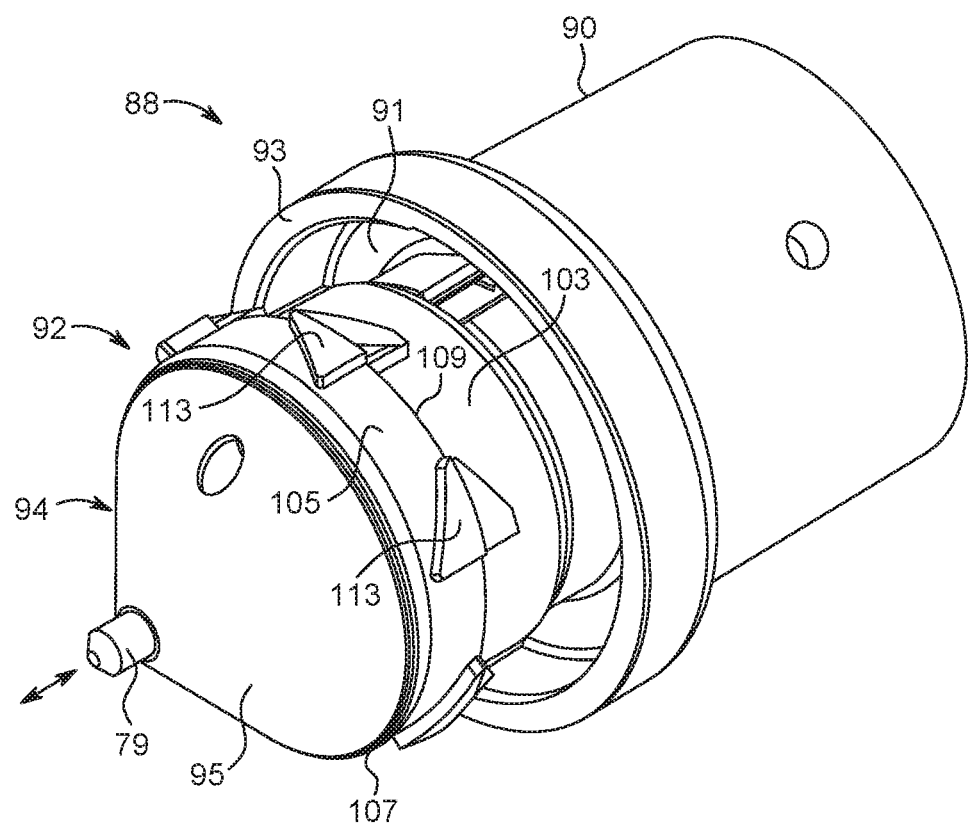
FIG. 4A is a top perspective view of a piston according to one aspect of the present disclosure.

Referring to FIG. 4A, a piston 88 (shown in FIG. 4A as only the distal portion of piston 88) is configured to interact with the plunger 26 (shown in FIG. 3A) to releasably lock the plunger 26 such that the plunger 26 can be driven reciprocally within the barrel of the syringe 12 (shown in FIG. 2). The piston 88 is extendible and retractable from the housing 14 of the fluid injector 10 (shown in FIG. 1) via a powered means (not shown) preferably contained within housing 14. The powered means may include, for example, an electric motor, a hydraulic system, or a pneumatic system, including appropriate gearing (not shown). As known in the art, the fluid injector 10 also may include a controller (not shown) for controlling operation of the powered means and thereby controlling operation of the piston 88.

Figure 4B:
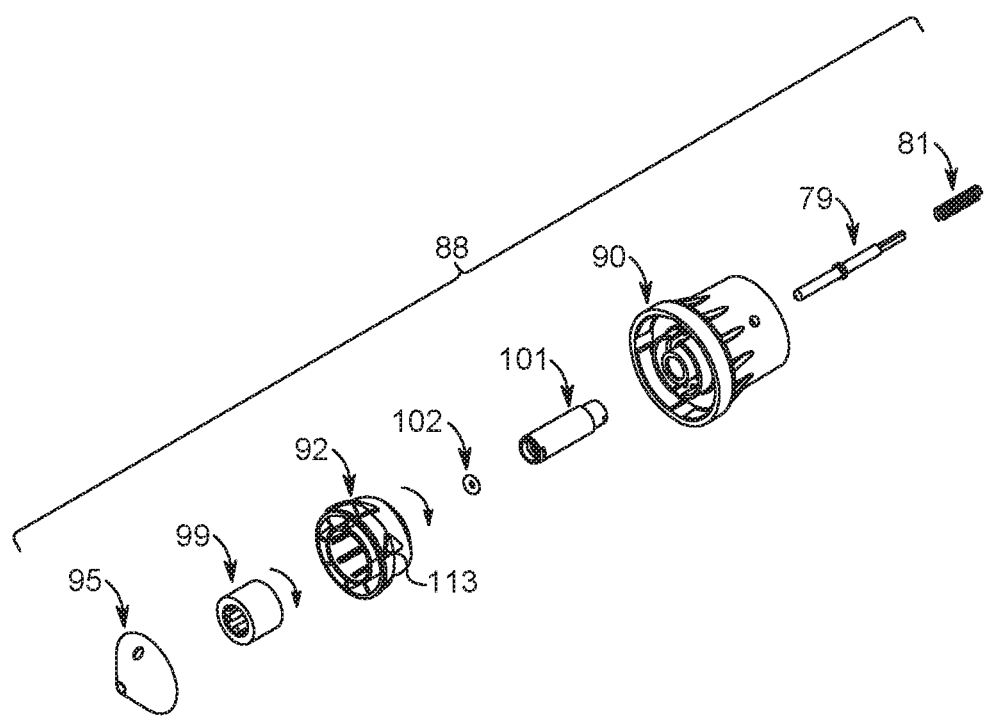
FIG. 4B is an exploded perspective view of the piston shown in FIG. 4A.

With continued reference to FIG. 4A, the piston 88 includes a stem 90 connected to the proximal portion of the piston 88 within the injector 10 (shown in FIG. 10A) and a piston head 92 formed on a distal end of the stem 90. At least a portion of the piston head 92 extends distally from the stem 90. The piston 88 is constructed from a rigid material, such as metal or plastic that resists deformation. The stem 90 may have a cavity 91 for collecting any fluid that may drip from the syringe. The piston head 92 has a substantially cylindrical structure with a pointed distal end 94 with a cap 95 that is shaped to be received inside at least a portion of the interior cavity 40 (shown in FIG. 3A) of the plunger 26. In some aspects, a sensing member 79, such as a pin connected to a sensor, may be provided. The sensing member 79 may extend along a longitudinal axis of the piston 88 and may protrude through at least a portion of the piston head 92, such as through at least a portion of the cap 95. The sensing member 79 may be operative for sensing contact with a surface, such as a surface of the plunger 26 and/or the plunger cover 58, and control a movement of the piston 88 based on the sensed condition. For example, an initial contact between the sensing member 79 and the plunger 26 and/or the plunger cover 58 may cause the pin to be moved in a proximal direction such that it makes contact with the sensor. The sensing member 79 may be biased in an extended position by a resilient element 81 (shown in FIG. 4B), such as a spring. The sensor may be connected to the controller of the injector such that, upon activation of the sensor by the pin, the controller controls the movement of the drive mechanism. For example, the drive mechanism may be stopped or slowed from a first rate to a second, slower rate.

The piston head 92 may be rotatable relative to the stem 90. In some aspects, the piston head 92 may be rotatable in one direction only, such as a clockwise or a counter-clockwise direction, relative to the stem 90. A one-way rotation mechanism 99 (shown in FIG. 4B), such as a one-way clutch mechanism, may be provided to allow the rotation of the piston head 92 in a first direction only, such as the clockwise or the counter-clockwise direction. The one-way rotation mechanism 99 may be rotatable around a central shaft 101 having a seal 102, such as an O-ring seal. In some aspects, the one-way rotation mechanism 99 may have a stop that prevents rotation of the piston head 92 in a second direction opposite the first direction, such as the counter-clockwise or the clockwise direction, respectively. In other aspects, the one-way rotation mechanism 99 may be provided on at least a portion of the plunger 26.

Figure 4C:
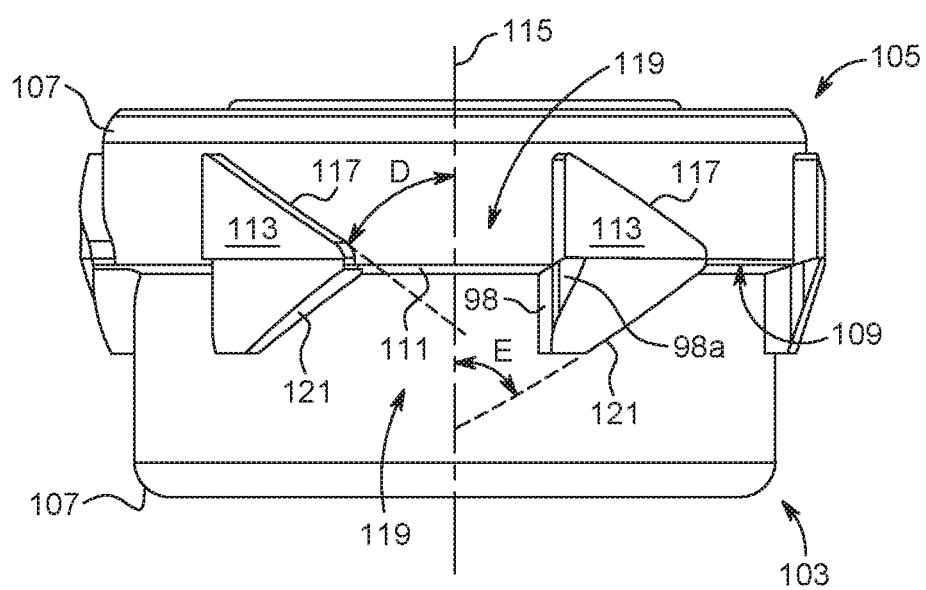
FIG. 4C is a side view of the piston shown in FIG. 4A.
Figure 5A:
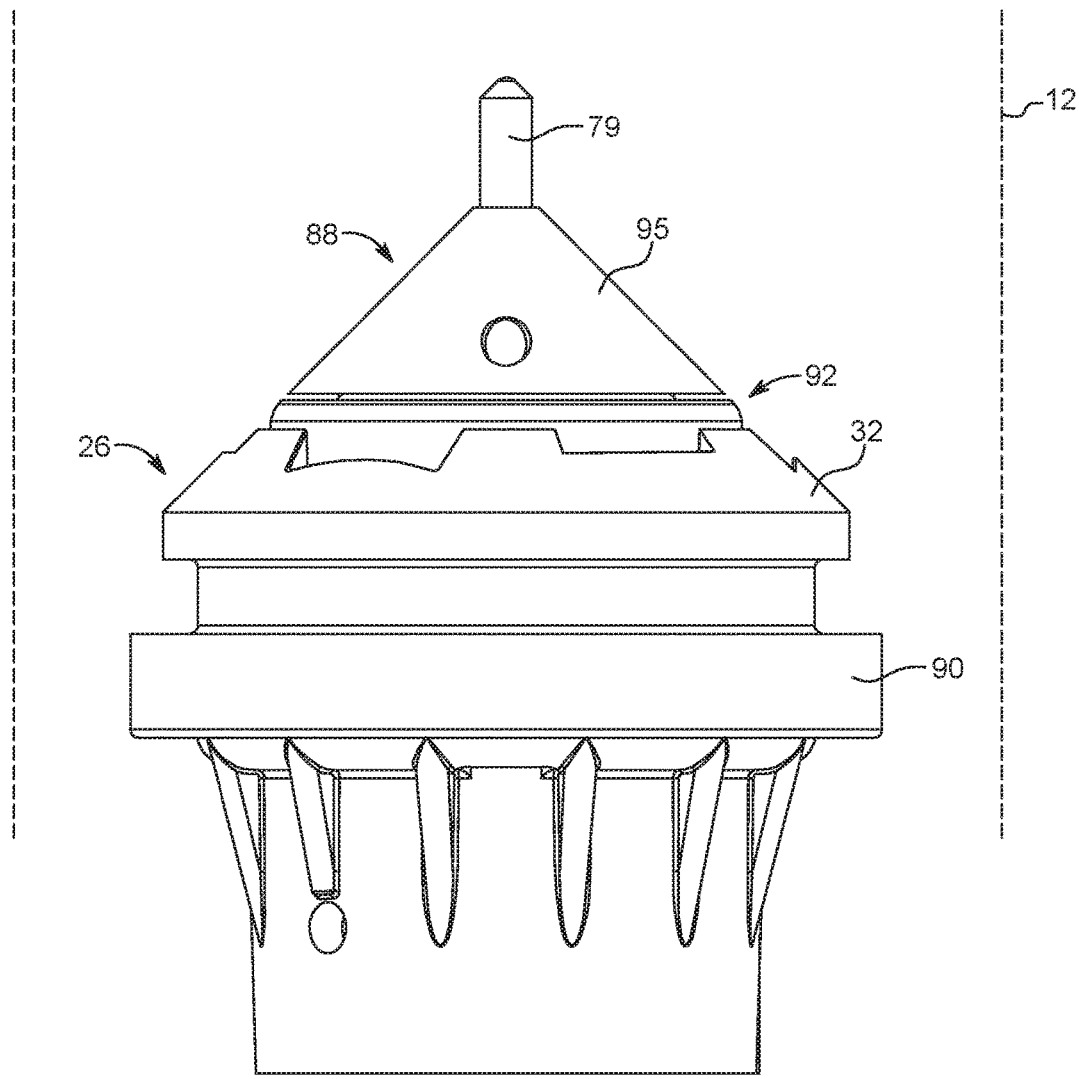
FIG. 5A is a side view of a plunger and a piston in an assembled state.

With reference to FIG. 4C, the piston head 92 has a proximal portion 103 connected to a distal portion 105. Terminal ends of the proximal and distal portions 103, 105 may have a radiused or chamfered edge 107. At least a portion of the proximal portion 103 has a smaller outer diameter compared to an outer diameter of the distal portion 105 such that a radial lip 109 is formed at a transition between the proximal portion 103 and the distal portion 105. The radial lip 109 may be continuous or discontinuous around a circumference of the piston head 92. In some aspects, the radial lip 109 defines a locking ledge 111 for engaging the catch 74 (shown in FIG. 5D) of the at least one retaining member 68 when the plunger 26 is fully seated on the piston head 92. At least a portion of the retaining member 68 shown in FIG. 5D is shown as being hidden behind the piston head 92 due to the rotational position of the plunger 26 relative to the piston head 92 about the piston longitudinal axis 115.

With continued reference to FIG. 4C, the piston head 92 may have at least one second alignment member 113 protruding radially outward from an outer surface of the piston head 92. The at least one second alignment member 113 may be shaped and/or configured for interacting with the first alignment member 71 (shown in FIG. 5B) of the plunger 26 for facilitating alignment of the piston 88 with the plunger 26 in order to allow for a releasable locking connection of the plunger 26 with the piston 88. In some aspects, at least a portion of the at least one second alignment member 113 may extend in a direction that is angled relative to the direction of a piston longitudinal axis 115. For example, at least one second alignment member 113 may have a guiding surface 117 that is angled at an angle D relative to the piston longitudinal axis 115. The guiding surface 117 is desirably angled such that the piston head 92 may rotate around the piston stem 90, for example around the axis of the one-way rotation mechanism 99, when the proximal alignment surface 77*a* of the first alignment member 71 contacts the guiding surface 117 of the second alignment member 113.

In some aspects, a plurality of second alignment members 113 may be spaced apart radially relative to the piston longitudinal axis 115 along an outer circumference of the piston head 92. In some aspects, the number of second alignment members 113 may be equal to a total number of retaining members 68 and first alignment members 71 on the plunger 26. The second alignment members 113 are spaced apart circumferentially such that a retaining member 68 or a first alignment member 71 may be received between adjacent second alignment members 113. The second alignment members 113 may be separated from each other by portions of an outer surface of the proximal portion 103 and/or the distal portion 105 of the piston head 92. In aspects where two or more second alignment members 113 are provided, the second alignment members 113 may be evenly spaced apart from each other. In one exemplary and non-limiting aspect with six second alignment members 113 having equal angular separation therebetween, such as shown in FIG. 4A, each second alignment member 113 is separated by 60 degrees from the second alignment members 113 adjacent on either side. In some aspects, the second alignment members 113 may have unequal angular extension and/or unequal angular spacing between the second alignment members 113 about the outer surface of the proximal portion 103 and/or the distal portion 105 of the piston head 92. The radial spacing of the second alignment members 113 relative to the piston longitudinal axis 115 is selected to correspond to or operably interact with an inner shape of the plunger 26 to allow the one or more retaining members 68 to be received into the locking ledge 111. Locking ledge 111 may be radially perpendicular to the longitudinal axis 115 or in certain aspects locking ledge 111 may be radially angled relative to the longitudinal axis 115. In certain aspects, locking ledge 111 may be angled with an angle complementary to an angle of the catch 74, such as the angle of the catch 74 shown in FIG. 3E.

With reference to FIG. 4C, each of the guiding surfaces 117 of the second alignment members 113 define a travel path for guiding the movement of the proximal alignment surface 77*a* of the first alignment member 71 in and out of a recess 119 defined between adjacent second alignment members 113. The guiding surfaces 117 may be inclined or angled radially and axially relative to the piston longitudinal axis 115 to guide the movement of the proximal alignment surfaces 77*a*. The guiding surfaces 117 aid in self-orienting the piston head 92 as the plunger 26 is brought into contact with the piston 88 by guiding the one or more proximal alignment surfaces 77*a* on the plunger 26 into the corresponding recess 119 on the piston head 92. In this manner, a piston 88 whose piston longitudinal axis 115 is rotationally misaligned with the plunger longitudinal axis 34 and the one or more first alignment members 71 which are initially misaligned relative to the corresponding one or more second alignment members 113 is rotated in a rotational direction of the one-way rotation mechanism 99 and brought in alignment axially and rotationally such that the one or more first alignment members 71 are received within the recess 119 between adjacent second alignment members 113. In this manner, the one or more retaining members 68 are brought into rotational alignment with the recess 119 having the locking ledge 111 adjacent the recess 119.

The one or more second alignment members 113 may have a bottom surface 121 that is angled relative to the direction of a piston longitudinal axis 115. For example, the bottom surface 121 may be angled at an angle E relative to the piston longitudinal axis 115. Angle E may be the same or different than angle D of the guiding surface 117. In another aspect, bottom surface 121 may be rounded or angled to merge with the proximal wall or proximal end 103.

The piston head 92 further has an actuation surface that interacts with the actuation member on the plunger 26, such as the first cam member 78. In some aspects, the actuation surface on the piston head 92 may be a second cam member 98 or a cam following surface. In some aspects, the actuation surface or second cam member 98 cooperates with the first cam member 78 on the at least one retaining member 68 of the plunger 26, as described herein. The actuation surface or second cam member 98 desirably has a shape that, upon relative rotation between the piston 88 and the plunger 26, the actuation surface or second cam member 98 engages the first cam member 78 to cause the at least one retaining member 68 to be deflected from the piston head 92 to disengage catch 74 of retaining member 68 from the locking ledge 111 such that the plunger 26 disengages and can be removed from the piston 88. In some aspects, the actuation surface or second cam member 98 may be formed on the second alignment member 113 on the piston head 92. The actuation surface or second cam member 98 may be a surface that is aligned with a direction of the piston longitudinal axis 115. In certain aspects, the actuation surface or second cam member 98 may have a chamfered portion 98a to facilitate the initial movement and/or the passing of the first cam member 78 after the retaining member 68 is deflected sufficiently to allow the retaining member to be released. In other aspects, the actuation surface 98 may be radially aligned and parallel to longitudinal axis 115.

The piston 88 is configured to interact with the plunger 26 to releasably lock with plunger 26, such as shown in FIG. 3A. By locking the piston 88 to the plunger 26, the plunger 26 can be driven reciprocally within the barrel of the syringe 12 (shown in FIG. 2). The actuation surface or second cam member 98 on the piston 88 cooperates with the first cam member 78 on the at least one retaining member 68 of the plunger 26, to releasably lock the plunger 26 to the piston 88. Further, due to the distal arrangement and in certain aspects, the radially inwardly angled nature, of the at least one retaining member 68, the locking force between the locking ledge 111 of piston 88 and the catch 74 of the retaining member 68 is increased due to the compressive force as the piston 88 withdraws the plunger 26 in the proximal direction during a syringe filling process. The locking or engagement of the plunger 26 to the piston 88, and the unlocking or disengagement of the plunger 26 from the piston 88 will be described herein with reference to FIGS. 5A-5C. The syringe 12, shown initially in phantom in FIG. 5A is omitted from the remainder of FIGS. 5B-5D for clarity.

To engage the plunger 26 with the piston 88, the syringe 12 is first inserted into the syringe port 16 of the fluid injector 10 (shown in FIG. 1). Once or while the syringe 12 is inserted into the syringe port 16, various locking mechanisms (not shown) may be used to retain the syringe 12 within the syringe port 16 to prevent detachment of the syringe 12 from the syringe port 16. Initially, the plunger 26 may be positioned at the proximal end 20 of the syringe barrel 18. In some aspects, the plunger 26 is positioned at any axial location between the proximal end 20 and the distal end 24 of the syringe barrel 18. The piston 88 may then be advanced distally toward the plunger 26 for engagement of the piston head 92 with the plunger 26. In some aspects, the piston 88 may be advanced distally toward the plunger 26 by way of the powered means operated by a controller. In other aspects, the piston 88 may be advanced distally toward the plunger 26 by manual operation.

Figure 5B:
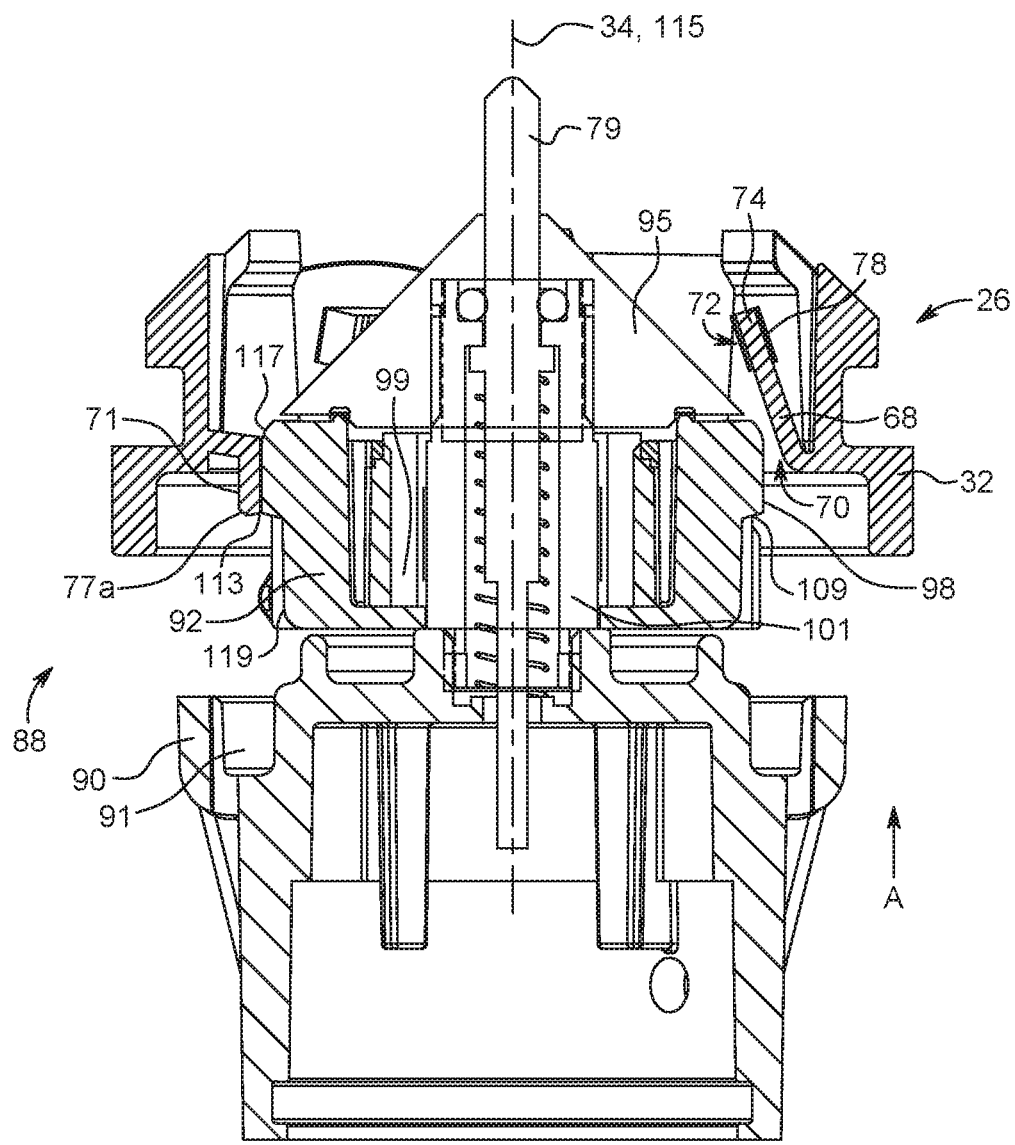
FIG. 5B is a side cross-sectional view of the plunger and the piston during initial engagement of the piston with the plunger.

With reference to FIG. 5B, the piston 88 is advanced axially in a distal direction shown by the arrow A. If the piston 88 is rotationally misaligned relative to the plunger 26 about the longitudinal axis 115 such that the first alignment members 71 on the plunger 26 are not in rotational alignment to be received within the recesses 119 (shown in FIG. 4C) on the plunger head 92, the proximal alignment surface 77a of the first alignment member 71 on the plunger 26 contacts the guiding surface 117 of the second alignment member 113 on the piston head 92. The proximal alignment surface 77a and the guiding surface 117 are angled in a same direction relative to the longitudinal axes 34, 115 such that continued movement of the piston 88 in a distal direction causes the proximal alignment surface 77a to engage the guiding surface 117. Engagement of the proximal alignment surface 77a with the guiding surface 117 causes the piston head 92 to automatically rotate in a free rotation direction of the one-way rotation mechanism 99. Such rotation of the piston head 92 aligns the first alignment members 71 and the retaining members 68 to be received within the recesses 119 between adjacent second alignment members 113. In this manner, the piston 88 self-orients itself relative to the plunger 26 such that the plunger 26 may be releasably locked with the piston 88. If the piston 88 is rotationally aligned relative to the plunger 26 such that the first alignment members 71 on the plunger 26 are in rotational alignment with the second alignment members 113 on the piston head 92, the first alignment members 71 and the retaining members 68 on the plunger 26 can be received within the recesses 119 between adjacent second alignment members 113 without rotation of the piston head 92.

Figure 5C:
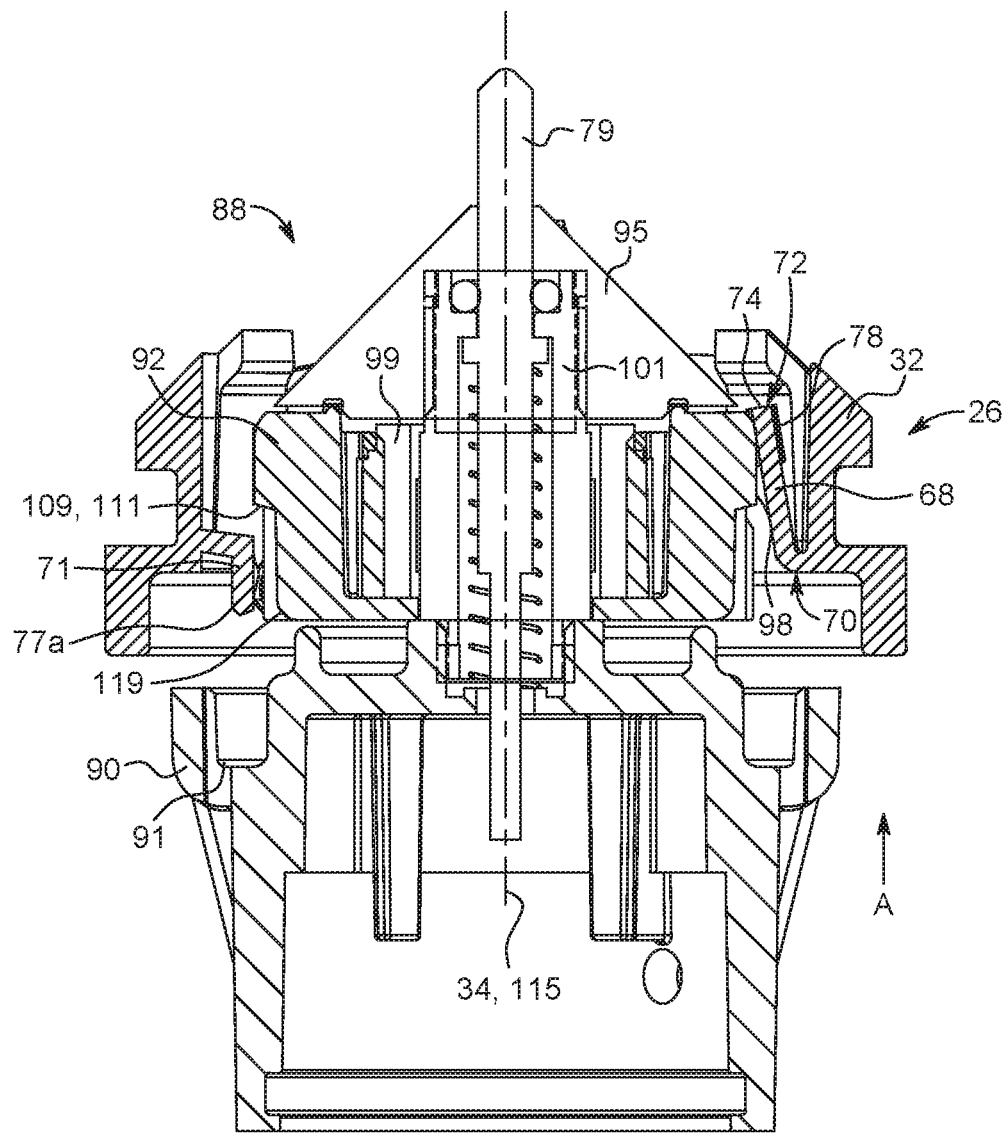
FIG. 5C is a side cross-sectional view of the plunger and the piston prior to full engagement of the piston with the plunger.
Figure 5D:
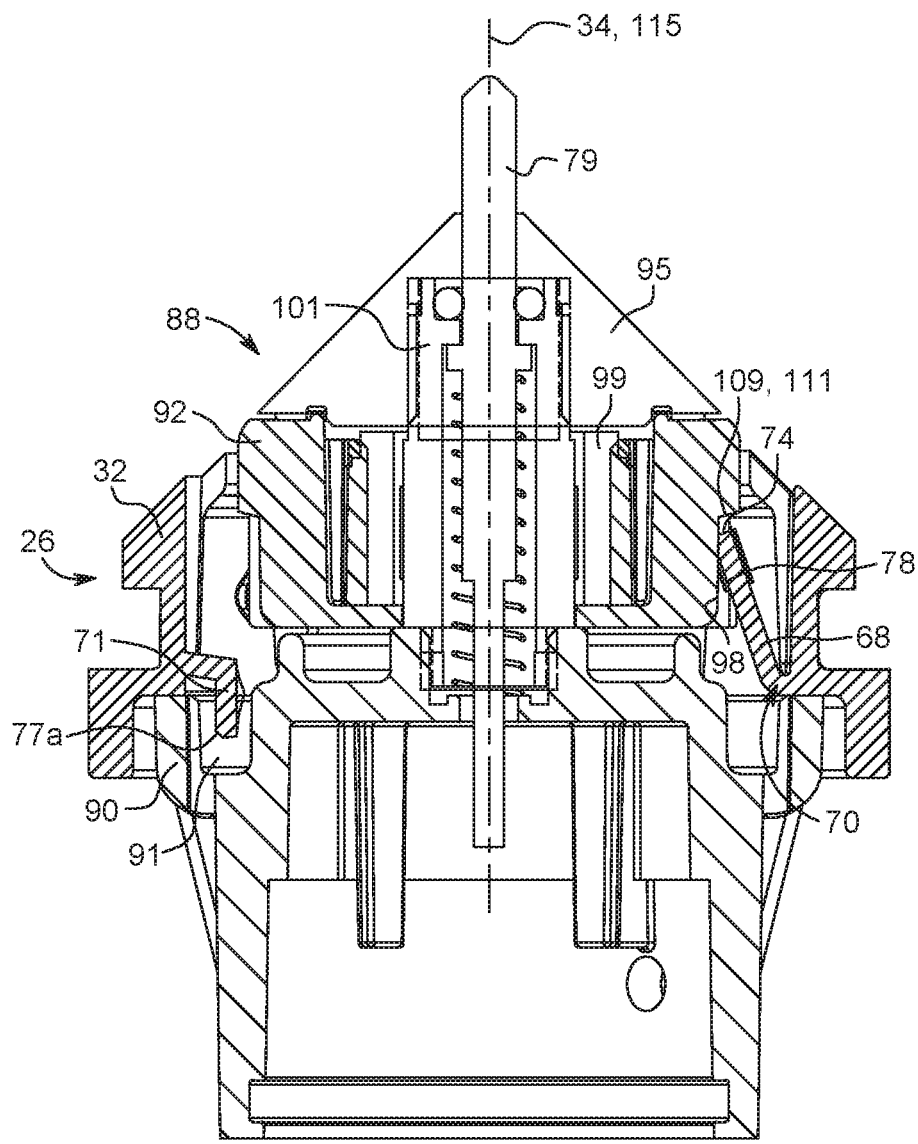
FIG. 5D is a side cross-sectional view of the plunger and the piston during full engagement of the piston with the plunger.

With reference to FIG. 5C, after aligning the first alignment members 71 and the retaining members 68 to be received within the recesses 119 between adjacent second alignment members 113, the piston 88 is advanced further in the distal direction. Such movement of the piston 88 in the distal direction, causes the retaining members 68 to initially engage an outer sidewall of the distal portion 105 of the piston head 92. Continued distal movement of the piston 88 causes the retaining members 68 to deflect radially outward relative to the plunger longitudinal axis 34 from a first, undeflected position, to a second, radially deflected position. The piston 88 is advanced distally until the terminal portion of the second end 72 of each retaining member 68 clears the radial lip 109. The retaining members 68 then deflect radially inward toward or to their initial undeflected position, for example due to the restoring force built up in the retaining members 68 during radial deflection. As shown in FIG. 5D, the catch 74 of at least one retaining member 68 is retained within the locking ledge 111 to prevent disengagement of the plunger 26 from the piston head 92. Distal movement of the piston 88 may be stopped when the sensing member 79 engages at least a portion of the plunger 26, such as the plunger cover 58 (shown in FIG. 3E). The plunger 26 resists being disconnected from the piston 88 upon movement of piston 88 in a distal and proximal direction relative to the syringe barrel 18. In one aspect, the retaining members 68 may be designed such that the compressive forces exerted upon the catch 74 upon movement of piston head 92 in the proximal direction substantially prevent radially outward deflection (or bending) of the retaining members 68. For example, once the retaining members 68 are locked to the piston head 92, axial movement of the piston 88 does not introduce a bending moment sufficient to deflect the retaining members 68 radially to cause the plunger 26 to be disconnected from the piston 88. Proximal movement of the piston 88 causes the at least one retaining member 68 to be loaded in compression between the first end 70 and the second end 72 such that the retaining member 68 may be urged in a radially inward direction, thereby increasing the locking force between the plunger 26 and the piston 88.

To unlock the syringe 12 from the syringe port 16 (shown in FIG. 1) and disengage the plunger 26 from the piston 88, the syringe 12 is rotated clockwise or counter-clockwise about the syringe longitudinal axis, in a clockwise or counter-clockwise direction, relative to the syringe port 16. Because the plunger 26 is substantially free from rotation within the syringe barrel 18 due to a frictional force of the seal 59 with the inner surface 23 of the syringe sidewall 19 (shown in FIG. 2), the rotation of the syringe 12 also causes the plunger 26 to rotate relative to the piston 88. The free-rotation direction of the one-way rotation mechanism 99 is desirably opposite to the rotation direction of the syringe 12 during the release of the syringe 12 from the syringe port 16. Rotation of the syringe 12, and thereby the plunger 26, about the plunger longitudinal axis 34 engages the first cam member 78 on the plunger 26 with the actuation surface or second cam member 98 on the piston head 92. Such movement causes a radial deflection of the at least one retaining member 68 away from the piston head 92.

As the at least one retaining member 68 is deflected radially outward relative to the plunger longitudinal axis 34, the catch 74 is moved out of engagement with the locking ledge 111. In this position, the at least one retaining member 68 is in a deflected state that allows the plunger 26 to be moved axially relative to the piston 88. Such axial movement of the plunger 26 can be effected by withdrawing the syringe 12 from the syringe port 16 in a distal direction along the syringe longitudinal axis 15, by withdrawing the piston 88 in a proximal direction away from the plunger 26, or both. The plunger 26, together with the syringe 12, can then be completely disengaged from the piston 88 and the injector 10. In some aspects, the piston 88 can be released from the plunger 26 by rotating the piston 88 about its longitudinal axis and retracting the piston 88 in a proximal direction to disengage the at least one retaining member 68 in a manner described herein.

Figure 6A:
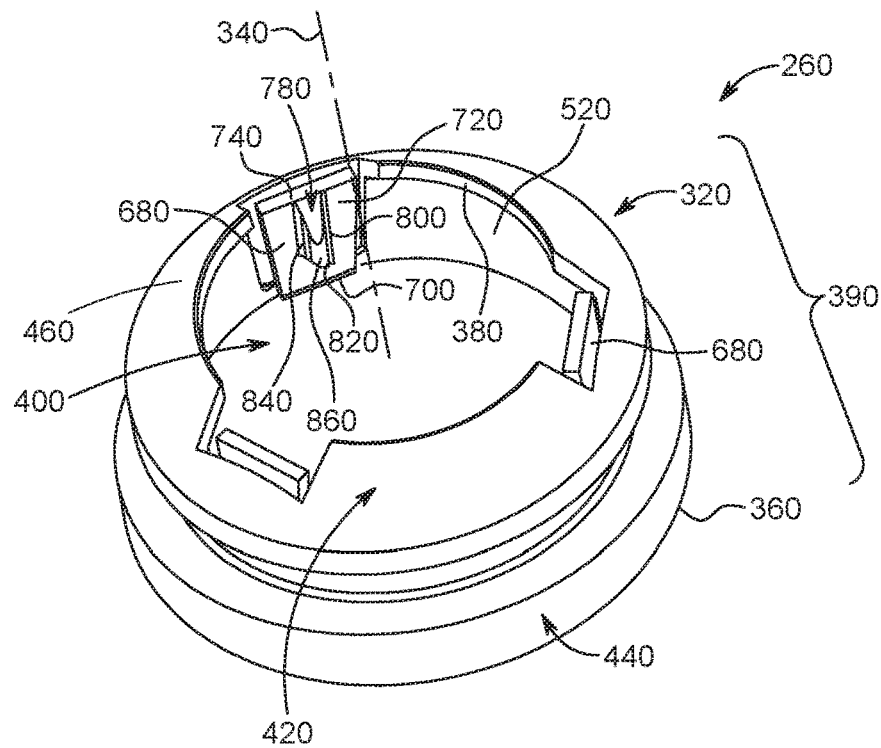
FIG. 6A is a top perspective view of a plunger according to another aspect of the present disclosure.
Figure 6B:
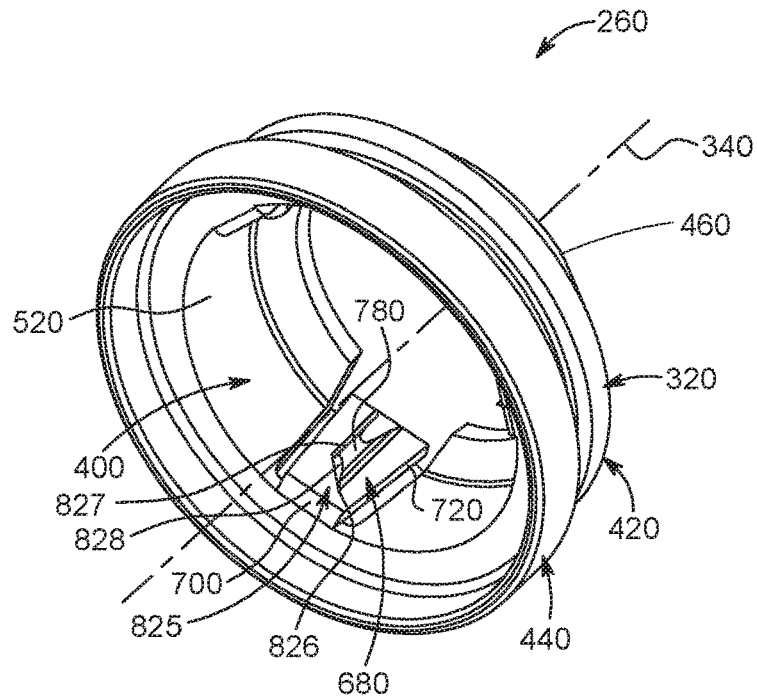
FIG. 6B is a bottom perspective view of the plunger shown in FIG. 6A.

With reference to FIGS. 6A-6B, a plunger 26 and a piston 88 are shown in accordance with another aspect of the present disclosure. The components of the plunger 26 shown in FIGS. 6A-6B are substantially similar to the components of the plunger 26 described herein with reference to FIGS. 3A-3C. As the previous discussion regarding the plunger 26 generally shown in FIGS. 3A-3C is applicable to the aspect of the present disclosure shown in FIGS. 6A-6B, only the relative differences between the plunger 26 and piston 88 generally shown in FIGS. 3A-4C and the plunger 26 and piston 88 shown in FIGS. 6A-6B are discussed hereinafter.

In one exemplary and non-limiting aspect with 6 locking ledges 111 having equal angular separation therebetween, to mate with the plunger as shown in FIG. 3C, each locking ledge 111 is separated by 60 degrees center to center from the locking ledge 111 adjacent on either side. In some aspects, the locking ledge 111 may have unequal angular extension and/or unequal angular spacing between the locking ledge 111 about the outer surface of the piston 88. In another exemplary and non-limiting aspect with two or more locking ledges 111, each retaining locking ledge 111 has a center to center separation from the locking ledge 111 adjacent on either side of an integer number of 60 degrees and furthermore each locking ledge 111 has an angular extent less than 60 degrees, for example 15 to 45 degrees. This enables the release of the plunger 26 from the piston 88 with a relative rotation of 15 to 45 degrees. Optionally the relative rotation is less than 30 degrees. The radial spacing of the at least one locking ledge 111 relative to the plunger longitudinal axis 34 is selected to correspond to or operably interact with radial spacing of the at least one plunger retaining member 68, as described herein.

With reference to FIGS. 6A-6B, a plunger 260 is shown in accordance with another aspect of the present disclosure. The barrel 18 of the syringe 12 is omitted from FIGS. 6A-6B for clarity. The plunger 260 includes a plunger body 320 defining a plunger longitudinal axis 340 and having a proximal end 360, a distal end 380, and a circumferential sidewall 390 connecting the proximal end 360 and the distal end 380. The sidewall 390 may have a uniform or non-uniform thickness between the proximal end 360 and the distal end 380. The plunger body 320 may be formed from glass, metal, or a suitable medical-grade plastic.

With continued reference to FIGS. 6A-6B, the plunger body 320 has an interior cavity 400 with a conical-shaped portion 420 at the distal end 380 of the plunger body 320 and a cylindrical-shaped portion 440 at the proximal end 360 of the plunger body 320. The conical-shaped portion 420 may be monolithically formed with the cylindrical-shaped portion 440. In some aspects, the conical-shaped portion 420 may be affixed or otherwise secured to the cylindrical-shaped portion 440 of the plunger body 320 using, for example, a frictional fit and/or an adhesive, welding, or by molding. The conical-shaped portion 420 may have a truncated end 460 that has a central opening 480. In some aspects, the distal end 380 of the plunger body 320 may be enclosed. In some aspects, the plunger 260 may have a plunger cover, such as the plunger cover 58 shown in FIG. 2, configured for covering at least a portion of an outer surface of the plunger body 320.

With continued reference to FIGS. 6A-6B, the plunger 260 may have at least one resiliently deflectable retaining member 680 (hereinafter "retaining member 680") protruding from the plunger body 320 in a distal direction. In some aspects, the at least one retaining member 680 may protrude distally and radially inward from an inner surface 520 of the interior cavity 400 of the plunger body 320. The at least one retaining member 680 has a first segment or a first end 700 connected to the plunger body 320 and a second segment or a second end 720 radially deflectable relative to the first end 700. As described herein, the second end 720 may be radially deflectable relative to the first end 700 when the at least one retaining member 680 engages a piston of the fluid injector 10 (shown in FIG. 1). The first end 700 and the second end 720 may be spaced apart in a direction that extends substantially along a direction of the plunger longitudinal axis 340 of the plunger 260. The at least one retaining member 680 may be linearly or curvilinearly contiguous between the first end 700 and the second end 720.

In some aspects, a plurality of retaining members 680 are spaced apart radially from the plunger longitudinal axis 340 along a circumference of the inner surface 520 of the interior cavity 400. In such aspects, the retaining members 680 are separated from each other by portions of the inner surface 520 of the interior cavity 400. In aspects where more than one retaining member 680 is provided, the retaining members 680 may be evenly spaced apart from each other. In one exemplary and non-limiting aspect with three retaining members 680 having equal angular separation therebetween, a center of each retaining member 680 is separated by 120 degrees from a center of the retaining members 680 adjacent on either side. In another exemplary and non-limiting aspect with six retaining members 680 having equal angular separation therebetween, a center of each retaining member 680 is separated by 60 degrees from a center of the retaining members 680 adjacent on either side. In some aspects, the retaining members 680 may have unequal angular extension and/or unequal angular spacing between the retaining members 680 about the inner surface 520 of the interior cavity 400. The radial spacing of the at least one retaining member 680 relative to the plunger longitudinal axis 340 is selected to correspond to features on an outer circumference of the piston, as described herein.

In some aspects, one or more retaining members 680 may be parallel with the longitudinal axis 340. In other aspects, one or more retaining members 680 may be angled relative to the longitudinal axis 340. For example, one or more retaining members 680 may be angled inward toward the longitudinal axis 340 in a direction from the first end 700 toward the second end 720.

With continued reference to FIGS. 6A-6B, the second end 720 of the retaining member 680 has at least one catch 740. The at least one catch 740 may be a terminal surface of the second end 720 of the retaining member 680. In some aspects, the at least one catch 740 may protrude radially from the retaining member 680. For example, the at least one catch 740 may protrude radially inward toward the plunger longitudinal axis 340 of the plunger body 320, or radially outward away from the plunger longitudinal axis 340. As described herein, the at least one catch 740 is shaped to engage at least a portion of a recess on the piston to releasably lock the at least one retaining member 680 relative to the piston. The at least one catch 740 may be formed integrally with the second end 720 of the at least one retaining member 680 or it may be affixed or otherwise secured to the second end 720 of the at least one retaining member 680 using, for example, a frictional fit and/or an adhesive, welding, or by molding. In other aspects, the at least one catch 740 may be formed on the second end 720 of the at least one retaining member 680 by etching, laser cutting, or machining.

With continued reference to FIGS. 6A-6B, the plunger 260 may have at least one first cam member 780 disposed between the first end 700 and the second end 720 of the retaining member 680. The at least one first cam member 780 is configured to interact with a piston of the fluid injector 10 (shown in FIG. 1) to radially deflect the at least one retaining member 680 upon rotation of the plunger 260 relative to the piston, as described herein. The position of the at least one first cam member 780 between the first end 700 and the second end 720 of the retaining member 680 allows for a greater radial deflection of the at least one first cam member 780 upon relative rotation between the plunger 260 and the piston 880 (shown in FIGS. 7A-7B) compared to providing the at least one first cam member 780 at the second end 720. The at least one first cam member 780 may be parallel with a surface of the retaining member 680. In some aspects, the at least one cam member 780 may be angled relative to a surface of the retaining member 680.

In some aspects, the at least one first cam member 780 protrudes radially inward toward the plunger longitudinal axis 340 of the plunger body 320. In other aspects, the at least one first cam member 780 protrudes radially outward relative to the plunger longitudinal axis 340 of the plunger body 320. The position of the at least one first cam member 780 between the first end 700 and the second end 720 of the retaining member 680 may minimize the radial protrusion of the at least one first cam member 780 while still allowing a full radial deflection of the at least one retaining member 680 upon rotation of the plunger 260 relative to the piston 880, as described herein. In some aspects, the at least one first cam member 780 may be provided on at least a portion of the at least one catch 740. A plurality of first cam members 780 may be axially spaced apart along a length of the retaining member 680 between the first end 700 and the second end 720. The at least one first cam member 780 may be formed integrally with the at least one retaining member 680 or it may be affixed or otherwise secured to the at least one retaining member 680 using, for example, a frictional fit and/or an adhesive, welding, or by molding. In other aspects, the at least one first cam member 780 may be formed on the at least one retaining member 680 by etching, laser cutting, or machining.

With reference to FIG. 6A, the at least one first cam member 780 may have at least one tooth 800 configured to engage a corresponding groove on the piston. The at least one tooth 800 on the at least one first cam member 780 is desirably shaped to generally correspond to the corresponding groove on the piston. Each tooth 800 may have a peak 820 leading to a groove 840 for example along a gear surface 860. The at least one tooth 800 on the at least one first cam member 780 may be the shape of a gear tooth having a spur gear profile or a helical gear profile. While FIGS. 6A-6B illustrate one non-limiting aspect of the at least one first cam member 780, various other shapes are also contemplated. For example, the at least one first cam member 780 of the at least one retaining member 680 may have a generally circular, triangular, square, rectangular, or any suitable polygonal shape or cross-section. In each aspect, the at least first cam member 780 is configured for engaging at least a portion of the piston to cause the at least one retaining member 680 to be deflected from the piston upon rotation of the plunger 260 relative to the piston. In general, the at least one first cam member 780 may have at least one corrugated, rippled, or multilevel surface, either in singular or regularly or irregularly repeating form, that is configured for engaging with the corresponding cam member on the piston of the fluid injector.

With continued reference to FIGS. 6A-6B, the plunger 260 may have at least one first alignment member 825 disposed between the first end 700 and the second end 720 of the retaining member 680. The first alignment member 825 has a proximal edge or tip 826, a distal edge 827, and a proximal alignment surface 828. The first alignment member 825 cooperates with a second alignment member 1010 (shown in FIG. 7A) on the piston head 920 to rotationally guide, self-align, move, or drive the plunger 260 and piston 880 into the proper rotational alignment for attachment or engagement and for subsequent detachment. The proximal alignment surface 828 may be a continuous surface or may be multiple discrete surfaces which act to provide continuous alignment activation when cooperating with the second alignment member 925 of the piston head 920 during plunger to piston engagement. A first alignment member 825 may optionally be on the retaining member 680, may be part of the first cam member 780, and/or may be rigidly associated with another aspect of the plunger 260.

Figure 7A:
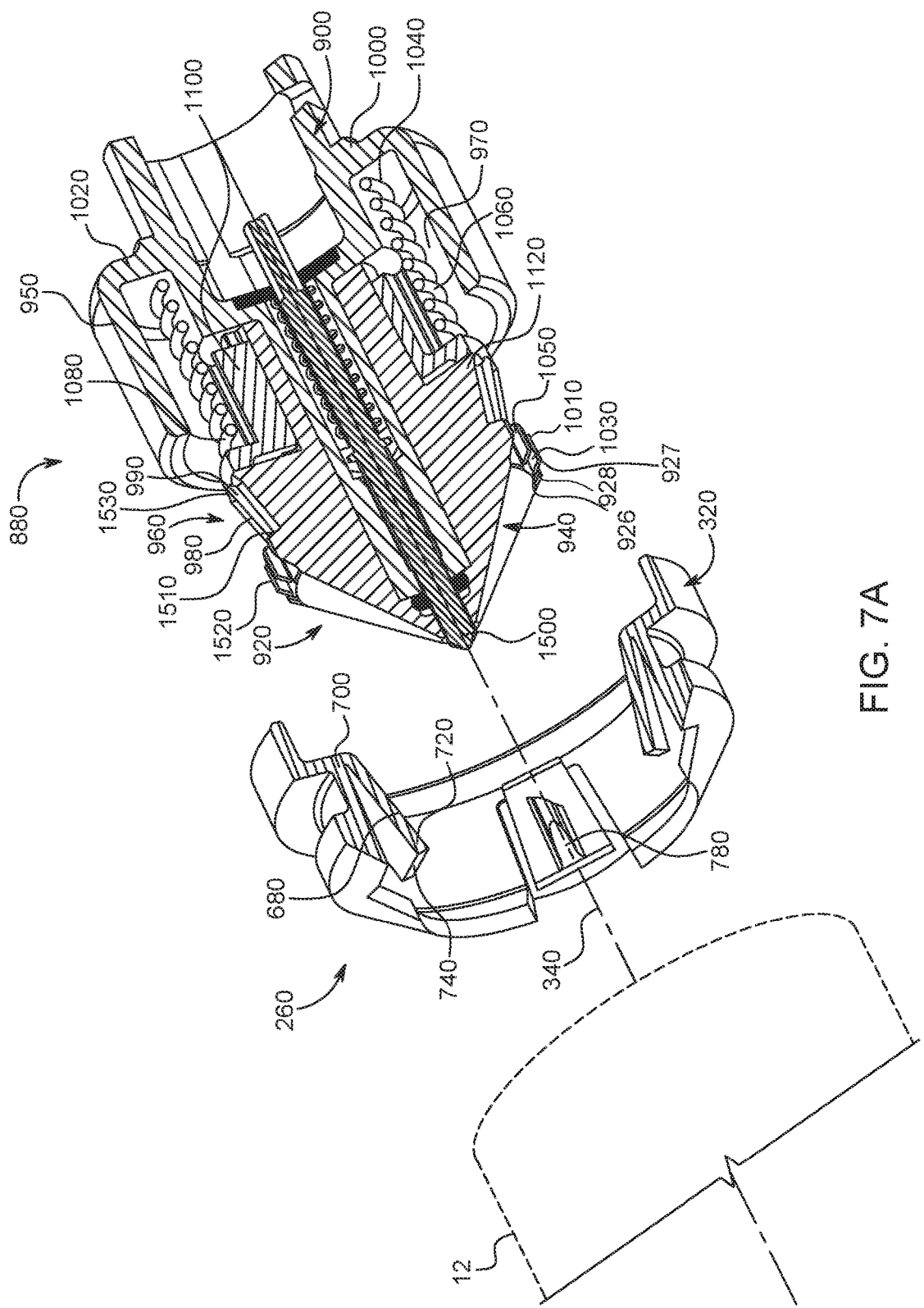
FIG. 7A is a perspective cross-sectional view of the plunger shown in FIGS. 6A-6B and a piston prior to initial engagement of the piston with the plunger.

Referring to FIG. 7A, a piston 880 is extendible and retractable from the housing 14 of the fluid injector 10 (shown in FIG. 1) via a powered means (not shown) preferably contained within housing 14. The powered means may include, for example, an electric motor, a hydraulic system, or a pneumatic system, including appropriate gearing (not shown). As known in the art, the fluid injector 10 also may include a controller for controlling operation of the powered means and thereby controlling operation of the piston 880.

With continued reference to FIG. 7A, the piston 880 includes a stem 900 and a piston head 920 formed on a distal end of the stem 900. The piston 880 is construed from a relatively rigid material, such as metal or plastic that resists deformation due to repeated engagement with and disengagement from the plunger 260. The piston head 920 has a substantially cylindrical structure with a pointed or conical distal end 940 that is configured to be received inside at least a portion of the interior cavity 400 of the plunger 260. In some aspects, a sensing member 1500, such as a spring-loaded pin connected to a sensor, may be provided. The sensing member 1500 may extend along a longitudinal axis of the piston 880 and may protrude through at least a portion of the piston head 920. The sensing member 1500 may be operative for sensing contact with a surface, such as a surface of the plunger 260 and/or the plunger cover 58 (shown in FIG. 3E), and control a movement of the piston 880 based on the sensed condition. For example, an initial contact between the sensing member 1500 and the plunger 260 and/or the plunger cover 58 may cause the pin to be retracted in a proximal direction such that it makes contact with the sensor. The sensor may be connected to the drive mechanism of the piston 880 such that, upon activation of the sensor by the pin, the sensor controls the movement of the drive mechanism. For example, the drive mechanism may be stopped or slowed from a first rate to a second, slower rate.

The proximal end 960 of the piston head 920 has an actuation member that interacts with the actuation member on the plunger 260, such as the first cam member 780. In some aspects, the actuation member on the piston head 920 may be a second cam member 980. In some aspects, the second cam member 980 is a tooth of a gear 990 that extends around at least a portion of an outer circumference of the piston head 920. The second cam member 980 is configured for cooperation with the first cam member 780 on the at least one retaining member 680 of the plunger 260, as described herein. The second cam member 980 desirably has a shape that, upon self-aligning, relative rotation between the piston 880 and the plunger 260, engages the first cam member 780 to cause the at least one retaining member 680 to be deflected from the piston head 920 such that the plunger 260 can be removed from the piston 880.

In some aspects, the second cam member 980 may be parallel with the longitudinal axis 340. In other aspects, the second cam member 980 may be angled relative to the longitudinal axis 340. For example, the second cam member 980 may be angled toward the longitudinal axis 340 at an angle corresponding to an angle of inclination of the at least one retaining member 680. In various aspects, regardless of the angular orientation of the at least one retaining member 680, the first cam member 780 is desirably parallel with the second cam member 980.

Figure 7B:
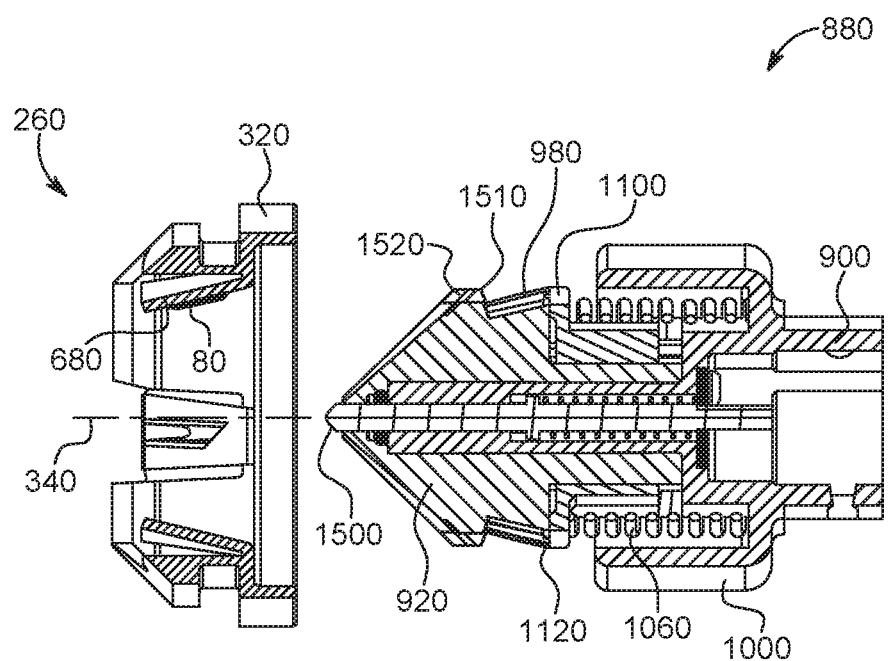
FIG. 7B is a side cross-sectional view of the plunger and the piston shown in FIG. 7A.

With continued reference to FIGS. 7A-7B, the piston head 920 may have a second alignment member 1010 to interact with the first alignment member 825 (shown in FIG. 6B) on the plunger 260. The alignment member 1010 has a first edge 927 and a second edge 926, and a surface 928 between the first edge 927 and the second edge 926. The longitudinal, radial, and circumferential locations of the first edge 927 and the second edge 926 and contour and extent of surface 928 of the second alignment member 1010 are chosen to interact with the edges and surfaces of the first alignment member 825 to provide a rotational force and motion as the piston 880 and plunger 260 are axially moved together. The piston head 920, and optionally the collar 950, may be connected to the piston stem 900 via a one-way rotation mechanism, such as the one-way rotation mechanism 99 discussed herein with reference to FIG. 4B, so that the piston 880 and the plunger 260 can rotate into alignment in response to the interaction of the first and second alignment surfaces. Alternatively, if the amount of rotation is small enough, the elasticity or slip of the plunger cover (shown in FIG. 3E) with respect to the syringe barrel may be sufficient to allow the plunger 260 to rotate into alignment with the piston head 920.

With continued reference to FIGS. 7A-7B, the piston 880 may have a collar 950 surrounding at least a portion of the stem 900 and/or the piston head 920. The collar 950 may protrude radially outward relative to an outer radial surface of the stem 900 and the piston head 920 such that an annular space 970 is defined between the piston 880 and the collar 950. The collar 950 may have an open top end and a closed bottom end that is defined by a bottom sidewall 1000 that connects the collar 950 to the stem 900 and/or the piston head 920. The bottom sidewall 1000 defines a seat 1020 for a first end 1040 of a resiliently elastic member, such as a spring 1060, that surrounds the stem 900. In other aspects, the seat 1020 may be provided as a radial flange that protrudes from an outer surface of the stem 900. The second end 1080 of the spring 1060 engages a proximal end of a movable capture ring 1100. The capture ring 1100 has a substantially annular shape and surrounds at least a portion of an outer circumference of the stem 900. In some aspects, at least a portion of an outer diameter of the capture ring 1100 may have a same or larger outer diameter than an outer diameter of the piston head 920. The spring 1060 biases the capture ring 1100 toward a first radial lip 1120 of the piston head 920. The capture ring 1100 is movable axially between a first position, where the capture ring 1100 engages the first radial lip 1120 of the piston head 920, and a second position, where the spring 1060 is compressed and the capture ring 1100 is deflected by at least a portion of the at least one retaining member 680 toward the bottom sidewall 1000 of the collar 950. In some aspects, the capture ring 1100 may be movable between the first position and the second position when urged by contact with, for example, the first end 700 of the at least one retaining member 680. A stop member (not shown) may be provided to limit the movement of the capture ring 1100 to the second position. During disengagement of the plunger 260 from the piston 880, the capture ring 1100 urges the at least one retaining member 680 in a distal direction due to a restoring force of the spring 1060. In some aspects, the capture ring 1100 may have a grooved radial edge 1530 configured to engage the first cam member 780 of the at least one retaining member 680.

With continued reference to FIGS. 7A-7B, the piston head 920 further defines a second radial lip 1510 at a distal end of the at least one second cam member 980. When the plunger 260 is engaged with the piston 880, the second radial lip 1510 acts as a retention surface for the at least one catch 740 of the at least one retaining member 680. The piston head 920 may further have guiding grooves 1520 provided distally from the second radial lip 1510. In some aspects, the guiding grooves 1520 may have a shape that corresponds to the shape of the first cam member 780. In this manner, the tooth 800 of the first cam member 780 may be guided into the guiding groove 1520 as the plunger 260 and the piston head 920 are moved toward each other.

Having described the structure of the plunger 260 and the piston 880 in accordance with one non-limiting aspect of the present disclosure, the engagement and disengagement of the plunger 260 with and from the piston 880 will now be described with reference to FIGS. 7A-12B. The syringe 12, shown initially in phantom in FIG. 7A is omitted from the remainder of FIGS. 7B-12B for clarity.

To engage the plunger 260 with the piston 880, the syringe 12 is first inserted into the syringe port 16 of the fluid injector 10, as described herein. Once the syringe 12 is inserted into the syringe port 16, various locking mechanisms (not shown) may be used to releasably retain the syringe 12 within the syringe port 16 to prevent detachment of the syringe 12 from the syringe port 16. Initially, the plunger 260 may be positioned at the proximal end 20 of the syringe barrel 18. In some aspects, the plunger 260 is positioned at any axial location between the proximal end 20 and the distal end 24 of the syringe barrel 18. The piston 880 may then be advanced distally toward the plunger 260 for engagement of the piston head 920 with the plunger 260. In some aspects, the piston 880 may be advanced distally toward the plunger 260 by way of the powered means operated by a controller. In other aspects, the piston 880 may be advanced distally toward the plunger 260 by manual operation.

Figure 8A:
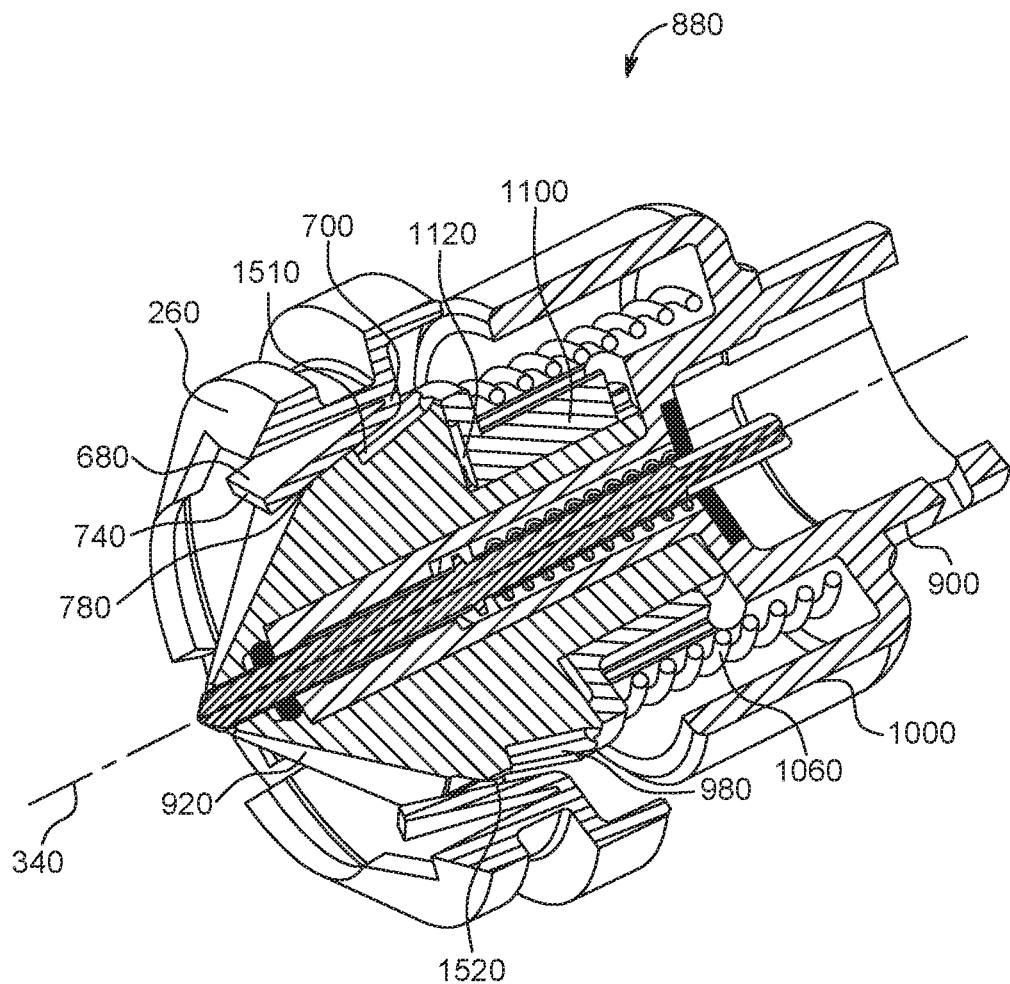
FIG. 8A is a perspective cross-sectional view of the plunger and the piston during initial engagement of the piston with the plunger.
Figure 8B:
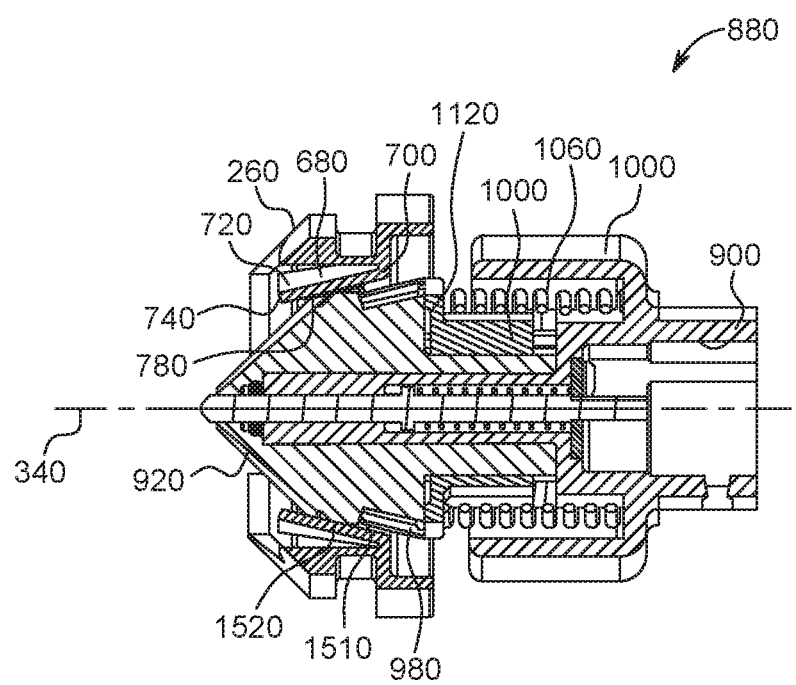
FIG. 8B is a side partial cross-sectional view of the plunger and the piston shown in FIG. 8A.

With reference to FIGS. 8A-8B, the piston 880 is advanced axially in a distal direction such that at least a portion of the pointed or conical distal end 940 of the piston head 920 contacts the at least one retaining member 680 of the plunger 260. Initially, at least a portion of the piston head 920, such as the guiding grooves 1520, contacts the first alignment member 825 (shown in FIG. 6B), for example, on the at least one retaining member 680. The piston head 920 may be connected to the piston stem 900 via a one-way rotation mechanism, such as the one-way rotation mechanism 99 discussed herein with reference to FIG. 4B, so that the piston 880 and the plunger 260 can rotate into self-alignment in response to the interaction of the first and second alignment surfaces. Alternatively, if the amount of rotation is small enough, the elasticity or slip of the plunger cover (shown in FIG. 3E) with respect to the syringe barrel may be sufficient to allow the plunger 260 to rotate into alignment with the piston head 920.

Due to an angled orientation of the at least one retaining member 680 relative to the longitudinal axis, continued axial movement of the piston head 920 relative to the plunger 260 causes the at least one retaining member 680 to be deflected radially outward due to the contact between the at least one retaining member 680 and the outer surface of the piston head 920. In an aspect having a plurality of retaining members 680, each of the retaining members 680 may be deflected radially outward relative to the piston head 920.

Figure 9A:
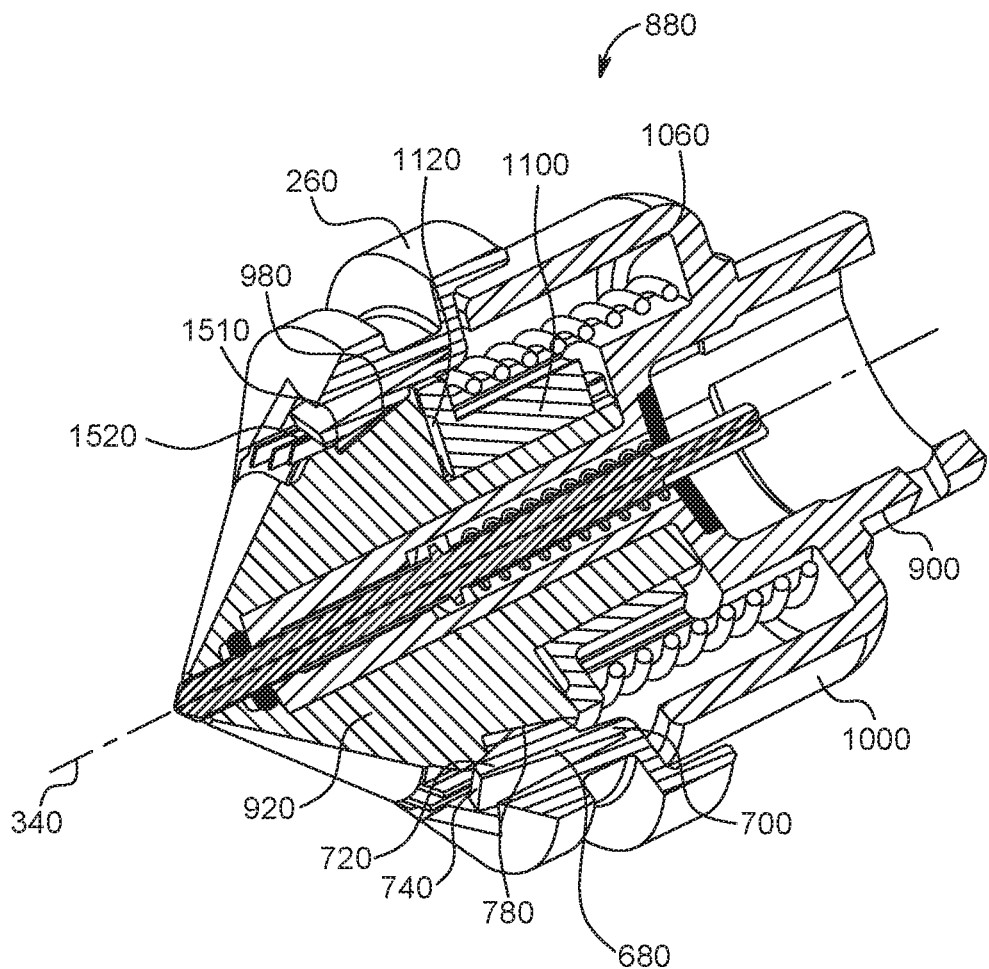
FIG. 9A is a perspective cross-sectional view of the plunger and the piston prior to full engagement of the piston with the plunger.
Figure 9B:
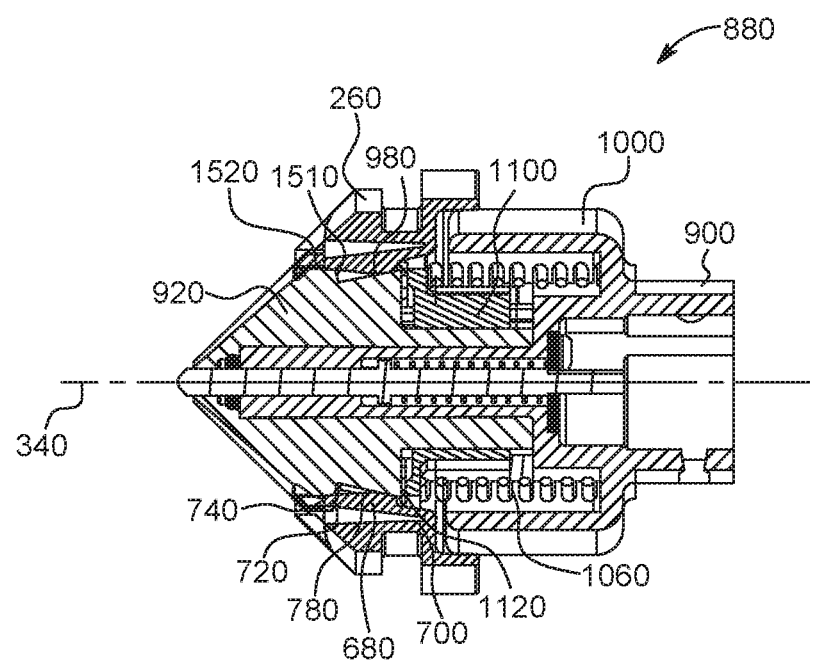
FIG. 9B is a side cross-sectional view of the plunger and the piston shown in FIG. 9A.

With reference to FIGS. 9A-9B, during continued axial movement of the piston 880 in a distal direction, at least a portion of the retaining member 680 engages the distal end of the capture ring 1100. For example, the first end 720 and/or the first cam member 780 of the retaining member 680 may engage the distal end of the capture ring 1100. The contact between at least a portion of the retaining member 680 and the distal end of the capture ring 1100 urges the capture ring 1100 against the restoring force of the spring 1060 and away from the first radial lip 1120 of the piston head 920.

Figure 10A:
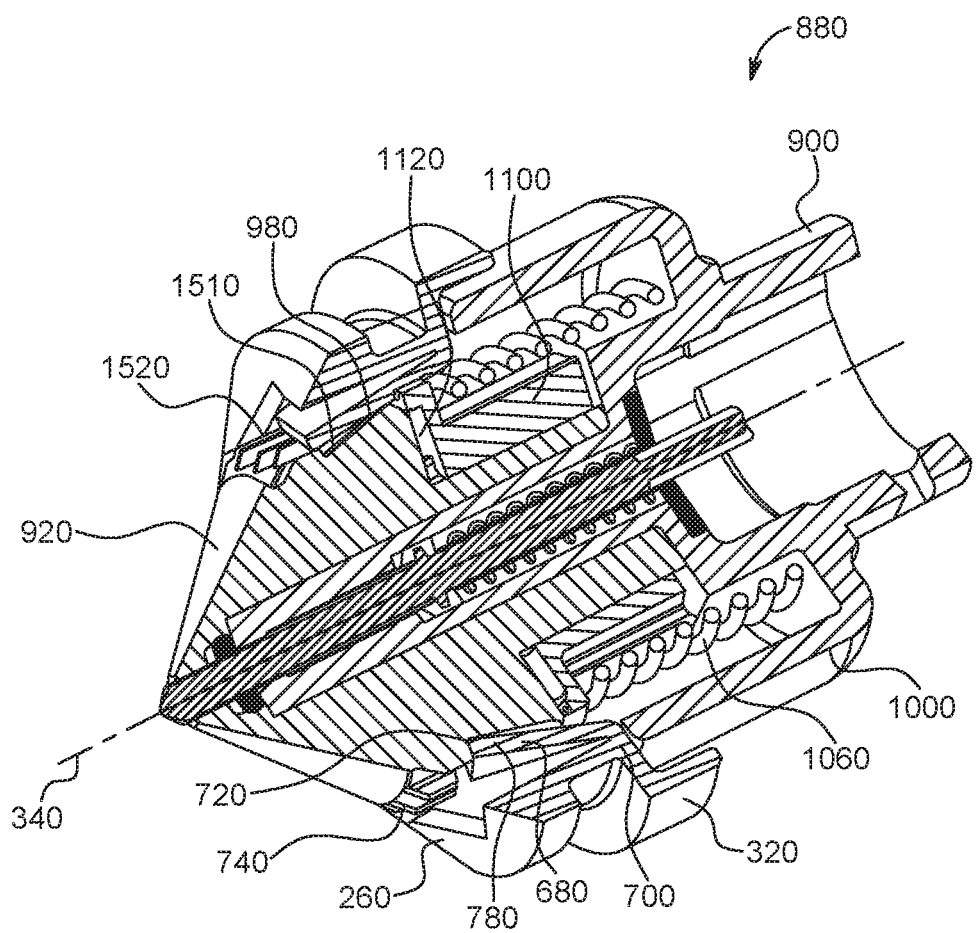
FIG. 10A is a perspective cross-sectional view of the plunger and the piston during full engagement of the piston with the plunger.
Figure 10B:
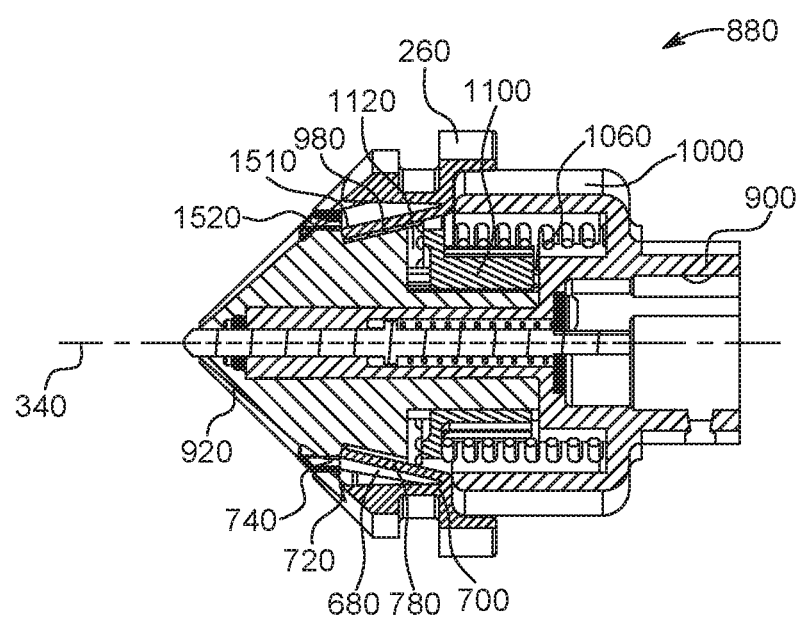
FIG. 10B is a side cross-sectional view of the plunger and the piston shown in FIG. 10A.

With reference to FIGS. 10A-10B, at least a portion of the retaining member 680, such as the first end 720 and/or the first cam member 780 of the retaining member 680, urges the capture ring 1100 proximally against the restoring force of the spring 1060. The body of the at least one retaining member 680 has an inherent restoring force built up in the material of the at least one retaining member 680 when the at least one retaining member 680 is deflected from its natural, undeflected state to a radially deflected state. Due to this inherent restoring force created within the body of the at least one retaining member 680 during a radial deflection of the at least one retaining member 680, the second end 720 and/or the catch 740 is snapped radially into the second radial lip 1510. Such radial movement of the second end 720 and/or the catch 740 also or further engages the first cam member 780 on the plunger 260 with the second cam member 980 on the piston head 920. Specifically, the peaks 820 of the first cam member 780 are received in the groove 1030 of the second cam member 980, and the groove 840 of the first cam member 780 receives the peaks 1010 of the second cam member 980 (shown in FIGS. 6A and 7A). In this manner, the gear surface 860 of the first cam member 780 is engaged with the gear surface 1050 of the second cam member 980. The capture ring 1100 maintains contact with at least portion of the retaining member 680 to urge the second end 720 and/or the catch 740 into contact with the second radial lip 1510. After retention of the plunger 260 on the piston head 920 by the engagement of the second end 720 and/or the catch 740 in the second radial lip 1510 of the piston head 920, the plunger 260 resists being disconnected from the piston 880 upon movement of piston 880 in a distal and proximal direction relative to the syringe barrel 18. In one aspect, the second end 720 and/or the catch 740 may be designed such that the compressive forces exerted upon the second end 720 and/or the catch 740 upon movement of piston 880 in the proximal direction substantially prevents radially outward deflection (or bending) of the catch 740. For example, once the catch 740 is engaged, axial movement of the piston 880 does not introduce a bending moment which may deflect the catch 740 radially to cause the plunger 260 to be disconnected from the piston 880.

Figure 11A:
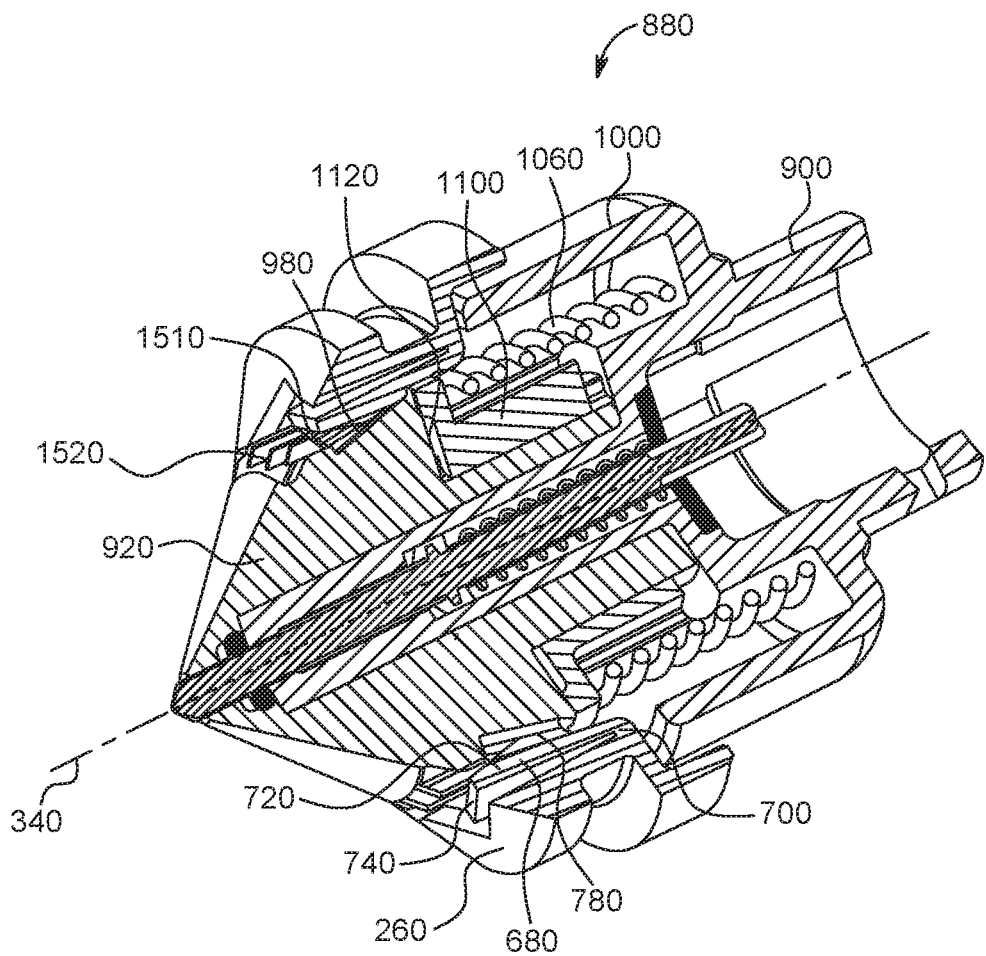
FIG. 11A is a perspective cross-sectional view of the plunger and the piston during initial disengagement as the plunger is rotated relative to the piston.
Figure 11B:
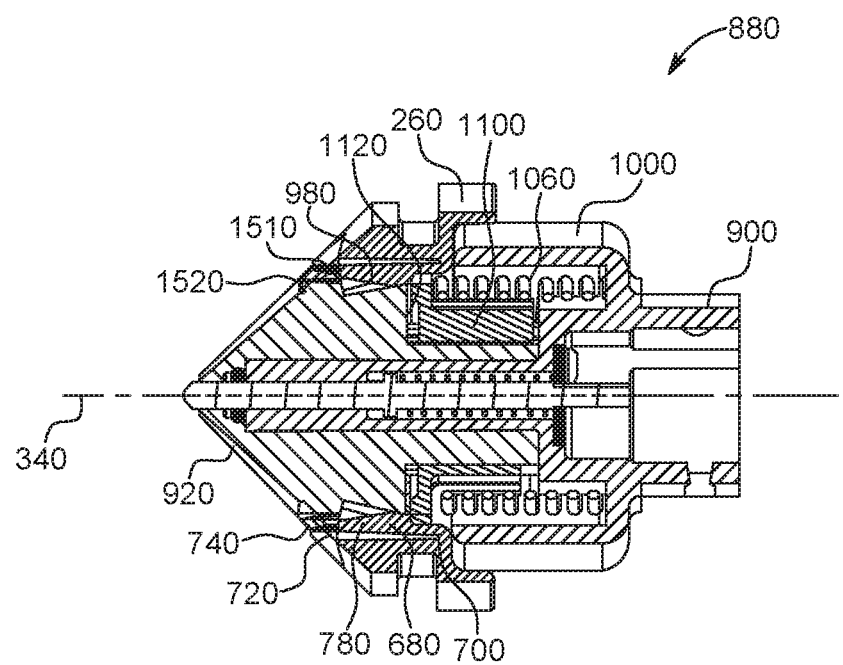
FIG. 11B is a side cross-sectional view of the plunger and the piston shown in FIG. 11A.

To unlock the syringe 12 from the syringe port 16 (shown in FIG. 1) and disengage the plunger 260 from the piston 880, the syringe 12 is rotated clockwise or counter-clockwise about the syringe longitudinal axis, in a clockwise or counter-clockwise direction, relative to the syringe port 16. Because the plunger 260 is substantially free from rotation within the syringe barrel 18 due to a frictional force between plunger seal 59 and the inner surface 23 of the syringe sidewall 19, the rotation of the syringe 12 also causes the plunger 260 to rotate relative to the piston 880. With reference to FIGS. 11A-11B, rotation of the plunger 260 about its longitudinal axis 340 engages the first cam member 780 on the plunger 260 with the second cam member 980 on the piston head 920. In particular, rotational movement of the plunger 260 causes the gear surface 860 of the first cam member 780 to move along the gear surface 1050 of the second cam member 980 such that the peaks 820 of the first cam member 780 are moved out of the grooves 101 of the second cam member 980 and toward the peaks 1010 of the second cam member 980. Such movement causes a radial deflection of the at least one retaining member 680 away from the piston head 920. The at least one retaining member 680 is at its maximum radial deflection when the peaks 820 of the first cam member 780 on the plunger 260 are positioned over or aligned with the peaks 1010 of the second cam member 980 on the piston head 920.

Figure 12A:
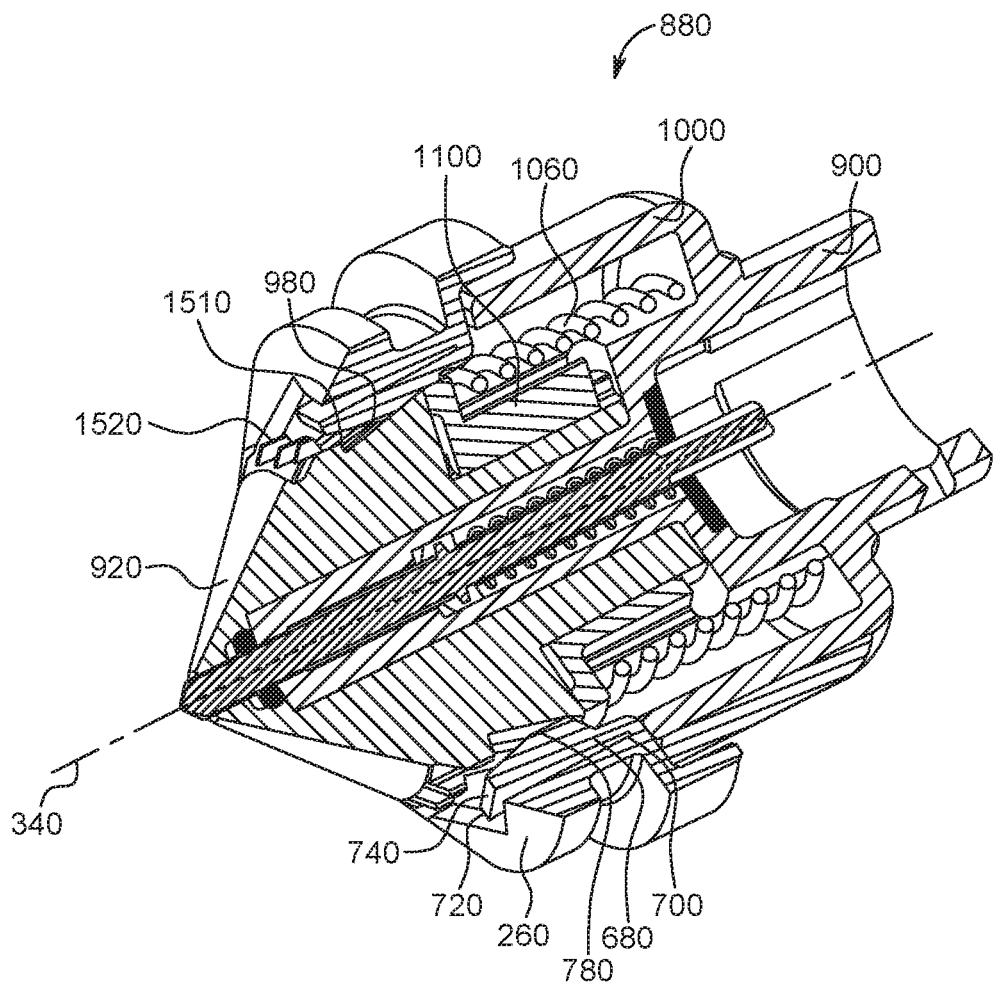
FIG. 12A is a perspective cross-sectional view of the plunger and the piston during disengagement with a locking ring of the piston in a forward position.
Figure 12B:
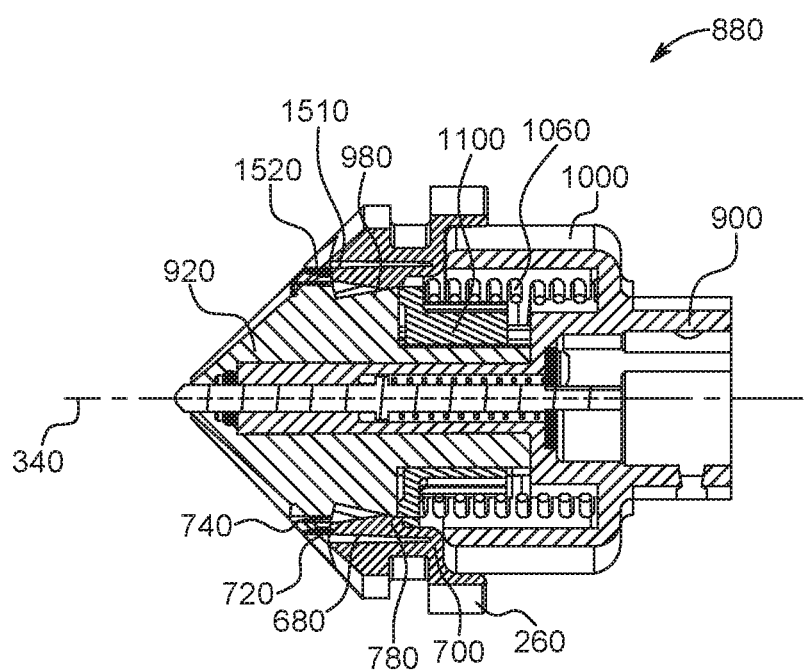
FIG. 12B is a side cross-sectional view of the plunger and the piston shown in FIG. 12A.

As the at least one retaining member 680 is deflected radially outward relative to the plunger longitudinal axis 340, the second end 720 and/or the catch 740 is moved from the second radial lip 1510 of the piston head 920. As the catch 740 moves out of its engaged position, the capture ring 1100 is advanced in the distal direction under the restoring force of the spring 1060. As shown in FIGS. 12A-12B, the distal movement of the capture ring 1100 causes the capture ring 1100 to maintain the position of the at least one retaining member 680 in the radially outward deflected position, for example by moving under at least a segment of the at least one first cam member 780 or another part of the at least one retaining member 680. In this position, the at least one retaining member 680 is held in a deflected state that allows the plunger 260 to be moved axially relative to the piston 880. Such axial movement of the plunger 260 can be effected by withdrawing the syringe 12 from the syringe port 16 in a distal direction along the syringe longitudinal axis 15 or by withdrawing the piston 880 in a proximal direction away from the plunger 260. The plunger 260, together with the syringe 12, can then be completely disengaged from the piston 880 and the injector 10. In some aspects, the piston 880 can be released from the plunger 260 by rotating the piston 880 about its longitudinal axis and retracting the piston 880 in a proximal direction to disengage the at least one retaining member 680 in a manner described herein.

Figure 13:
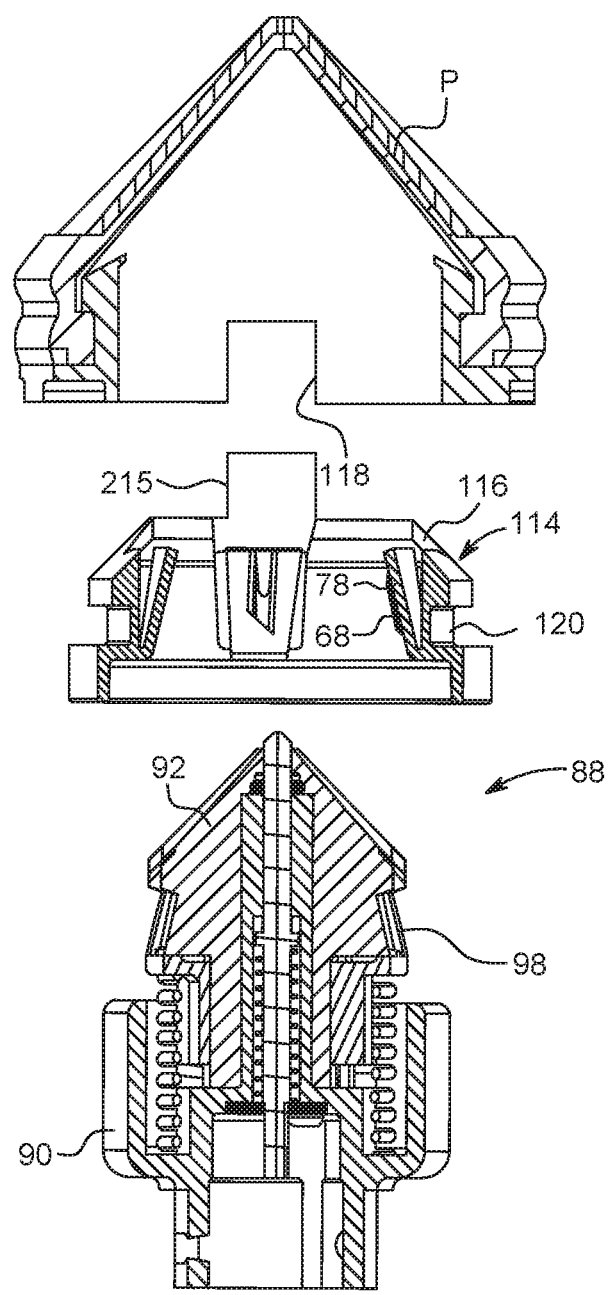
FIG. 13 is a side cross-sectional view of a first adapter configured for connecting a non-compatible plunger with a piston in accordance with one aspect of the present disclosure.

With reference to FIG. 13, a first adapter 114 may connect with a non-compatible plunger P without the at least one retaining member 68 described herein for removably engaging with the piston 88 of an injector having the piston head 92 with the second cam member 98 in accordance with one of the aspects described herein. In various aspects, the first adapter 114 may be connected to the plunger P for subsequent engagement with the piston 88. For example, the first adapter 114 may be connected to the non-compatible plunger P releasably or permanently. Such a first adapter 114 may have a connection interface having at least one retaining member 68 with the first cam member 78 in accordance with various aspects described herein. According to another aspect, first adapter 114 may releasably connect with an injector having the piston 88 described herein. The first adapter 114 and the plunger P may be connected prior to connecting to the piston 88, or the first adapter 114 may be connected to the piston 88 before the plunger P is connected to the first adapter 114. The first adapter 114 and plunger P may be removed from the piston 88 after use, with the first adapter 114 being disposed of with the plunger P, or being removed from the used plunger P and saved for subsequent use with a different plunger P. Alternatively, the first adapter 114 may be reversibly or non-reversibly connected to piston 88 for use with multiple syringes.

In one aspect, a first portion 116 of the first adapter 114 may permanently or releasably receive the plunger P, which is not compatible for use with the piston 88 described herein. The first adapter 114 allows a connection mechanism 118 of the non-compatible plunger P to engage a corresponding attachment mechanism 215 on the first adapter 114 such that the plunger P can be retained on the first adapter 114. In some aspects, the first adapter 114 may have a separate mechanism for engaging and disengaging the plunger P while the first adapter 114 remains connected to the piston 88. A second portion 120 of the first adapter 114 may have at least one retaining member 68 in accordance with any of the aspects described herein. In some aspects, the first adapter 114 may have at least one retaining member 68 may have an actuation member, such as a first cam member 78 described herein with reference to FIGS. 3A-3B; the first cam member 780 described herein with reference to FIGS. 6A-12B; the first cam member 78 shown in FIGS. 15A-G; the first cam member 78 shown in FIGS. 20A-D; the first cam member 78 shown in FIGS. 21A-C; the first cam member 78 shown in FIGS. 22A-D; the first cam member 78 shown in FIGS. 23A-D; and/or the first cam member 78 shown in FIGS. 24A-C. The second portion 120 of the first adapter 114 may releasably connect to an injector having the piston 88 with the piston head 92 according to any of the aspects described herein. In this manner, various non-compatible plungers P may be used. The first adapter 114 may non-permanently, permanently, or semi-permanently connect to an injector having the piston 88 with the piston head 92 described herein and allowing plungers P having alternate connection mechanisms to be used with the injector.

Figure 14:
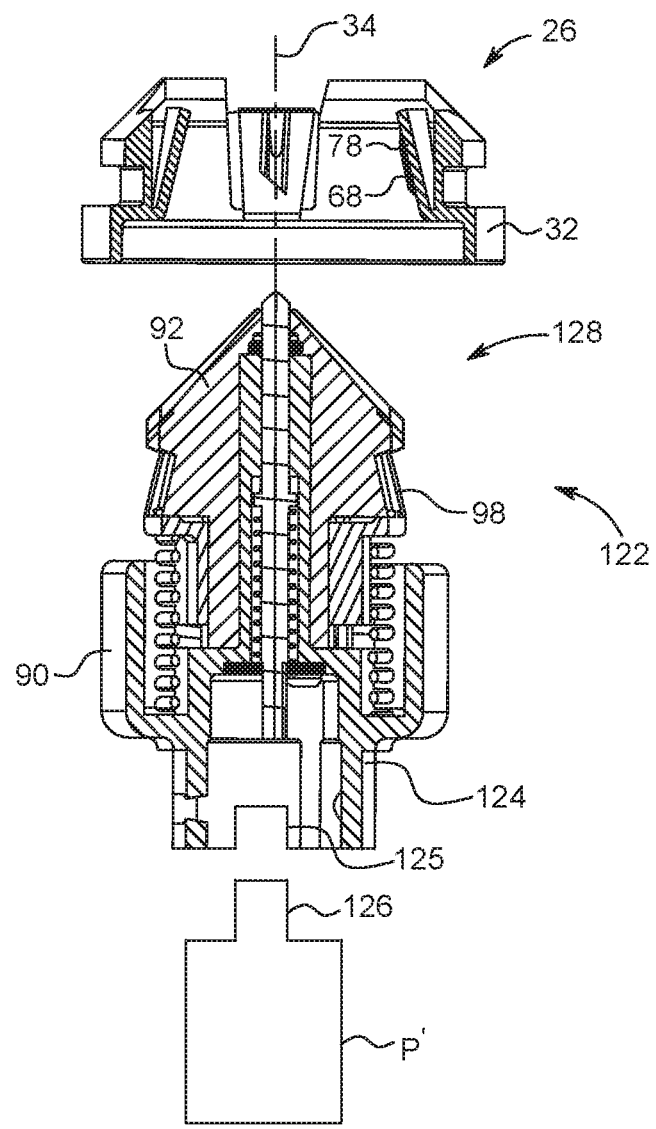
FIG. 14 is a side cross-sectional view of a second adapter configured for connecting a plunger with a non-compatible piston in accordance with one aspect of the present disclosure.

With reference to FIG. 14, a second adapter 122 may connect the plunger 26 with an injector that does not have the piston 88 with the piston head 92 according to any of the aspects described herein. In various aspects, the second adapter 122 may connect to the plunger 26 having at least one retaining member 68 in accordance with any of the aspects described herein for subsequent engagement with a non-compatible piston P'. For example, the second adapter 122 may be connected to the plunger 26 releasably or permanently. Such a second adapter 122 may have a connection interface having features of the piston head 92 in accordance with various aspects described herein. The second adapter 122 and the plunger 26 may be connected prior to connecting to the piston P', or the second adapter 122 may be connected to the piston P' before the plunger 26 is connected to the second adapter 122. The second adapter 122 and plunger 26 may be removed from the piston P' after use, with the second adapter 122 being disposed of with the plunger 26, or being removed from the used plunger 26 and saved for subsequent use with a different plunger 26.

In one aspect, a first portion 124 of the second adapter 122 may be configured for permanently or releasably engaging the plunger 26 which is not compatible for use with the piston P'. The second adapter 122 allows a connection mechanism 126 of the non-compatible piston P' to engage a corresponding connection mechanism 125 on the second adapter 122. A second portion 128 of the second adapter 122 may have features of the piston head 92 in accordance with aspects described herein. In some aspects, the second portion 128 may have the second cam member 98 described herein with reference to FIGS. 4A, 15A, 20A and/or 24A and/or the second cam member 980 described herein with reference to FIG. 7A. The second portion 128 of the second adapter 122 may releasably connect to the plunger 26 described herein. In this manner, the plunger 26 may be connected to various non-compatible injectors using the second adapter 122.

Referring to FIGS. 15A-15G, a piston 88 and a plunger 26 are shown in accordance with another aspect. The piston 88 is configured to interact with the plunger 26 (shown in FIG. 15C) to releasably lock the plunger 26 such that the plunger 26 can be driven reciprocally within the barrel of the syringe 12 (shown in FIG. 2).

Figure 15A:
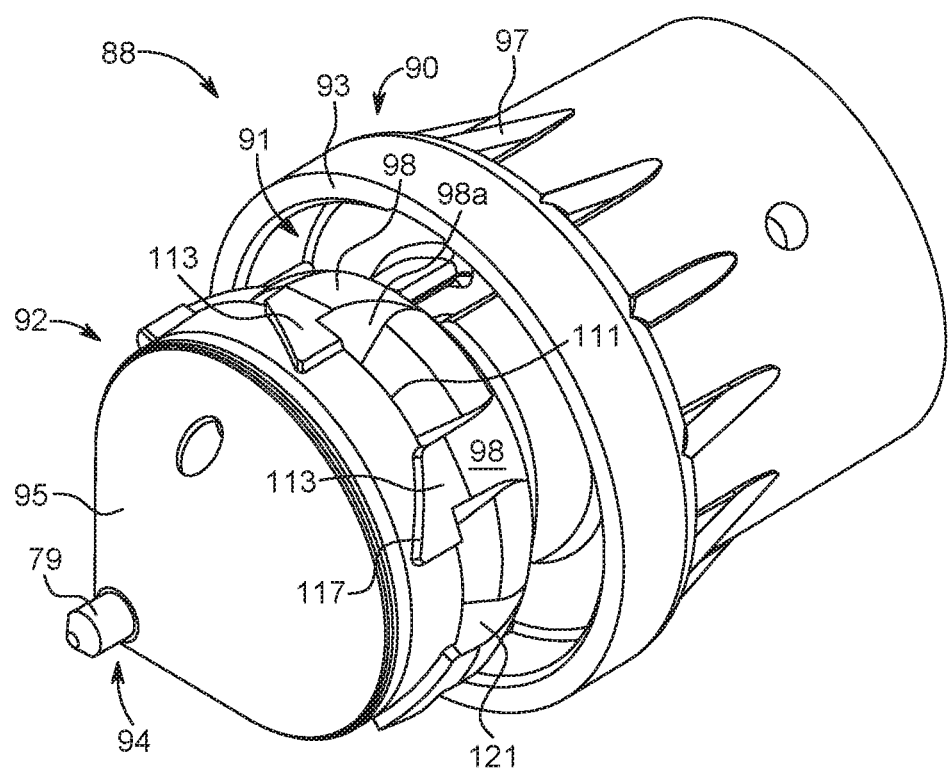
FIG. 15A is a front perspective view of a piston in accordance with another aspect.

With continued reference to FIG. 15A, the piston 88 includes a stem 90 and a piston head 92 formed on a distal end of the stem 90. The piston head 92 is construed from a rigid material, such as metal or plastic that resists deformation. The stem 90 may have a cavity 91 for collecting any fluid that may drip from the syringe and an annular collar 93 that surrounds the cavity 91. One or more buttresses 97 connect the annular collar 93 to the stem 90. The piston head 92 has a substantially cylindrical structure with a pointed or conical distal end 94 with a cap 95 that is shaped to be received inside at least a portion of the interior cavity 40 (shown in FIG. 3A) of the plunger 26. In some aspects, a sensing member 79, such as a pin connected to a sensor, may be provided. The sensing member 79 may extend along a longitudinal axis of the piston 88 and may protrude through at least a portion of the piston head 92, such as through at least a portion of the cap 95. The sensing member 79 may be operative for sensing contact with a surface, such as a surface of the plunger 26 and/or the plunger cover 58 (shown in FIG. 3E), and control a movement of the piston 88 based on the sensed condition. For example, an initial contact between the sensing member 79 and the plunger 26 and/or the plunger cover 58 may cause the pin to be retracted in a proximal direction such that it makes contact with the sensor. The sensing member 79 may be biased in an extended position by a resilient element 81 (shown in FIG. 15E), such as a spring. The sensor may be connected to the control mechanism which controls the drive mechanism of the piston 88 such that, upon activation of the sensor by the pin, the controller controls the movement of the drive mechanism. For example, the drive mechanism may be stopped or slowed from a first rate to a second, slower rate.

Figure 15B:
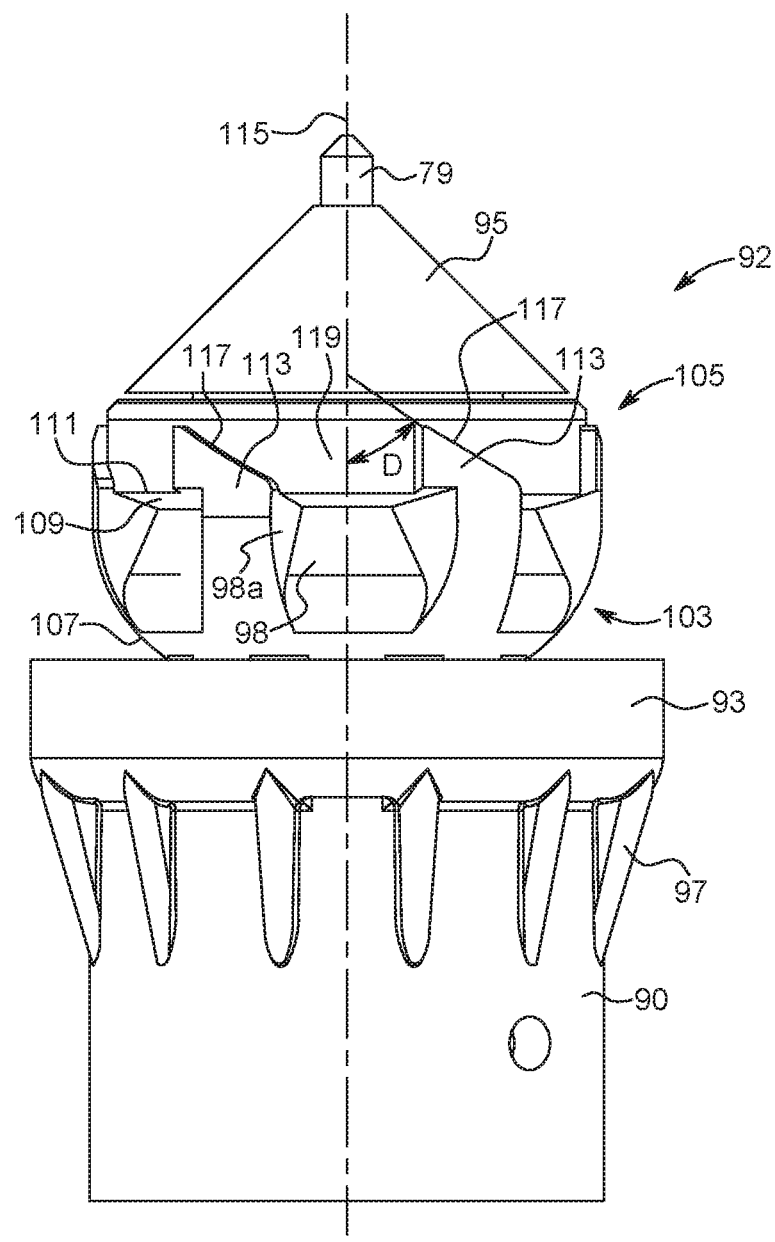
FIG. 15B is a side view of the piston head shown in FIG. 15A.

With reference to FIG. 15B, the piston head 92 has a proximal portion 103 connected to a distal portion 105. Terminal ends of the proximal and distal portions 103, 105 may have a radiused edge 107. At least a portion of the proximal portion 103 has a smaller outer diameter compared to an outer diameter of the distal portion 105 such that a radial lip 109 is formed at a transition between the proximal portion 103 and the distal portion 105. The radial lip 109 may be continuous or discontinuous around a circumference of the piston head 92. In some aspects, the radial lip 109 defines a locking ledge 111 for engaging the catch 74 of the at least one retaining member 68 when the plunger 26 is fully seated on the piston head 92.

With continued reference to FIG. 15B, the piston head 92 may have at least one second alignment member 113 protruding radially outward from an outer surface of the piston head 92. The at least second alignment member 113 is shaped and/or configured for interacting with the first alignment member 71 of the plunger 26 for facilitating alignment of the piston 88 with the plunger 26 in order to allow for a releasable locking connection of the plunger 26 with the piston 88. In some aspects, at least a portion of the at least second alignment member 113 may extend in a direction that is angled relative to the direction of a piston longitudinal axis 115. For example, at least second alignment member 113 may have a guiding surface 117 that is angled at an angle D relative to the piston longitudinal axis 115. The guiding surface 117 is desirably angled such that the piston head 92 may rotate around the piston stem 90, for example around an axis of the one-way rotation mechanism 99, when the proximal alignment surface 77a of the first alignment member 71 contacts the guiding surface 117 of the second alignment member 113.

In some aspects, a plurality of second alignment members 113 may be spaced apart radially relative to the piston longitudinal axis 115 along an outer circumference of the piston head 92. In some aspects, the number of second alignment members 113 may be equal to a total number of retaining members 68 and first alignment members 71 on the plunger 26. The second alignment members 113 are spaced apart circumferentially such that a retaining member 68 or a first alignment member 71 may be received between adjacent second alignment members 113. The second alignment members 113 may be separated from each other by portions of an outer surface of the proximal portion 103 and/or the distal portion 105 of the piston head 92.

Figure 15C:
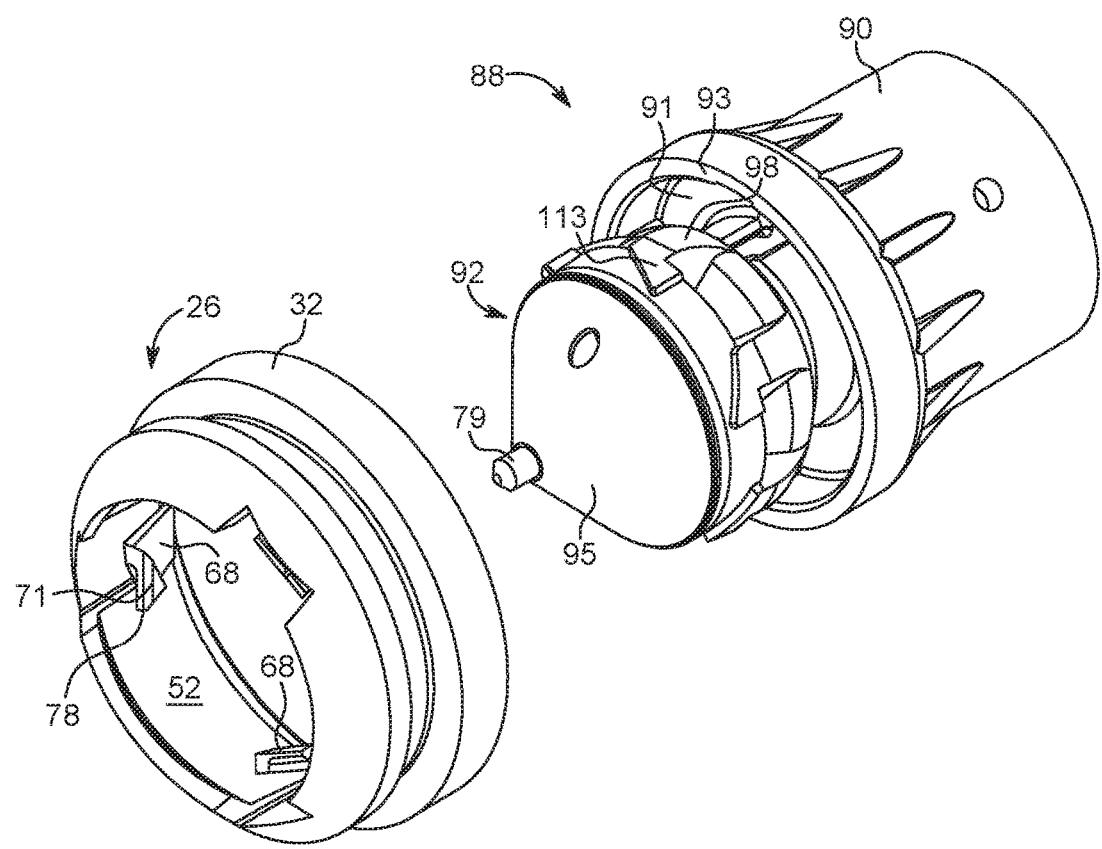
FIG. 15C is a front perspective view of the piston shown in FIG. 15A and a plunger removed from the piston.
Figure 15D:
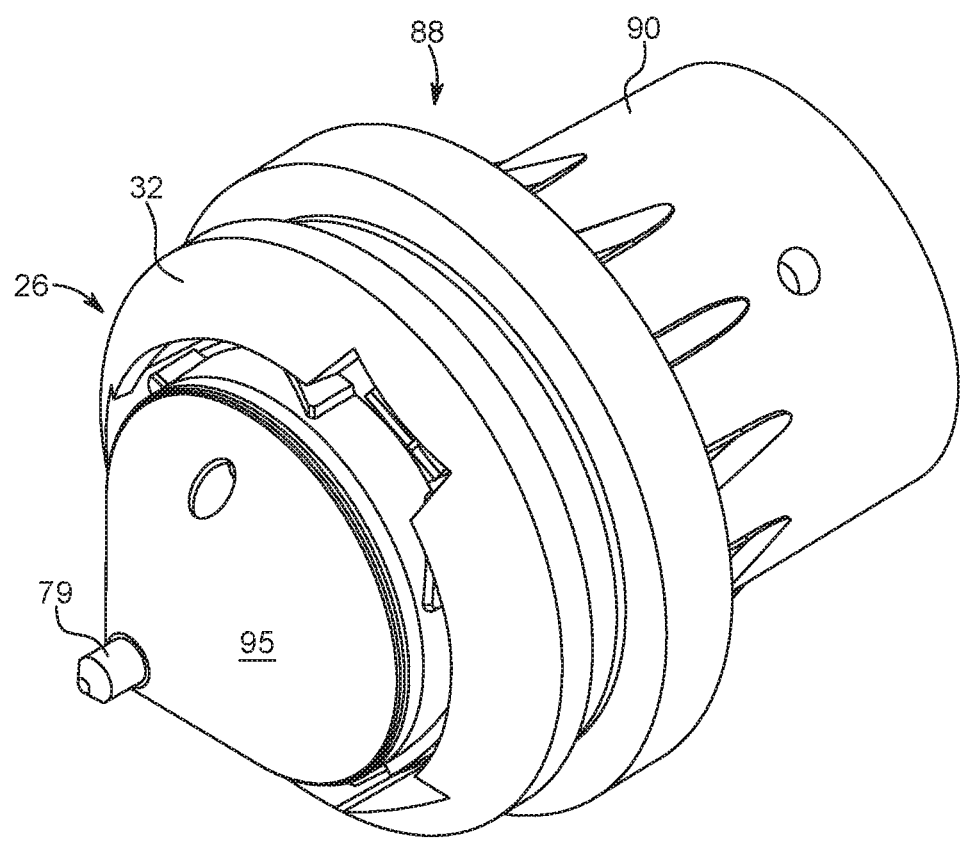
FIG. 15D is a front perspective of the piston and plunger shown in FIG. 15C with the plunger assembled on the piston.
Figure 15E:
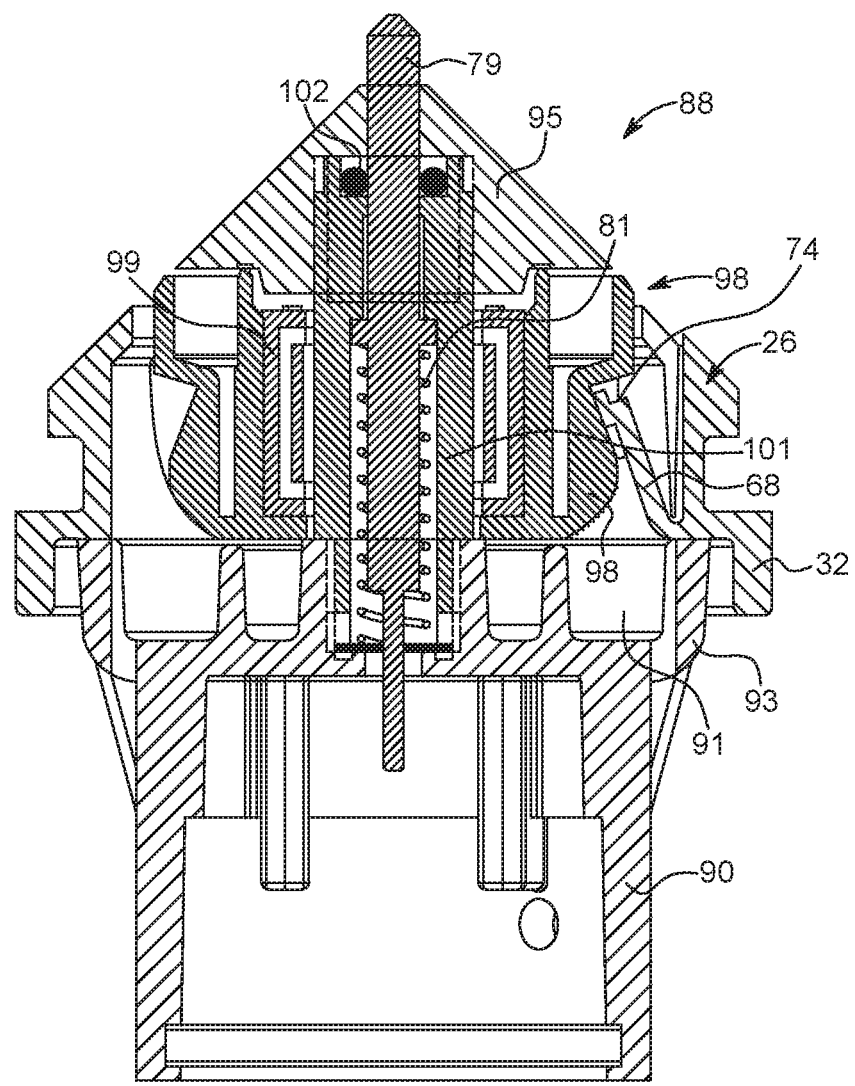
FIG. 15E is a side cross-sectional view of the plunger and the piston shown in FIG. 15D.
Figure 15F:
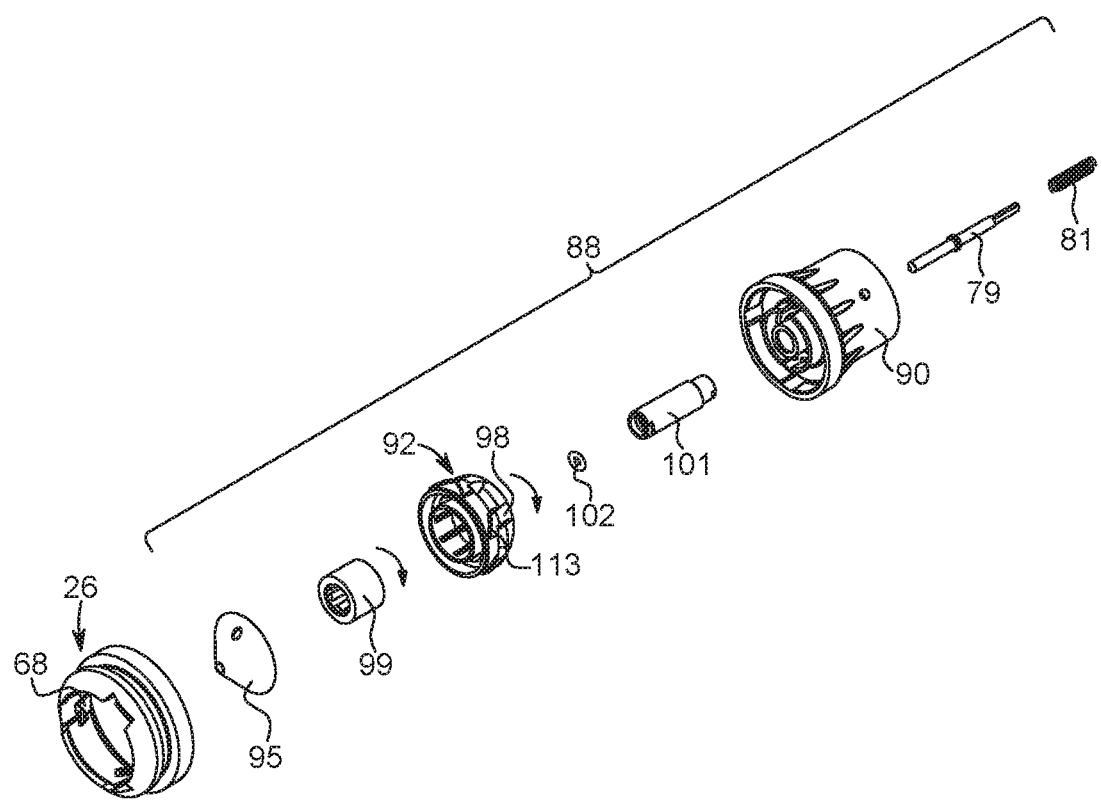
FIG. 15F is an exploded perspective view of the piston shown in FIG. 15A.
Figure 15G:
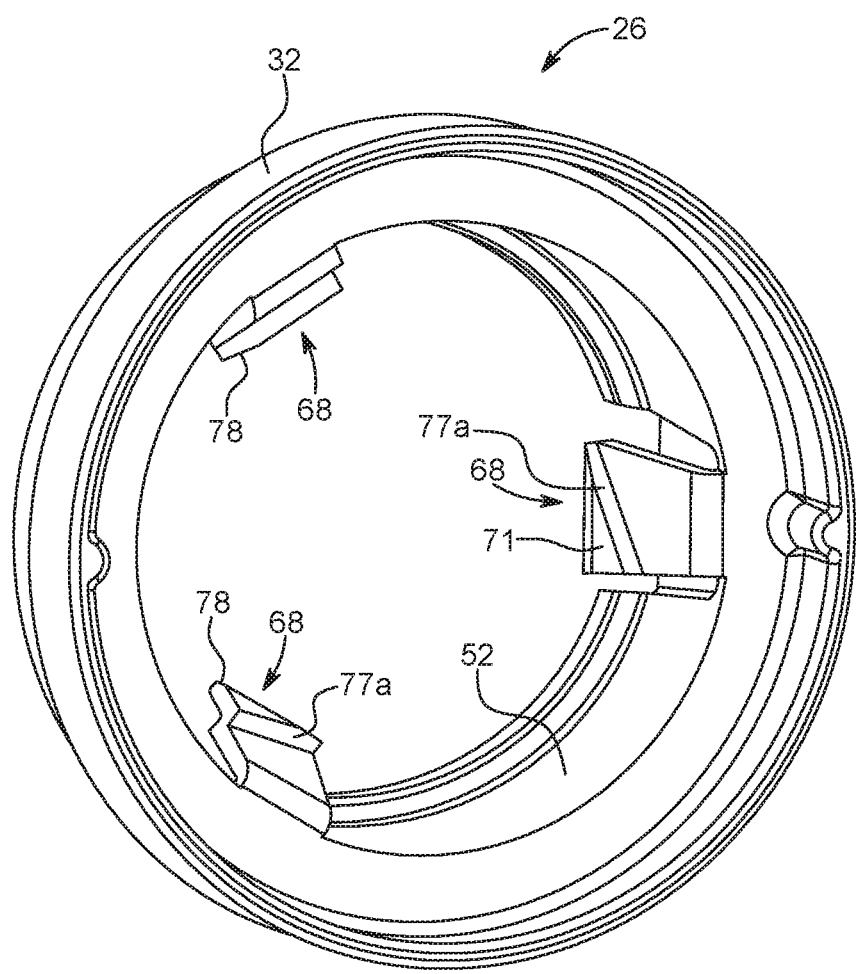
FIG. 15G is a bottom perspective view of a plunger in accordance with another aspect of the present disclosure.

With continued reference to FIG. 15B, each guiding surface 117 of the second alignment members 113 defines a travel path for guiding the movement of the proximal alignment surface 77a of the first alignment member 71 in and out of a recess 119 defined between adjacent second alignment members 113 (see FIG. 15G). The guiding surfaces 117 may be inclined or angled radially and axially relative to the piston longitudinal axis 115 to guide the movement of the proximal alignment surfaces 77a. The guiding surfaces 117 aid in self-orienting the piston head 92 as the plunger 26 (see FIG. 15G) is brought into contact with the piston 88 by guiding the one or more proximal alignment surfaces 77a on the plunger 26 into the corresponding recess 119 on the piston head 92. In this manner, a piston 88 whose piston longitudinal axis 115 is rotationally misaligned with the plunger longitudinal axis 34 and the one or more first alignment member 71 which are initially misaligned relative to the corresponding one or more second alignment members 113 in a rotational direction are brought in alignment axially and rotationally such that the one or more first alignment members 71 are received within the recess 119 between adjacent second alignment members 113. The one or more second alignment members 113 may have a bottom surface 121 that is angled relative to the direction of a piston longitudinal axis 115.

The piston head 92 further has an actuation surface that interacts with the actuation member on the plunger 26, such as the first cam member 78. In some aspects, the actuation surface on the piston head 92 may be a second cam member 98. In some aspects, the second cam member 98 cooperates with the first cam member 78 on the at least one retaining member 68 of the plunger 26, as described herein. The second cam member 98 desirably has a shape that, upon relative rotation between the piston 88 and the plunger 26, engages the first cam member 78 to cause the at least one retaining member 68 to be deflected from the piston head 92 such that the plunger 26 can be removed from the piston 88. In some aspects, the second cam member 98 may be formed on or intersect with the second alignment member 113 on the piston head 92. In certain aspects, the second cam member 98 may have a cam surface 98a extending radially outward and parallel to the longitudinal axis 115. The cam surface 98a may be aligned with a direction of the piston longitudinal axis 115. The second cam member 98 may have a chamfered portion, not shown, to facilitate passing of the first cam member 78 after the retaining member 68 is deflected sufficiently to allow the retaining member to be released.

With reference to FIG. 15C, the piston 88 is configured to interact with the plunger 26 to releasably lock with plunger 26, such as shown in FIG. 15D. By locking the piston 88 to the plunger 26, the plunger 26 can be driven reciprocally within the barrel of the syringe 12 (shown in FIG. 2). The second cam member 98 on the piston 88 cooperates with the first cam member 78 on the at least one retaining member 68 of the plunger 26, to releasably lock the plunger 26 to the piston 88.

With reference to FIG. 15F, the piston head 92 may be rotatable relative to the stem 90. In some aspects, the piston head 92 may be rotatable in one direction only, such as a clockwise or a counter-clockwise direction, relative to the stem 90. A one-way rotation mechanism 99, such as a one-way clutch mechanism shown in FIG. 15F, may be provided to allow the rotation of the piston head 92 in a first direction only, such as the clockwise or the counter-clockwise direction. The one-way rotation mechanism 99 may be rotatable around a central shaft 101 having a seal 102, such as an O-ring seal. In some aspects, the one-way rotation mechanism 99 may have a stop that prevents rotation of the piston head 92 in a second direction opposite the first direction, such as the counter-clockwise or the clockwise direction, respectively. In other aspects, the one-way rotation mechanism 99 may be provided on at least a portion of the plunger 26.

With reference to FIG. 15G, the at least one first alignment member 71 may be provided directly on one or more of the retaining members 68. In such aspects, at least one retaining member 68 may have a proximal alignment surface 77a provided directly on the body of the at least one retaining member 68. The first cam member 78 may be also provided directly on the retaining member 68 such that engagement of the cam member 78 causes a corresponding movement of the retaining member 68, as described herein. Cam member 78 may be provided on a side surface of retaining member 68 or may be provided on an edge of the at least one first alignment member 71 may be provided directly on one or more of the retaining members 68.

Figure 16:
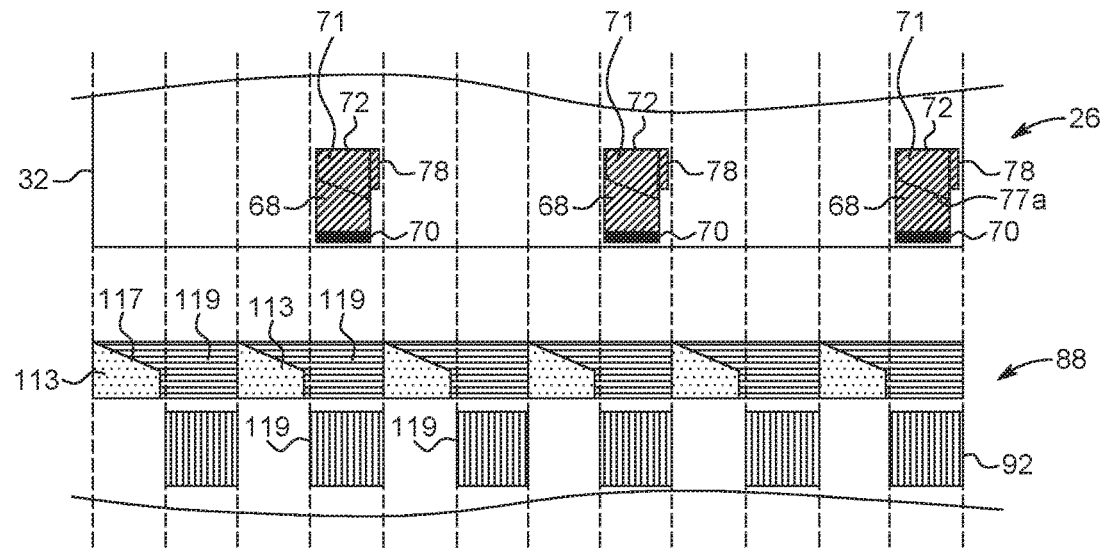
FIG. 16 is a cylindrical plan projection view of the piston and the plunger shown in FIG. 15C.

With reference to FIG. 16, a cylindrical plan projection view of one aspect of the piston 88 and the plunger 26 is shown. If the piston 88 is rotationally misaligned relative to the plunger 26 such that the first alignment members 71 directly on the retaining members 68 on the plunger 26 are not in rotational alignment to be received within the recesses 119 on the plunger head 92, the proximal alignment surface 77a (shown as a dotted line) of the first alignment member 71 on the plunger 26 contacts the guiding surface 117 of the second alignment member 113 on the piston head 92. Engagement of the proximal alignment surface 77a with the guiding surface 117 causes the piston head 92 to automatically rotate in a free rotation direction of the one-way rotation mechanism 99. Such rotation of the piston head 92 aligns the first alignment members 71 and the retaining members 68 to be received within the recesses 119 between adjacent second alignment members 113. In this manner, the piston 88 self-orients itself relative to the plunger 26 such that the plunger 26 may be releasably locked with the piston 88. If the piston 88 is rotationally aligned relative to the plunger 26, such as shown in FIG. 16, the first alignment members 71 and the retaining members 68 on the plunger 26 can be received within the recesses 119 between adjacent second alignment members 113 without rotation of the piston head 92.

Figure 17:
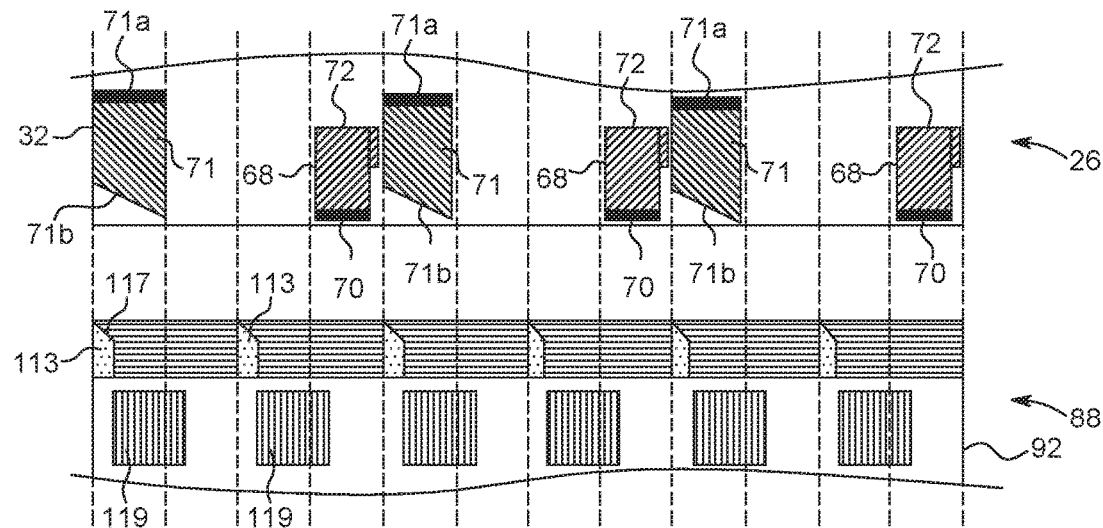
FIG. 17 is a cylindrical plan projection view of a piston and a plunger in accordance with another aspect of the present disclosure.

In some aspects, such as shown in FIG. 17, the plunger 26 may have one or more first alignment members 71 positioned adjacent to the one or more retaining members 68. In some aspects, the width of the second alignment member 113 on the piston head 92 in a circumferential direction may be reduced such that the first alignment member 71 and the retaining member 68 may be received in a same space defined between adjacent second alignment members 113 on the piston head 92. The one or more first alignment members 71 may have a first end 71a connected to the body 32 of the plunger and a second end 71b that protrudes in a proximal direction which is opposite to the protrusion direction of the second end 72 of the one or more retaining members 68. The second end 71b of the first alignment member 71 may be deflectable in a radial direction relative to the first end 71a. The first alignment members 71 may further have an angled guide surface, for example defined by an outer surface of the second end 71b, that cooperates with the second alignment members 113 of the piston head 92 to align the plunger 26 relative to the piston 88. During the engagement/disengagement process, the second end 71b of the first alignment members 71 may be deflected radially outward as it passes over the region defined by the recesses 119 and the second alignment members 113, and is deflected back in a radially inward direction once the second end 71b clears the recesses 119. The one or more first alignment members 71 may have a latching member (not shown) to lock with at least a portion of the piston head 92, such as the radial lip 109.

Figure 18:
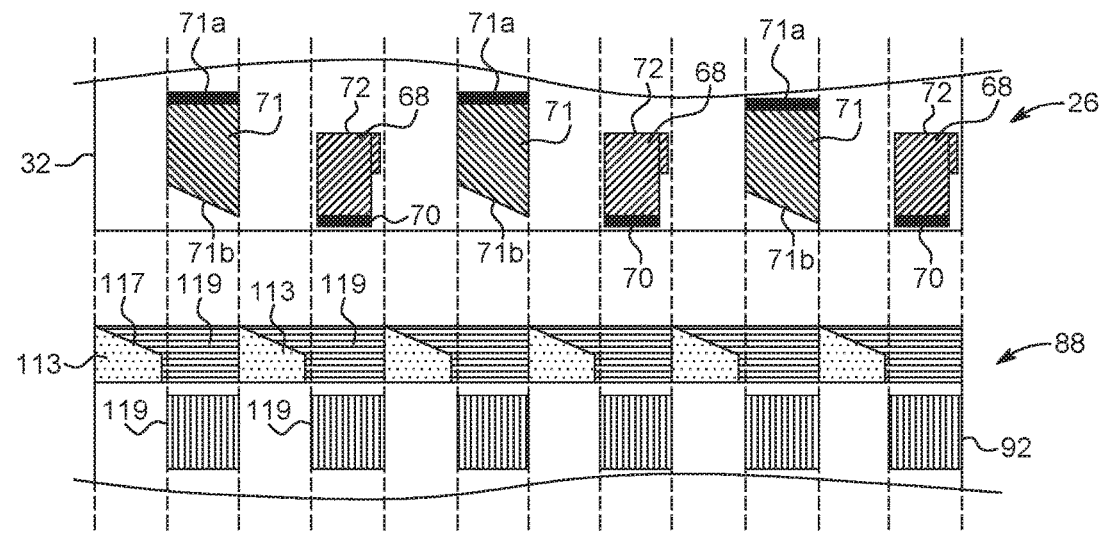
FIG. 18 is a cylindrical plan projection view of a piston and a plunger in accordance with another aspect of the present disclosure.
Figure 19:
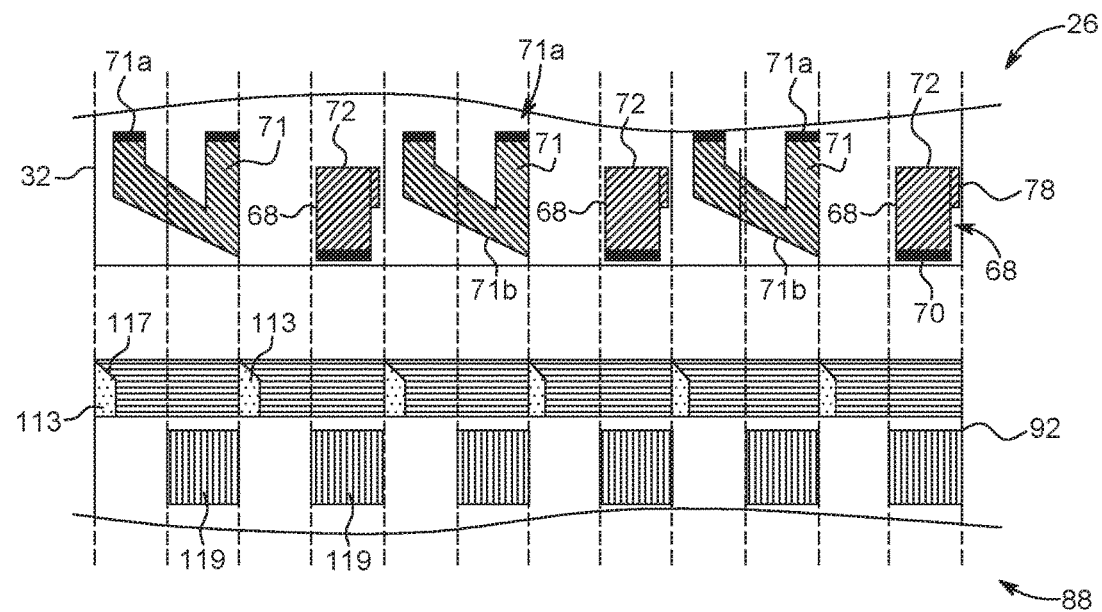
FIG. 19 is a cylindrical plan projection view of a piston and a plunger in accordance with another aspect of the present disclosure.

In another aspect, such as shown in FIG. 18, the one or more first alignment members 71 may be spaced apart from the one or more retaining members 68 such that each first alignment member 71 and the retaining member 68 is received in a separate space defined between adjacent second alignment members 113 on the piston head 92. With reference to FIG. 19, the at least one first alignment member 71 may be bifurcated and formed from two separate portions. Each portion may be separately attached to the plunger body 32. In some aspects, the two portions may be joined together at the second end 71b, such as shown in FIG. 19. In various aspects, interaction of the at least one first alignment member 71 on the plunger 26 with the one or more second alignment members 113 on the piston 88 causes self-orientation of the piston 88 such that at least one retaining member 68 is received in the recess 119 on the piston head 92.

Figure 20A:
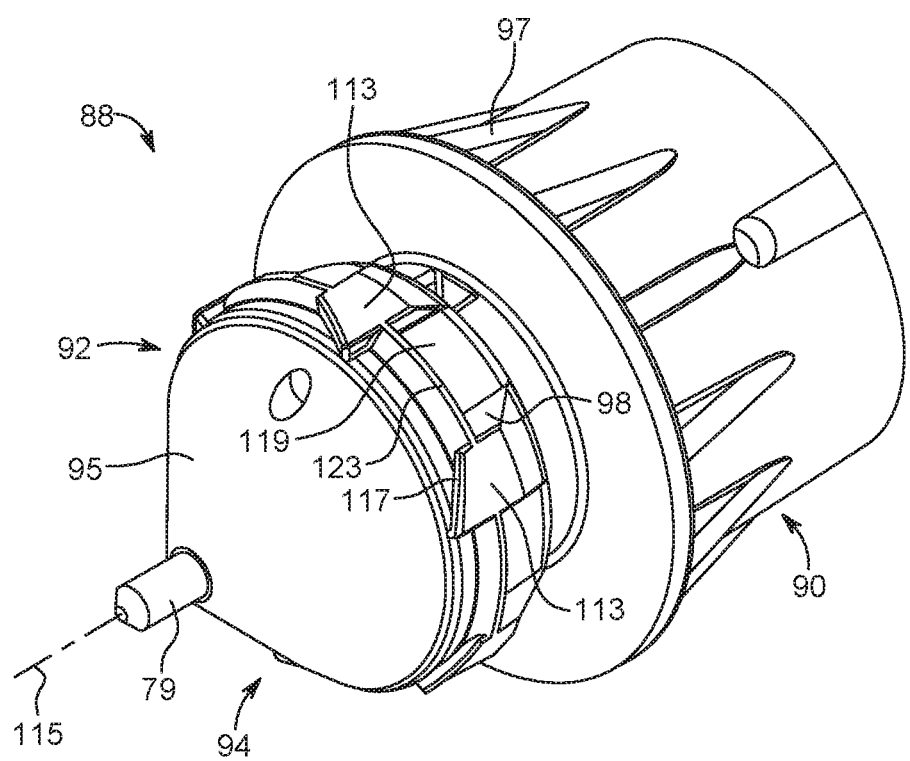
FIG. 20A is a top perspective view of a piston in accordance with another aspect.

With reference to FIG. 20A, according to certain aspects, at least a portion of the second alignment members 113, such as a lower or proximal end of the second alignment members 113 may be connected by a continuous lip 123 that extends continuously around an outer circumference of the piston head 92 at a radial position that may be flush with, radially recessed, or radially protruding relative to an outer surface of the second alignment members 113. In aspects where two or more second alignment members 113 are provided, the second alignment members 113 may be evenly spaced apart from each other. In one exemplary and non-limiting aspect with six second alignment members 113 having equal angular separation therebetween, each second alignment member 113 is separated by 60 degrees from the second alignment members 113 adjacent on either side. In some aspects, the second alignment members 113 may have unequal angular extension and/or unequal angular spacing between the second alignment members 113 about the outer surface of the proximal portion 103 and/or the distal portion 105 of the piston head 92. The radial spacing of the at least one second alignment members 113 relative to the piston longitudinal axis 115 is selected to correspond to an inner shape of the plunger 26 (shown in FIGS. 20B-20D) to allow the retaining members 68 and the first alignment members 71 to be received between adjacent second alignment members 113.

Figure 20B:
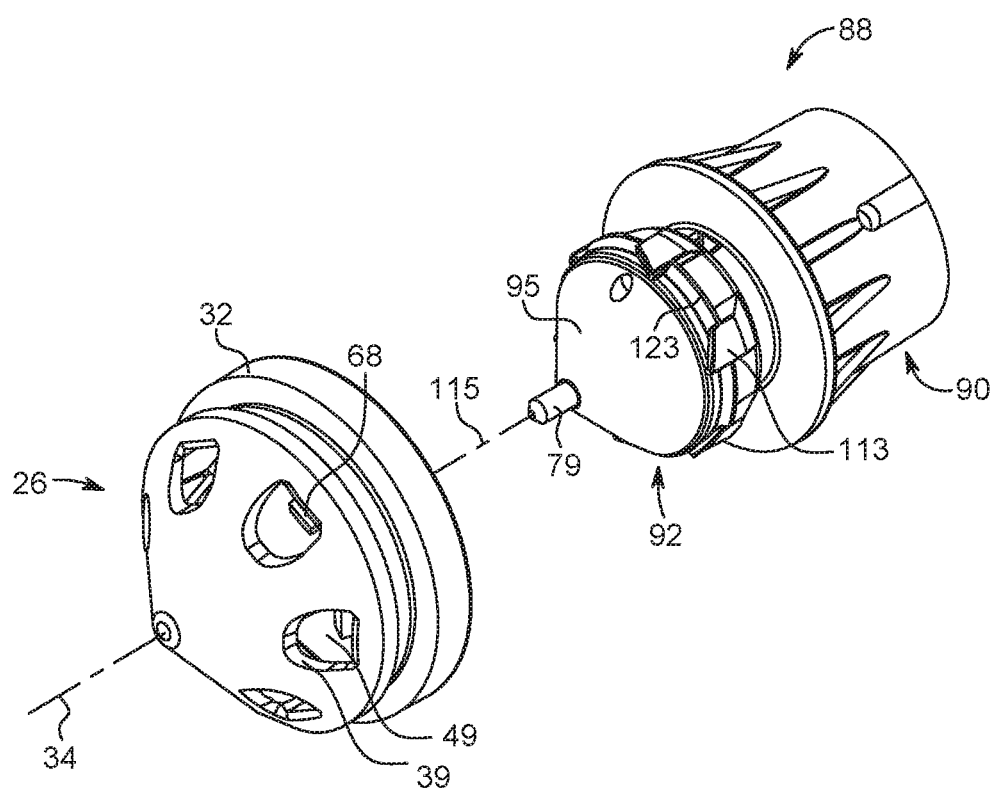
FIG. 20B is a top perspective view of the piston shown in FIG. 20A and a plunger in accordance with one aspect of the present disclosure.
Figure 20C:
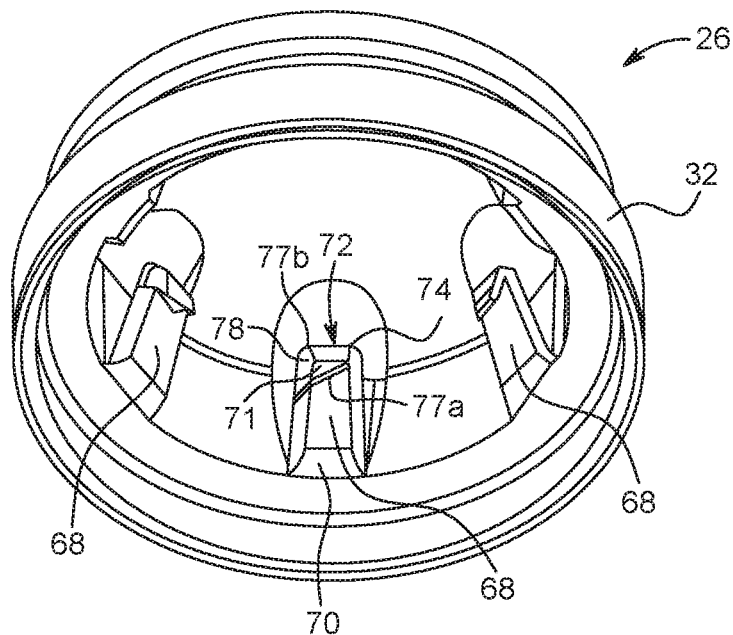
FIG. 20C is a bottom perspective view of the plunger shown in FIG. 20B.
Figure 20D:
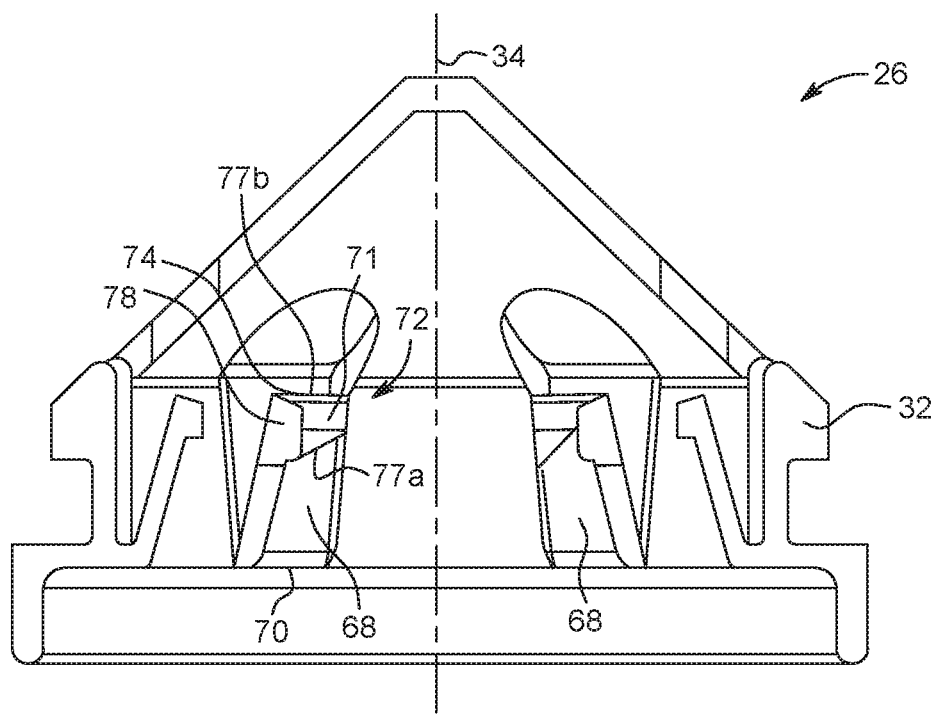
FIG. 20D is a side cross-sectional view of the plunger shown in FIG. 20C.

With reference to FIGS. 20C-20D, the at least one first alignment member 71 may be provided directly on one or more of the retaining members 68. In such aspects, at least one retaining member 68 may have a proximal alignment surface 77a and a distal alignment surface 77b provided directly on the body of the at least one retaining member 68. The proximal alignment surface 77a may be angled relative to the plunger longitudinal axis 34. In some aspects, the proximal alignment surface 77a may be aligned with the guiding surface 117 on the piston 88 (shown in FIG. 20A) such that the proximal alignment surface 77a is guided into the recess 119 on the piston head 92 (shown in FIG. 20A). The first cam member 78 may be also provided directly on the retaining member 68 such that engagement of the cam member 78 causes a corresponding movement of the retaining member 68, for example during rotation of the plunger 26 relative to the piston head 92 as described herein. The retaining members 68 may have at least one catch 74 that it formed on the second end 72 of the retaining member 68. The at least one catch 74 may be shaped to be received within locking ledge 111 on the piston 88 (shown in FIG. 20A) to lock the plunger 26 axially relative to the piston 88.

In some aspects, the at least one catch 74 may be linear or curvilinear. In some aspects, the at least one catch 74 may be oriented in a direction substantially perpendicular to a direction of the plunger longitudinal axis 34. In other aspects, the at least one catch 74 may be angled relative to a direction of the plunger longitudinal axis 34. The at least one catch 74 may be continuous or discontinuous. In some aspects, the at least one catch 74 may protrude radially inward toward the plunger longitudinal axis 34. With reference to FIG. 20B, the distal end 38 of the plunger body 32 may have one or more openings 49 extending through the plunger body 32. The one or more openings 49 may be spaced apart radially relative to the plunger longitudinal axis 34. The openings 49 may have equal or unequal angular extension and/or equal or unequal angular spacing between each other. In some aspects, the one or more openings 49 may be formed to facilitate molding of the plunger body 32. For example, the one or more openings 49 define a path for a molding tool to follow during the molding process of the plunger 26.

Figure 21A:
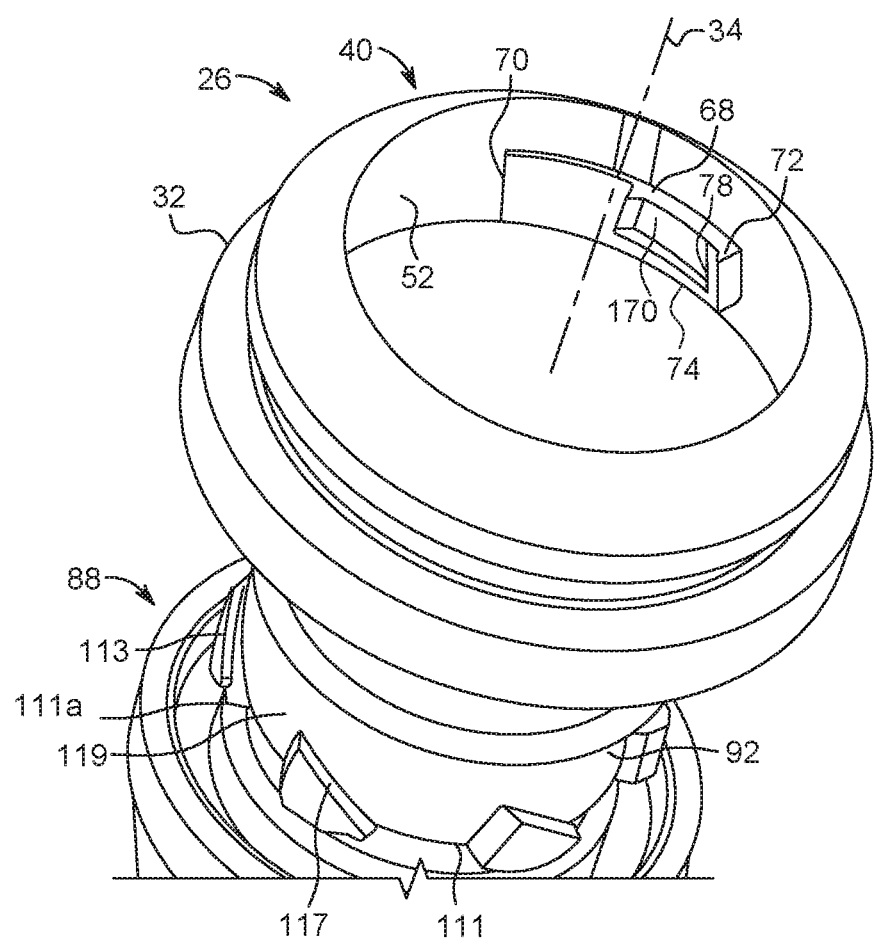
FIG. 21A is a front perspective view of a piston and a plunger in accordance with another aspect of the present disclosure.
Figure 21B:
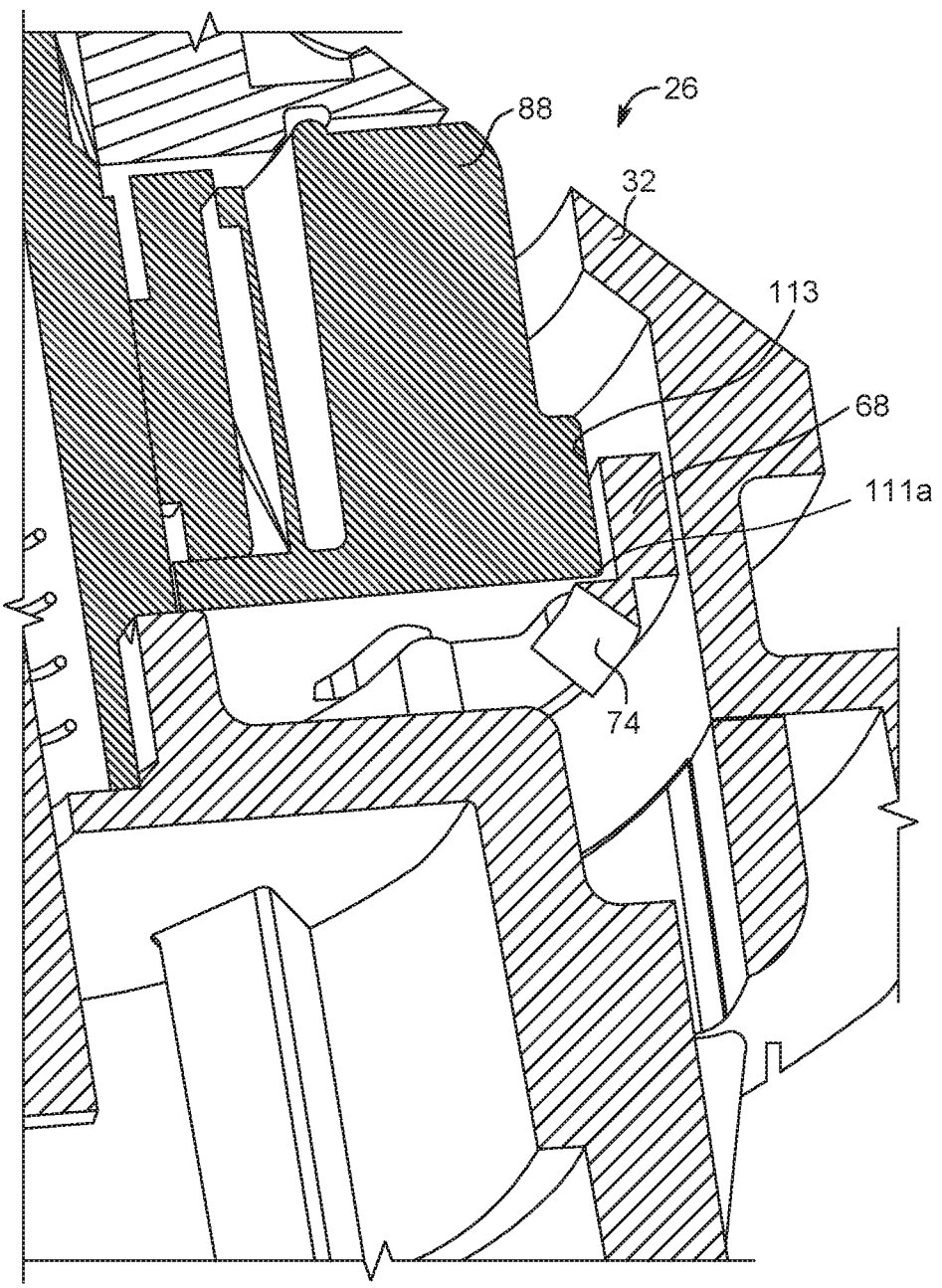
FIG. 21B is a detailed cross-sectional side view of FIG. 21A showing the engagement between the piston and the plunger.
Figure 21C:
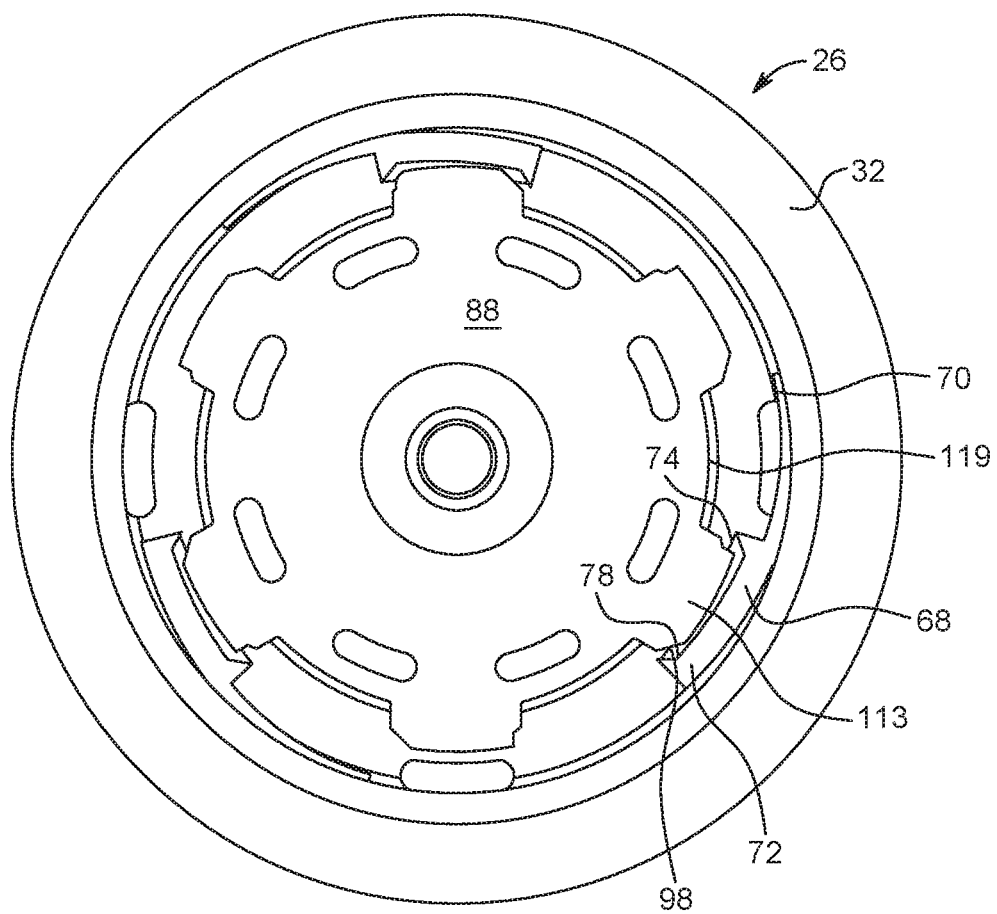
FIG. 21C is a cross-sectional top view of FIG. 21A showing the engagement between the piston and the plunger.

With reference to FIGS. 21A-21C, a plunger 26 and a piston 88 are shown in accordance with another aspect of the present disclosure. The components of the plunger 26 shown in FIGS. 21A-21C are substantially similar to the components of the plunger 26 described herein with reference to FIGS. 3A-3C. Similarly, the components of the piston 88 shown in FIGS. 21A-21C are substantially similar to the components of the piston 88 described herein with reference to FIGS. 4A-4C. Reference numerals in FIGS. 21A-21C are used to illustrate identical components of the corresponding reference numerals in FIGS. 3A-4C. As the previous discussion regarding the plunger 26 and piston 88 generally shown in FIGS. 3A-4C is applicable to the aspect of the present disclosure shown in FIGS. 21A-21C, only the relative differences between the plunger 26 and piston 88 generally shown in FIGS. 3A-4C and the plunger 26 and piston 88 generally shown in FIGS. 21A-21C are discussed hereinafter.

With reference to FIG. 21A, the plunger 26 may have at least one resiliently deflectable retaining member 68 (hereinafter "retaining member 68") protruding from the plunger body 32. In some aspects, the at least one retaining member 68 may protrude in a circumferential direction extending around an inner circumference of the inner surface 52 of the interior cavity 40. In some aspects, the at least one retaining member 68 may extend substantially perpendicularly to a longitudinal axis 34 of the plunger body 32. In other aspects, the at least one retaining member 68 may be angled in a distal or proximal direction relative a plane extending perpendicularly to the longitudinal axis 34 of the plunger body 32. Features such as the at least one alignment members 71 are omitted for clarity.

With continued reference to FIG. 21A, the at least one retaining member 68 has a first segment or a first end 70 connected to the plunger body 32 and a second segment or a second end 72 extending circumferentially around at least a portion an inner circumference of the plunger body 32 relative to the first end 70. The second end 72 may deflect and/or twist relative to the first end 70. As described herein, the second end 72 may be circumferentially and/or radially deflectable toward or away from the inner surface of the plunger body 32 relative to the first end 70. The first end 70 and the second end 72 may be spaced apart in a direction that extends substantially circumferentially around an inner surface of the plunger body 32. The at least one retaining member 68 may be linearly, stepwise, or curvilinearly contiguous between the first end 70 and the second end 72.

In some aspects, a plurality of retaining members 68 may be spaced apart radially relative to the plunger longitudinal axis 34 along a circumference of the inner surface 52 of the interior cavity 40. The retaining members 68 may be separated from each other, such as by even or uneven spacing, by portions of the inner surface 52 of the interior cavity 40. The radial spacing of the at least one retaining member 68 relative to the plunger longitudinal axis 34 is selected to correspond to or operably interact with an outer shape of the piston, as described herein.

With reference to FIG. 21B, the second end 72 of the retaining member 68 has at least one catch 74 that is shaped to engage at least a portion of a recess, lip, or ledge on the piston to lock the at least one retaining member 68, along with the plunger 26, relative to the piston. In some aspects, the at least one catch 74 may protrude radially inward or outward relative to a body of the retaining member 68. The at least one catch 74 may be formed integrally with the second end 72 of the at least one retaining member 68 or it may be affixed or otherwise secured to the second end 72 of the at least one retaining member 68 using, for example, a frictional fit and/or an adhesive, welding, or by molding.

With reference to FIG. 21C, the plunger 26 may have at least one actuation member, such as a first cam member 78 that interacts with a piston of the fluid injector 10 (shown in FIG. 1) to radially deflect the at least one retaining member 68 upon rotation of the plunger 26 relative to the piston, as described herein. The at least one first cam member 78 may be provided at the second end 72 of the retaining member 68. The at least one first cam member 78 may be angled relative to the body of the retaining member 68. In some aspects, the at least one cam member 78 may be on at least one surface of a pocket 170 formed on the second end 72 of the at least one retaining member 68.

The plunger 26 may have at least one alignment member, such as the first alignment member 71 shown in FIG. 3A protruding from the plunger body 32. As described herein, the at least one first alignment member 71 is shaped and/or configured for facilitating self-orienting alignment of the plunger 26 with the piston 88.

To engage the plunger 26 with the piston 88, the syringe 12 is first inserted into the syringe port 16 of the fluid injector 10 (shown in FIG. 1), as described herein. If the piston 88 is rotationally misaligned relative to the plunger 26 such that the one or more alignment members on the plunger 26 are not in rotational alignment to be received within the recesses 119 on the plunger head 92, the one or more alignment members on the plunger 26 contact the guiding surface 117 of the second alignment member 113 on the piston head 92 to rotate the piston head 92 into alignment for connecting to the plunger 26. In this manner, the piston 88 self-orients itself relative to the plunger 26 such that the plunger 26 may be releasably locked with the piston 88. Distal movement of the piston 88 causes the retaining members 68 to circumferentially deflect outward relative to the plunger longitudinal axis 34 from a first, undeflected position, to a second deflected position. The piston 88 is advanced distally until the terminal portion of the second end 72 clears the retaining members 68, thereby allowing them to deflect circumferentially inward toward or to their initial undeflected position. The catch 74 of at least one retaining member 68 is retained within the locking ledge 111 of the recess 119 or under a locking ledge 111*a* formed on a proximal end of the at least one second alignment member 113 on the piston head 92 to prevent disengagement of the plunger 26 from the piston head 92, for example by a frictional fit against a second portion of the inner wall of the plunger 26. In some aspects, such as shown in FIG. 21B, at least a portion of the piston 88, such as the at least one second alignment member 113, may have a locking ledge 111a that engages the catch 74 when the plunger 26 is connected to the piston 88 to prevent the plunger 26 from disconnecting from the piston 88 when the plunger 26 is moved in a proximal direction within the syringe barrel 18 (shown in FIG. 2).

To unlock the syringe 12 from the syringe port 16 (shown in FIG. 1) and disengage the plunger 26 from the piston 88, the syringe 12 is rotated clockwise or counter-clockwise about the syringe longitudinal axis, in a clockwise or counter-clockwise direction, relative to the syringe port 16. Rotation of the syringe 12, and thereby the plunger 26, about the plunger longitudinal axis 34 engages the first cam member 78 on the plunger 26 with the second cam member 98 on the piston head 92. Such movement causes a circumferential deflection of the at least one retaining member 68 away from the piston head 92 to unlock the plunger 26 from the piston head 92 and allow the removal of the syringe 12.

With reference to FIGS. 22A-22D, a plunger 26 and a piston 88 are shown in accordance with another aspect of the present disclosure. The components of the plunger 26 shown in FIGS. 22A-22D are substantially similar to the components of the plunger 26 described herein with reference to FIGS. 3A-3C. Similarly, the components of the piston 88 shown in FIGS. 22A-22D are substantially similar to the components of the piston 88 described herein with reference to FIGS. 4A-4C. Reference numerals in FIGS. 22A-22D are used to illustrate identical components of the corresponding reference numerals in FIGS. 3A-4C. As the previous discussion regarding the plunger 26 and piston 88 generally shown in FIGS. 3A-4C is applicable to the aspect of the present disclosure shown in FIGS. 22A-22D, only the relative differences between the plunger 26 and piston 88 generally shown in FIGS. 3A-4C and the plunger 26 and piston 88 generally shown in FIGS. 22A-22D are discussed hereinafter.

Figure 22A:
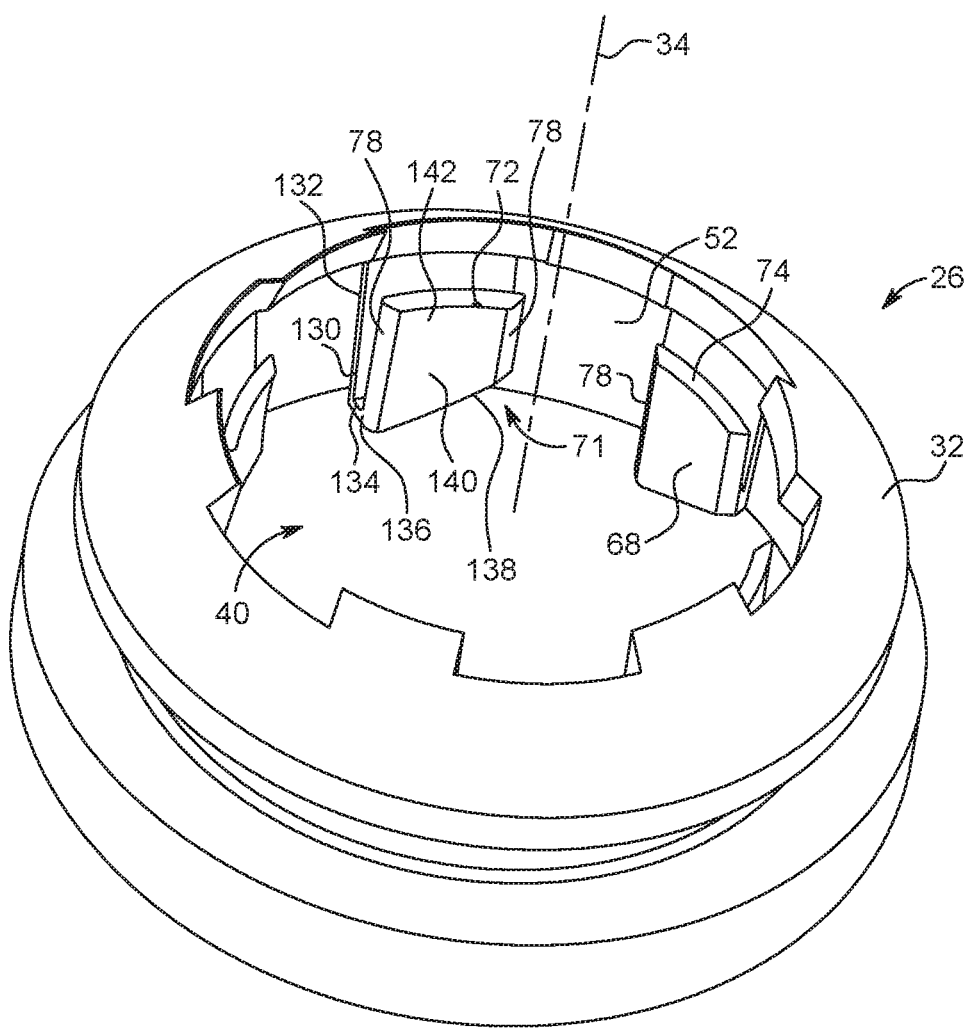
FIG. 22A is a top perspective view of a plunger in accordance with another aspect of the present disclosure.
Figure 22B:
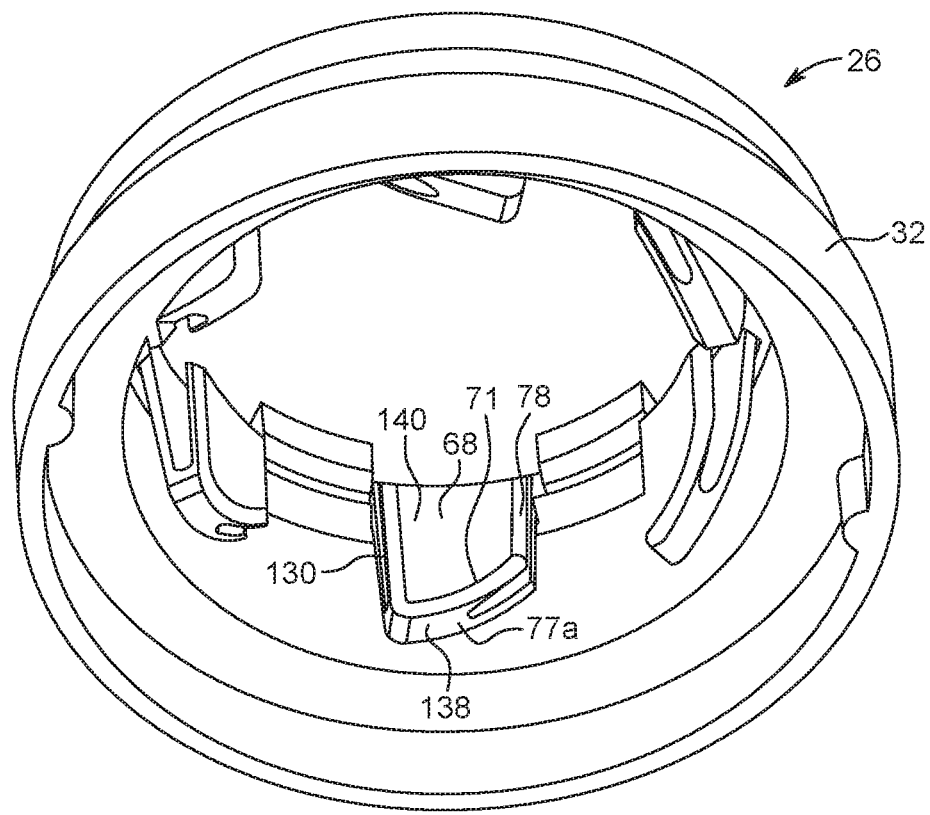
FIG. 22B is a bottom perspective view of the plunger shown in FIG. 22A.

With reference to FIG. 22A, the plunger 26 may have at least one resiliently deflectable retaining member 68 (hereinafter "retaining member 68") protruding from the plunger body 32. In some aspects, the at least one retaining member 68 may be U-shaped, with a first portion 130 having a first end 132 connected to the plunger body 32 and a second end 134 extending in a direction toward the proximal end of the plunger body 32. The at least one retaining member 68 may further have a transition portion 136 connected to the second end 134 of the first portion 130. A first end 138 of a second portion 140 may be connected to the transition portion 136 at an end opposite to the connection of the second end 134 of the first portion 130. The transition portion 136 extends in a radial direction relative to the longitudinal axis 34 of the plunger body 32 and connects the first portion 130 to the second portion 140. A second end 142 of the second portion 140 extends toward the distal end of the plunger body 32. The first portion 130, the second portion 140, or both may deflect or twist relative to the plunger body 32. For example, the second end 134 of the first portion 130 may be deflectable in a radial or circumferential direction relative to the first end 132 and the plunger body 32. Alternatively, or in addition, the second end 142 of the second portion 140 may be deflectable in a radial or circumferential direction relative to the first end 138, and therefore, relative to the first portion 130 and the plunger body 32. In some aspects, a plurality of retaining members 68 may be spaced apart radially relative to the plunger longitudinal axis 34 along a circumference of the inner surface 52 of the interior cavity 40. The retaining members 68 may be separated from each other, such as by even or uneven spacing, by portions of the inner surface 52 of the interior cavity 40. The radial spacing of the at least one retaining member 68 relative to the plunger longitudinal axis 34 is selected to correspond to or operably interact with an outer shape of the piston, as described herein.

With reference to FIG. 22A, the second end 142 of the second portion 140 of the retaining member 68 has at least one catch 74 that is shaped to engage at least a portion of a recess, lip, or ledge on the piston to lock the at least one retaining member 68, along with the plunger 26, relative to the piston. In some aspects, the at least one catch 74 may protrude radially inward or outward relative to a body of the retaining member 68. The at least one catch 74 may be formed integrally with the second end 142 of the second portion 140 of the at least one retaining member 68 or it may be affixed or otherwise secured to the second end 72 of the at least one retaining member 68 using, for example, a frictional fit and/or an adhesive, welding, or by molding.

Figure 22C:
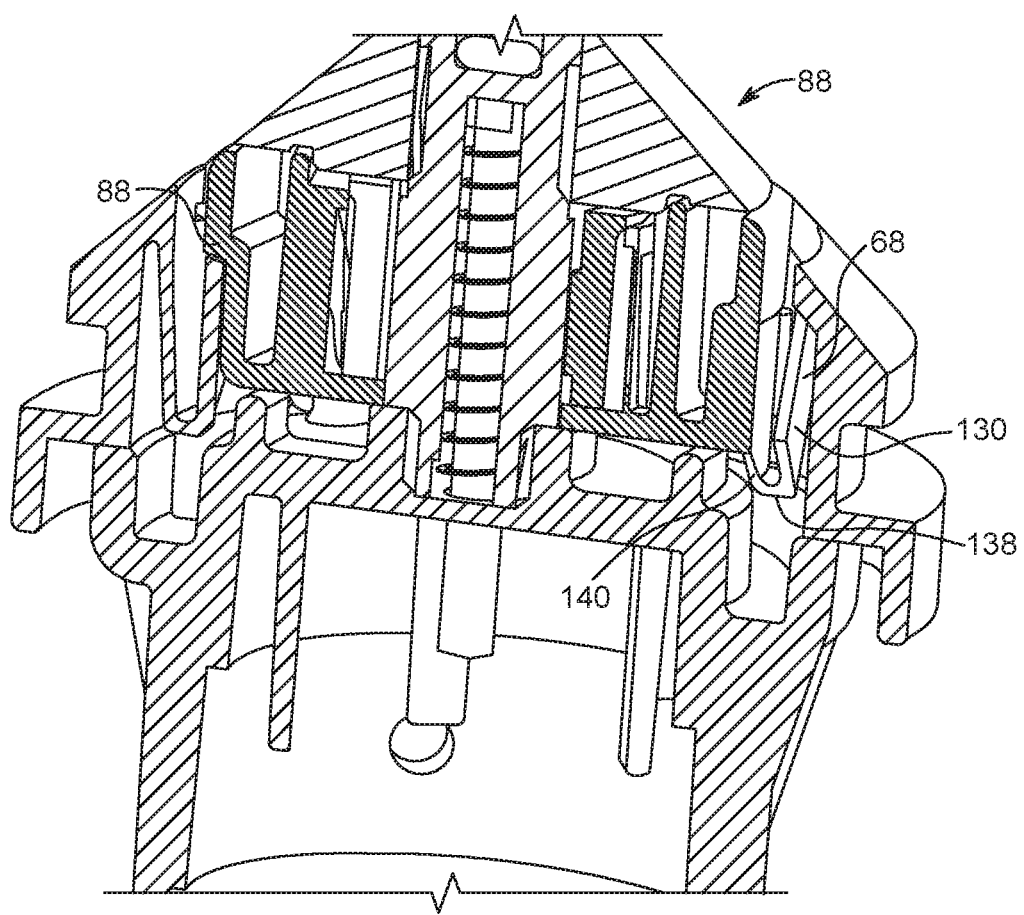
FIG. 22C is a cross-sectional side view of the plunger illustrated in FIG. 22A showing the engagement between a piston and the plunger.
Figure 22D:
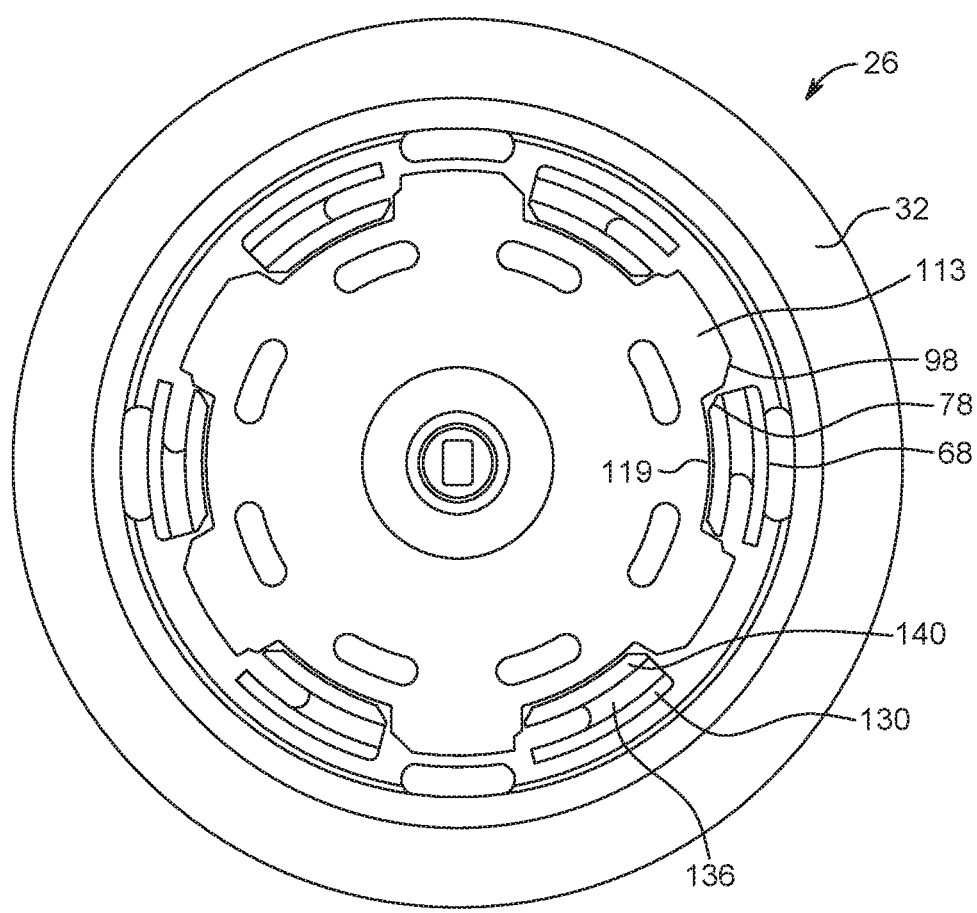
FIG. 22D is a cross-sectional top view of the plunger illustrated in FIG. 22A showing the engagement between a piston and the plunger.

With reference to FIG. 22C, the plunger 26 may have at least one first cam member 78 that interacts with a piston of the fluid injector 10 (shown in FIG. 1) to radially deflect the at least one retaining member 68 upon rotation of the plunger 26 relative to the piston, as described herein. The at least one first cam member 78 may be provided on the second portion 140 of the at least one retaining member 68. The at least one first cam member 78 may be angled at an angle B relative to the body of the retaining member 68.

With reference to FIG. 22A, the plunger 26 may have at least one first alignment member 71 defined on at least a portion of the at least one retaining member 68, such as the transition portion 136. The at least one first alignment member 71 is shaped and/or configured for facilitating self-orienting alignment of the plunger 26 with the piston 88. In some aspects, at least a portion of the at least one first alignment member 71 may extend in a direction that is angled relative to the direction of the plunger longitudinal axis 34. For example, at least one first alignment member 71 may have a proximal alignment surface 77a that is angled at an angle C relative to the longitudinal axis 34 to facilitate positioning of the retaining member 68 during connection of the plunger 26 to a piston. The proximal alignment surface 77a helps guide the plunger 26 into self-orienting alignment with the piston, as described herein.

To engage the plunger 26 with the piston 88, the syringe 12 is first inserted into the syringe port 16 of the fluid injector 10 (shown in FIG. 1), as described herein. If the piston 88 is rotationally misaligned relative to the plunger 26 such that the one or more alignment members on the plunger 26 are not in rotational alignment to be received within the recesses 119 on the plunger head 92, the one or more alignment members on the plunger 26 contact the guiding surface 117 of the second alignment member 113 on the piston head 92 to rotate the piston head 92 into alignment for connecting to the plunger 26. In this manner, the piston 88 self-orients itself relative to the plunger 26 such that the plunger 26 may be releasably locked with the piston 88. Distal movement of the piston 88 causes the retaining members 68 to deflect outward relative to the plunger longitudinal axis 34 from a first, undeflected position, to a second, radially deflected position. The piston 88 is advanced distally until the terminal portion of the second end 72 clears the retaining members 68, thereby allowing them to deflect radially inward toward or to their initial undeflected position. The catch 74 of at least one retaining member 68 is retained within the locking ledge 111 to prevent disengagement of the plunger 26 from the piston head 92.

To unlock the syringe 12 from the syringe port 16 (shown in FIG. 1) and disengage the plunger 26 from the piston 88, the syringe 12 is rotated clockwise or counter-clockwise about the syringe longitudinal axis, in a clockwise or counter-clockwise direction, relative to the syringe port 16. Rotation of the syringe 12, and thereby the plunger 26, about the plunger longitudinal axis 34 engages the first cam member 78 on the plunger 26 with the second cam member 98 on the piston head 92. Such movement causes a deflection of the at least one retaining member 68 away from the piston head 92 to unlock the plunger 26 from the piston head 92 and allow the removal of the syringe 12.

With reference to FIGS. 23A-23D, a plunger 26 and a piston 88 are shown in accordance with another aspect of the present disclosure. The components of the plunger 26 shown in FIGS. 23A-23D are substantially similar to the components of the plunger 26 described herein with reference to FIGS. 3A-3C and other aspects described herein. Similarly, some of the components of the piston 88 shown in FIGS. 23A-23D are substantially similar to some of the components of the piston 88 described herein with reference to FIGS. 4A-4C. Reference numerals in FIGS. 23A-23D are used to illustrate identical components of the corresponding reference numerals in FIGS. 3A-4C. As the previous discussion regarding the plunger 26 and piston 88 generally shown in FIGS. 3A-4C is applicable to the aspect of the present disclosure shown in FIGS. 23A-23D, only the relative differences between the plunger 26 and piston 88 generally shown in FIGS. 3A-4C and the plunger 26 and piston 88 generally shown in FIGS. 23A-23D are discussed hereinafter.

Figure 23A:
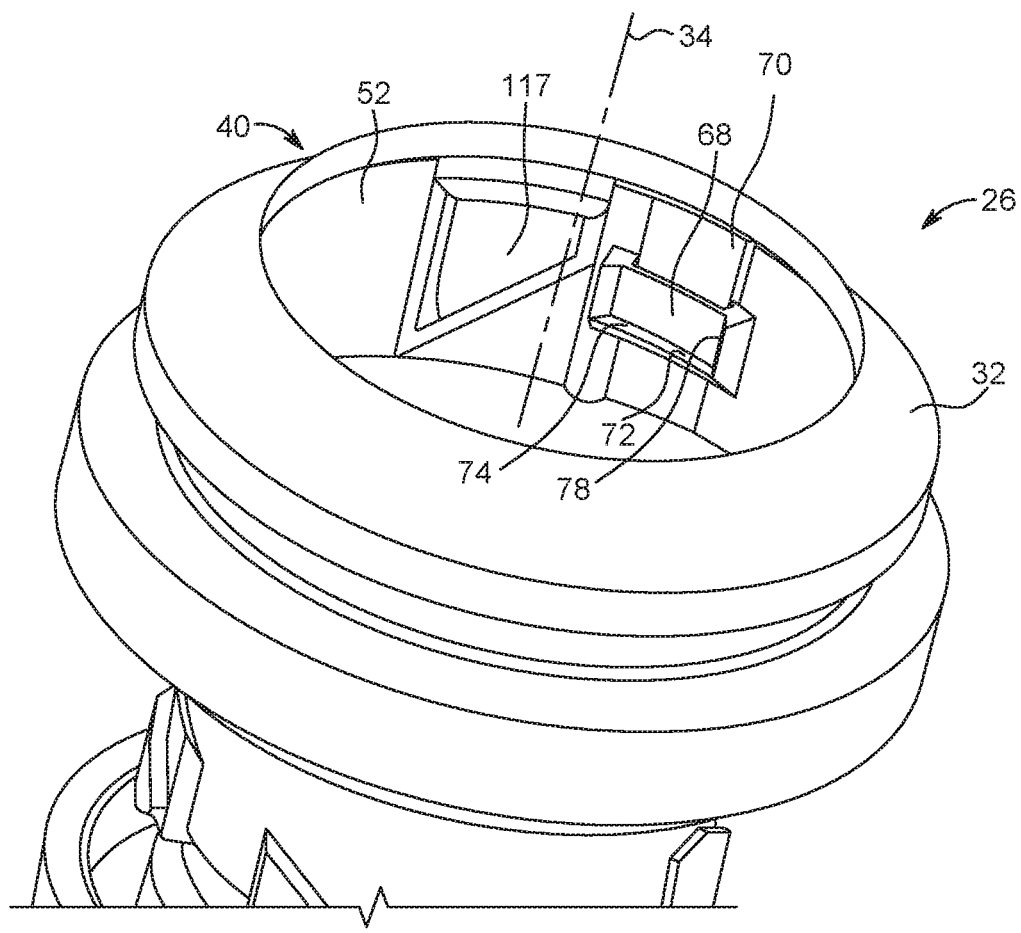
FIG. 23A is a top perspective view of a plunger in accordance with another aspect of the present disclosure.

With reference to FIG. 23A, the plunger 26 may have at least one resiliently deflectable retaining member 68 (hereinafter "retaining member 68") protruding from the plunger body 32. In some aspects, the at least one retaining member 68 may protrude in a proximal direction toward the proximal end of the plunger body 32. In some aspects, the at least one retaining member 68 may extend substantially parallel to a longitudinal axis 34 of the plunger body 32. In other aspects, the at least one retaining member 68 may be angled relative to the longitudinal axis 34 of the plunger body 32.

With continued reference to FIG. 23A, the at least one retaining member 68 has a first segment or a first end 70 connected to the plunger body 32 and a second segment or a second end 72 extending in a proximal direction relative to the first end 70. The second end 72 may deflect or twist relative to the first end 70. As described herein, the second end 72 may be radially deflectable toward or away from the inner surface of the plunger body 32 relative to the first end 70. The at least one retaining member 68 may be linearly, stepwise, or curvilinearly contiguous between the first end 70 and the second end 72. In some aspects, a plurality of retaining members 68 may be spaced apart radially relative to the plunger longitudinal axis 34 along a circumference of the inner surface 52 of the interior cavity 40. The retaining members 68 may be separated from each other, such as by even or uneven spacing, by portions of the inner surface 52 of the interior cavity 40. The radial spacing of the at least one retaining member 68 relative to the plunger longitudinal axis 34 is selected to correspond to or operably interact with an outer shape of the piston, as described herein.

Figure 23B:
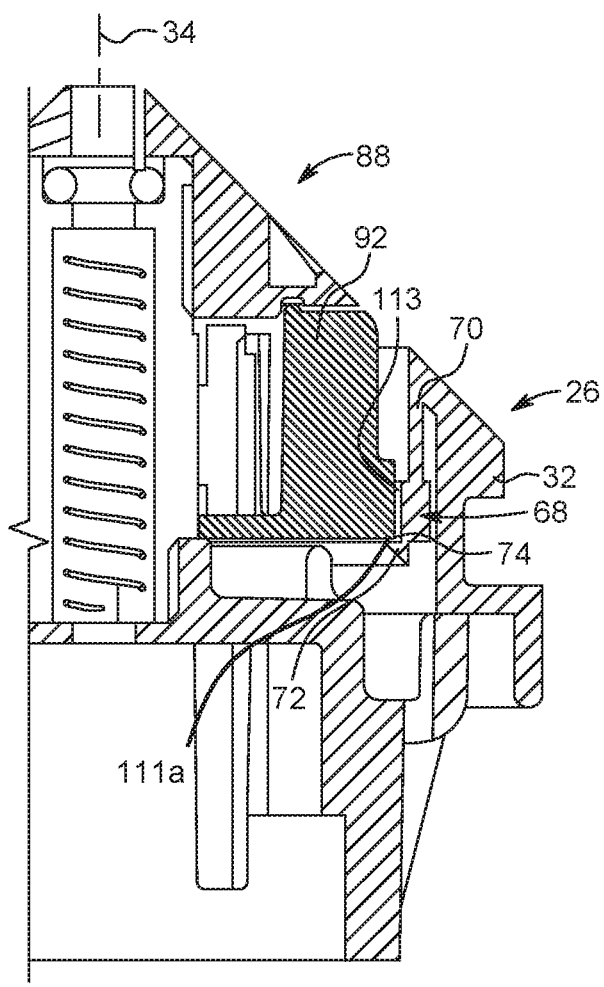
FIG. 23B is a first cross-sectional side view of the plunger illustrated in FIG. 23A showing the engagement between a piston and the plunger.

With reference to FIG. 23B, the second end 72 of the retaining member 68 has at least one catch 74 that is shaped to engage at least a portion of a recess, lip, or ledge on the piston to lock the at least one retaining member 68, along with the plunger 26, relative to the piston. In some aspects, the at least one catch 74 may protrude radially inward or outward relative to a body of the retaining member 68. The at least one catch 74 may be formed integrally with the second end 72 of the at least one retaining member 68 or it may be affixed or otherwise secured to the second end 72 of the at least one retaining member 68 using, for example, a frictional fit and/or an adhesive, welding, or by molding.

Figure 23C:
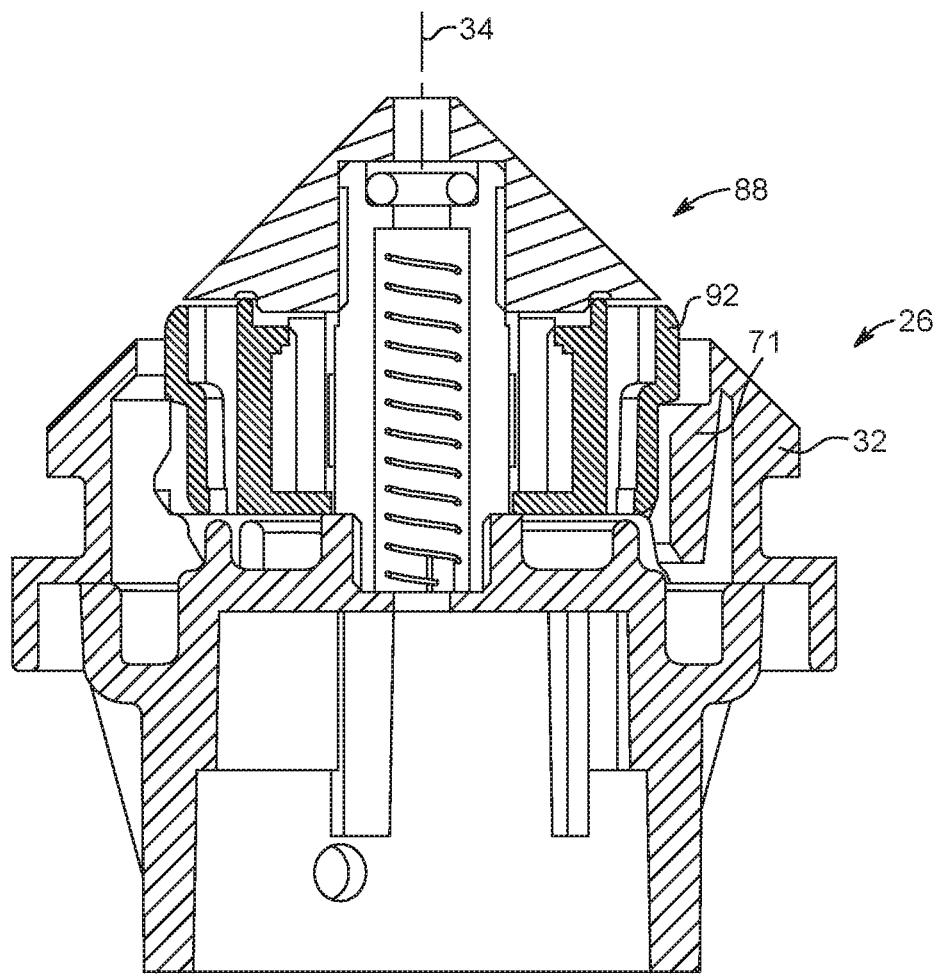
FIG. 23C is a second cross-sectional side view of the plunger illustrated in FIG. 23A showing the engagement between the piston and the plunger.
Figure 23D:
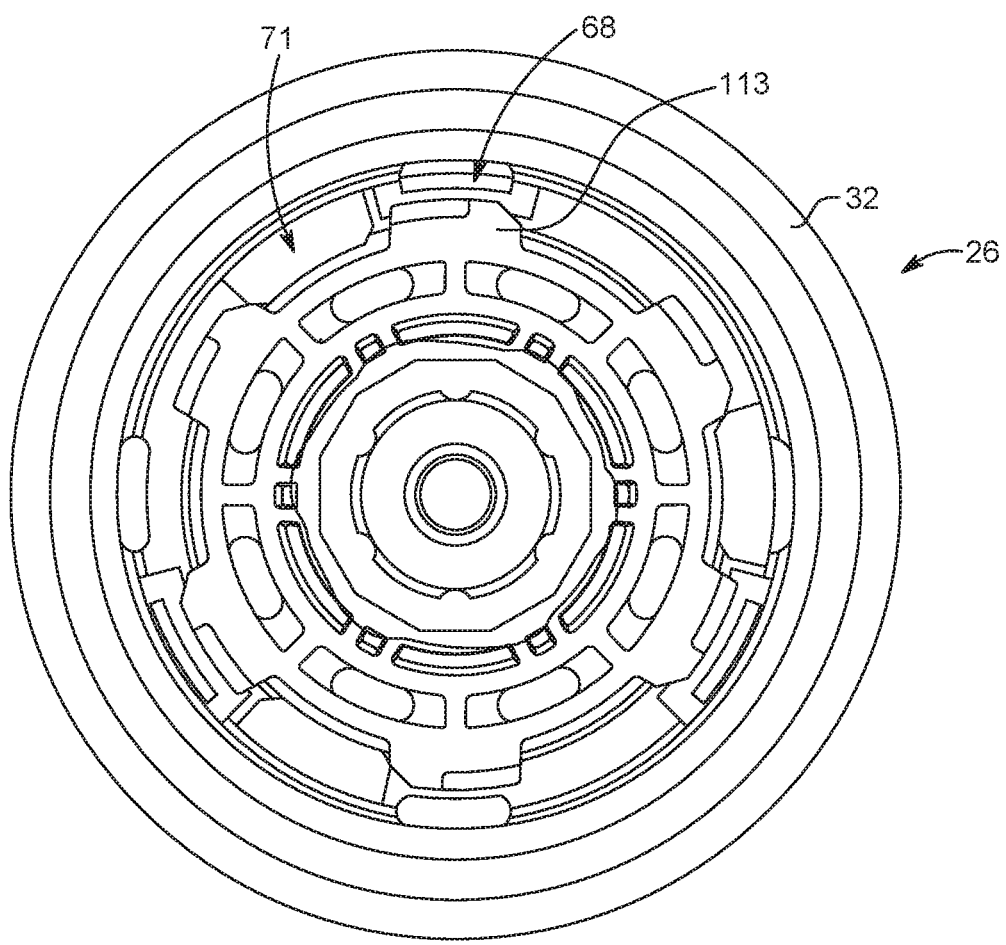
FIG. 23D is a cross-sectional top view of the plunger illustrated in FIG. 23A showing the engagement between a piston and the plunger.

With reference to FIG. 23C, the plunger 26 may have at least one first cam member 78 that interacts with a piston of the fluid injector 10 (shown in FIG. 1) to radially deflect the at least one retaining member 68 upon rotation of the plunger 26 relative to the piston, as described herein. The at least one first cam member 78 may be provided at the second end 72 of the retaining member 68. The at least one first cam member 78 may be angled at an angle B relative to the body of the retaining member 68.

The plunger 26 may have at least one alignment member, such as the at least one first alignment member 71 protruding from the plunger body 32. As described herein, the at least one first alignment member 71 is shaped and/or configured for facilitating self-orienting alignment of the plunger 26 with the piston 88. The at least one first alignment member 71 may be provided adjacent to the at least one retaining member 68.

To engage the plunger 26 with the piston 88, the syringe 12 is first inserted into the syringe port 16 of the fluid injector 10 (shown in FIG. 1), as described herein. If the piston 88 is rotationally misaligned relative to the plunger 26 such that the one or more alignment members 71 on the plunger 26 are not in rotational alignment to be received within the recesses 119 on the plunger head 92, the one or more alignment members 71 on the plunger 26 contact the guiding surface 117 of the second alignment member 113 on the piston head 92 to rotate the piston head 92 into alignment for connecting to the plunger 26. In this manner, the piston 88 self-orients itself relative to the plunger 26 such that the plunger 26 may be releasably locked with the piston 88. Distal movement of the piston 88 causes the retaining members 68 to deflect outward relative to the plunger longitudinal axis 34 from a first, undeflected position, to a second, radially deflected position. The piston 88 is advanced distally until the terminal portion of the second end 72 clears the retaining members 68, thereby allowing them to deflect radially inward toward or to their initial undeflected position. The catch 74 of at least one retaining member 68 is retained within the locking ledge 111 of the recess 119 or under a locking ledge 111a formed on a proximal end of the at least one second alignment member 113 on the piston head 92 (shown in FIG. 23B) to prevent disengagement of the plunger 26 from the piston head 92.

To unlock the syringe 12 from the syringe port 16 (shown in FIG. 1) and disengage the plunger 26 from the piston 88, the syringe 12 is rotated clockwise or counter-clockwise about the syringe longitudinal axis, in a clockwise or counter-clockwise direction, relative to the syringe port 16. Rotation of the syringe 12, and thereby the plunger 26, about the plunger longitudinal axis 34 engages the first cam member 78 on the plunger 26 with the second cam member 98 on the piston head 92. Such movement causes a deflection of the at least one retaining member 68 away from the piston head 92 to unlock the plunger 26 from the piston head 92 and allow the removal of the syringe 12 from the injector 10 (shown in FIG. 1).

Figure 24A:
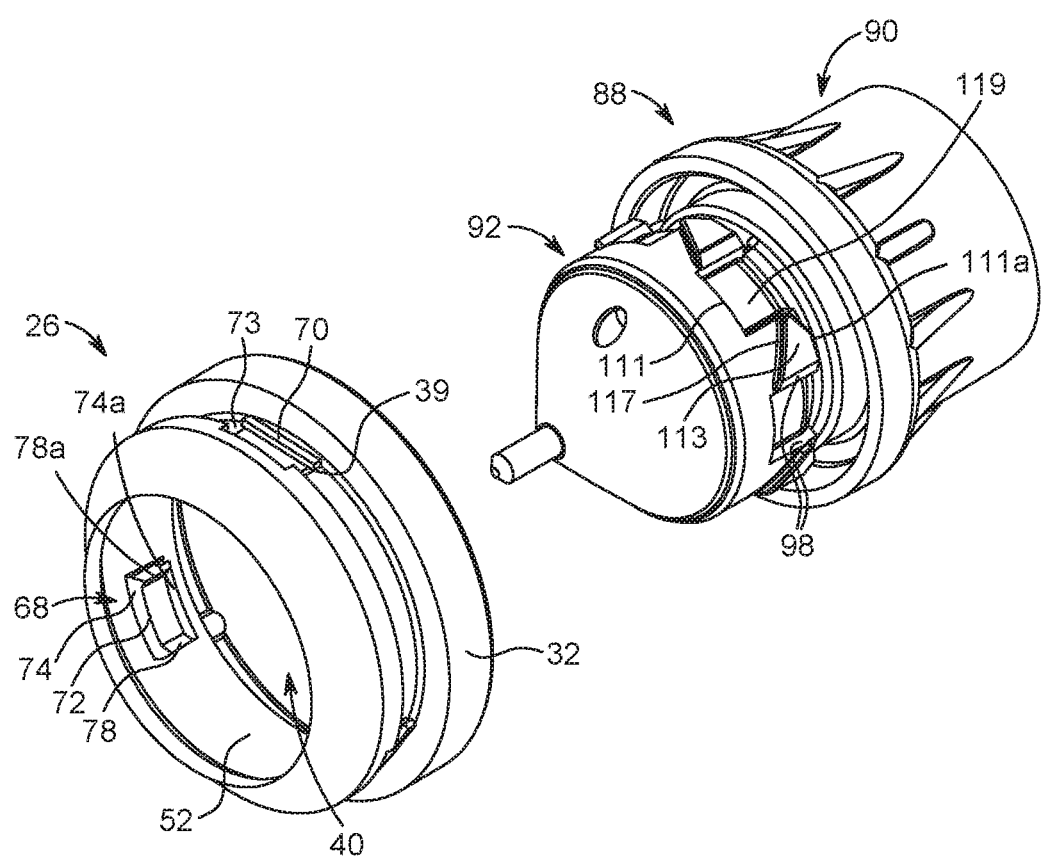
FIG. 24A is a top perspective view of a piston and a plunger in accordance with another aspect of the present disclosure.
Figure 24B:
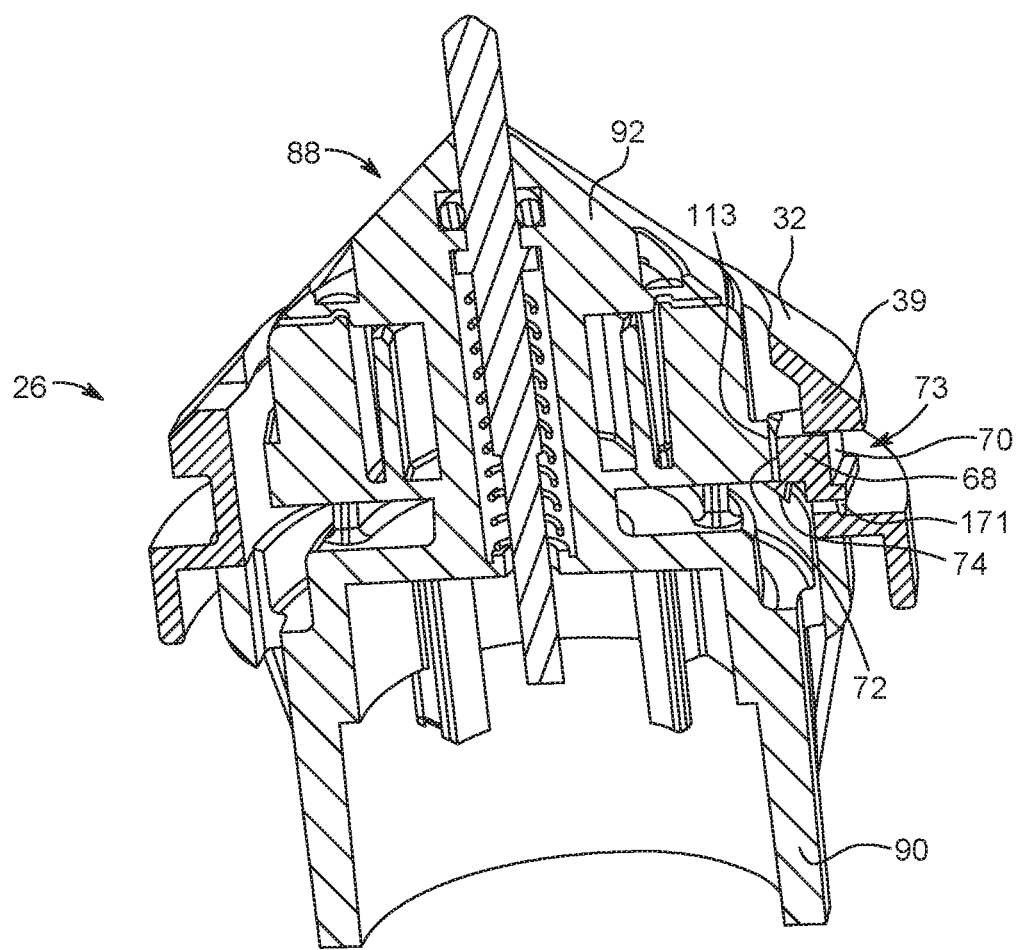
FIG. 24B is a side cross-sectional view of the piston and the plunger of FIG. 24A shown in an assembled state.
Figure 24C:
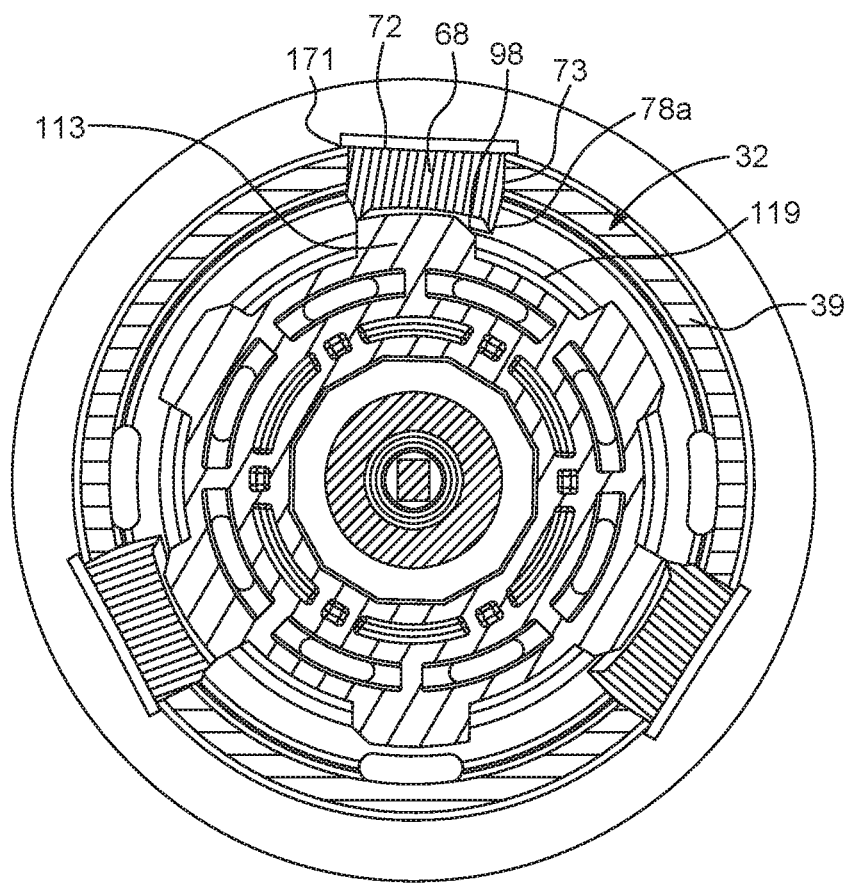
FIG. 24C is a top cross-sectional view of the piston and the plunger shown in FIG. 24B.

With reference to FIGS. 24A-24C, a plunger 26 and a piston 88 are shown in accordance with another aspect of the present disclosure. Some aspects of some of the components of the plunger 26 shown in FIGS. 24A-24C are substantially similar to the components of the plunger 26 described herein with reference to FIGS. 3A-4C. Other aspects of the components of the plunger 26 shown in FIGS. 24A-24C are substantially similar to the components of the plunger 26 described herein with reference to FIGS. 21A-21C. Similarly, the components of the piston 88 shown in FIGS. 24A-24C are substantially similar to the components of the piston 88 described herein with reference to FIGS. 21A-21C. Reference numerals in FIGS. 24A-24C are used to illustrate identical components of the corresponding reference numerals in FIGS. 4A-4C or FIGS. 21A-21C. As the previous discussion regarding the plunger 26 and piston 88 generally shown in FIGS. 3A-4C is applicable to the aspect of the present disclosure shown in FIGS. 24A-24C, only the relative differences between the plunger 26 and piston 88 generally shown in FIGS. 3A-4C and the plunger 26 and piston 88 generally shown in FIGS. 24A-24C are discussed hereinafter.

With reference to FIG. 24A, the plunger 26 may have at least one resiliently deflectable retaining member 68 (hereinafter "retaining member 68") associated with the plunger body 32. In some aspects, the at least one retaining member 68 may protrude in a radial direction from the inner surface 52 of the interior cavity 40. With continued reference to FIG. 24A, the at least one retaining member 68 has a first segment or a first end 70 extending through, towards, or into the outside to the plunger body 32. For example, the first end 70 of the at least one retaining member 68 may extend through an opening 73 extending through the sidewall 39 of the plunger body 32. The at least one retaining member 68 may have a second segment or a second end 72 extending radially inward to the interior cavity 40 relative to the first end 70. Features such as the at least one alignment members 71 are omitted for clarity.

The first end 70 of the at least one retaining member 68 may contact or abut, either directly or indirectly, a resilient member, for example the resilient inside surface of the plunger cover, such as the plunger cover 58 shown in FIG. 3E. Alternatively, or in addition, the first end 70 of the at least one retaining member 68 may contact or abut, either directly or indirectly, an elastic element, such as a metal or plastic spring, or other resilient material which urges the at least one retaining member 68 radially inward. With reference to FIG. 24B, the first end 70 of the at least one retaining member 68 may have at least one stop member 171 which limits the radially inward and/or outward travel of the at least one retaining member 68 so that it does not fall out of the plunger body 32. The stop member 171 may be the elastic element associated the at least one retaining member 68. The at least one retaining member 68 may be manufactured as a separate piece and inserted into the plunger body 32 before the plunger cover 58 is installed, co-molded with the plunger body 32 using a co-molding process, or may be molded as part of the plunger body 32 with a thin section (not shown) which deflects or breaks upon assembly or deflection of the at least one retaining member 68 in a radially inward or outward direction to allow the desired motion of the at least one retaining member 68. Optionally, the at least one resilient member 68 can have the stop member 171 or the thin section (not shown) which attaches the at least one retaining member 68 to the plunger body 32. In some aspects, a plurality of retaining members 68 may be spaced apart radially relative to the plunger longitudinal axis 34 along a circumference of the inner surface 52 of the interior cavity 40. The retaining members 68 may be separated from each other, such as by even or uneven spacing, by portions of the inner surface 52 of the interior cavity 40. The radial spacing of the at least one retaining member 68 relative to the plunger longitudinal axis 34 is selected to correspond to or operably interact with an outer shape of the piston, as described herein.

With reference to FIG. 24B, the second end 72 of the retaining member 68 has at least one catch 74 that is shaped to engage at least a portion of a recess, lip, or ledge on the piston to lock the at least one retaining member 68, along with the plunger 26, relative to the piston. In some aspects, the at least one catch 74 may protrude radially inward or outward relative to a body of the retaining member 68. The at least one catch 74 may be formed integrally with the second end 72 of the at least one retaining member 68 or it may be affixed or otherwise secured to the second end 72 of the at least one retaining member 68 using, for example, a frictional fit and/or an adhesive, welding, or by molding.

With reference to FIG. 24C, the plunger 26 may have at least one first cam member 78 that interacts with a piston of the fluid injector 10 (shown in FIG. 1) to radially deflect the at least one retaining member 68 upon rotation of the plunger 26 relative to the piston, as described herein. The at least one first cam member 78 may be provided at the second end 72 of the retaining member 68. The at least one first cam member 78 may be angled relative to the body of the retaining member 68.

The plunger 26 may have at least one alignment member, such as the first alignment member 71 shown in FIG. 3A or FIG. 23 protruding from the plunger body 32. As described herein, the at least one first alignment member 71 is shaped and/or configured for facilitating self-orienting alignment of the plunger 26 with the piston 88.

To engage the plunger 26 with the piston 88, the syringe 12 is first inserted into the syringe port 16 of the fluid injector 10 (shown in FIG. 1), as described herein. If the piston 88 is rotationally misaligned relative to the plunger 26 such that the one or more alignment members on the plunger 26 are not in rotational alignment to be received within the recesses 119 on the plunger head 92, the one or more alignment members on the plunger 26 contact the guiding surface 117 of the second alignment member 113 on the piston head 92 to rotate the piston head 92 into alignment for connecting to the plunger 26. In this manner, the piston 88 self-orients itself relative to the plunger 26 such that the plunger 26 may be releasably locked with the piston 88. Distal movement of the piston 88 causes the retaining members 68 to deflect outward relative to the plunger longitudinal axis 34 from a first, undeflected position, to a deflected position. The piston 88 is advanced distally until the terminal portion of the second end 72 clears the retaining members 68, thereby allowing them to deflect radially inward toward or to their initial undeflected position. The catch 74 of at least one retaining member 68 is retained within the locking ledge 111 of the recess 119 or the locking ledge 111a on a proximal surface of the second alignment members 113 to prevent disengagement of the plunger 26 from the piston head 92.

To unlock the syringe 12 from the syringe port 16 and disengage the plunger 26 from the piston 88, the syringe 12 is rotated clockwise or counter-clockwise about the syringe longitudinal axis, in a clockwise or counter-clockwise direction, relative to the syringe port 16. Rotation of the syringe 12, and thereby the plunger 26, about the plunger longitudinal axis 34 engages the first cam member 78 on the plunger 26 with the second cam member 98 on the piston head 92. Such movement causes a deflection of the at least one retaining member 68 radially away from the piston head 92 to unlock the plunger 26 from the piston head 92 and allow the removal of the syringe 12 from the injector 10 (shown in FIG. 1). In an alternative aspect, the catch 74a (shown in FIG. 24A) may be on the distal surface of the at least one retaining member 68 to engage within the locking ledge 111 shown in FIG. 24A to prevent disengagement of the plunger 26 from the piston head 92. The first cam member 78a may positioned as indicated in FIG. 24A to enable the catch 74a to be released upon relative rotation of the plunger 26 and the piston 88.

In accordance with various alternative aspects of the disclosure, the structural details of the connection interface between the plunger 26 and the piston 88 described herein could be reversed. That is, connection interfaces of any plunger 26 could comprise, for example, the locking mechanism and corresponding features described herein with reference to any piston 88, while the connection interface on the piston 88 could comprise, for example, the elements described herein as being part of the plunger 26.

Although the disclosure has been described in detail for the purpose of illustration based on what are currently considered to be the most practical and preferred aspects, it is to be understood that such detail is solely for that purpose and that the disclosure is not limited to the disclosed aspects, but, on the contrary, is intended to cover modifications and equivalent arrangements. For example, it is to be understood that the present disclosure contemplates that, to the extent possible, one or more features of any aspect can be combined with one or more features of any other aspect.

We claim:

1. A plunger for use with a syringe, the plunger comprising:
    a plunger body having a proximal end, a distal end, and a sidewall extending from the proximal end to the distal end along a plunger longitudinal axis, wherein the plunger body comprises a conical-shaped portion at the distal end of the plunger body and at least a portion having a circular cross-section at the proximal end of the plunger body;
    at least one resiliently deflectable retaining member having a first segment attached to an inner surface of the plunger body and a second segment protruding from the first segment toward the distal end of the plunger body and wherein the second segment is radially deflectable relative to the plunger longitudinal axis; and
    at least one actuation member associated with the at least one resiliently deflectable retaining member, wherein the at least one actuation member is angled relative to a plane defined by a body of the at least one resiliently deflectable retaining member and radially deflects the at least one resiliently deflectable retaining member in response to an actuation force.

2. The plunger of claim 1, further comprising at least one alignment member associated with a second portion of the inner surface of the plunger body, wherein the at least one alignment member has at least one alignment surface for guiding the plunger body into self-orienting alignment with a piston of a fluid injector.

3. The plunger of claim 2, wherein the at least one alignment member comprises a plurality of alignment members spaced apart around a circumference of the second portion of the inner surface the plunger body.

4. The plunger of claim 3, wherein the plurality of alignment members are spaced apart at equal radial intervals around the circumference of the second portion of the inner surface of the plunger body.

5. The plunger of claim 1, wherein the second segment of the at least one resiliently deflectable retaining member is angled toward the plunger longitudinal axis and radially deflectable relative to the first segment away from the plunger longitudinal axis.

6. The plunger of claim 1, wherein the at least one resiliently deflectable retaining member is linearly or curvilinearly contiguous between the first segment and the second segment.

7. The plunger of claim 1, wherein the conical-shaped portion of the plunger body comprises one or more radial openings arranged around the conical-shaped portion.

8. The plunger of claim 1, wherein the at least one actuation member is provided on a surface of the at least one resiliently deflectable retaining member.

9. The plunger of claim 1, wherein the at least one resiliently deflectable retaining member comprises a plurality of resiliently deflectable retaining members spaced apart around the plunger longitudinal axis.

10. The plunger of claim 1, wherein a catch surface at a terminal end of the second segment of the at least one resiliently deflectable retaining member engages a surface of a corresponding locking ledge of a piston of a fluid injector to releasably lock the plunger with the piston.

11. The plunger of claim 10, wherein the catch surface is perpendicular or angled relative to a direction of the plunger longitudinal axis.

12. The plunger of claim 1, further comprising a plunger cover disposed over at least a portion of an outer surface of the plunger body, wherein the plunger cover comprises a resilient seal disposed around at least a portion of a circumferential sidewall of the plunger body.

13. A plunger body for engaging a plunger with an injector piston, the plunger body comprising:
    a proximal end;
    a distal end;
    a sidewall extending from the proximal end to the distal end along a plunger body longitudinal axis, wherein the plunger body comprises a conical-shaped portion at the distal end and at least a portion having a circular cross-section at the proximal end;
    at least one resiliently deflectable retaining member having a first segment attached to an inner surface of the plunger body and a second segment protruding from the first segment toward the distal end, wherein the second segment is radially deflectable relative to the plunger body longitudinal axis; and
    at least one actuation member associated with the at least one resiliently deflectable retaining member, wherein the at least one actuation member is angled relative to a plane defined by a body of the at least one resiliently deflectable retaining member and radially deflects the at least one resiliently deflectable retaining member in response to an actuation force.

14. The plunger body of claim 13, further comprising at least one alignment member associated with a second portion of the inner surface of the plunger body, wherein the at least one alignment member has at least one alignment surface for guiding the plunger body into self-orienting alignment with a piston of a fluid injector.

15. The plunger body of claim 14, wherein the at least one alignment member comprises a plurality of alignment members spaced apart around a circumference of the second portion of the inner surface of the plunger body.

16. The plunger body of claim 13, wherein the second segment of the at least one resiliently deflectable retaining member is angled toward the plunger body longitudinal axis and radially deflectable relative to the first segment away from the plunger body longitudinal axis.

17. The plunger body of claim 13, wherein the at least one resiliently deflectable retaining member comprises a plurality of resiliently deflectable retaining members spaced apart around the plunger body longitudinal axis.

18. The plunger body of claim 13, wherein the conical-shaped portion of the plunger body comprises one or more radial openings arranged around the conical-shaped portion.

19. A plunger body for engaging a plunger with an injector piston, the plunger body comprising:
- a proximal end;
- a distal end;
- a sidewall extending from the proximal end to the distal end along a plunger body longitudinal axis, wherein the plunger body comprises a conical-shaped portion at the distal end and at least a portion having a circular cross-section at the proximal end;
- a plurality of resiliently deflectable retaining members, each having a first segment attached to an inner surface of the plunger body and a second segment protruding from the first segment toward the distal end, wherein the second segment is angled toward the plunger body longitudinal axis and radially deflectable relative to the first segment away from the plunger body longitudinal axis;
- a plurality of actuation members associated with the plurality of resiliently deflectable retaining members, wherein an actuation member radially deflects a resiliently deflectable retaining member in response to an actuation force; and
- a plurality of alignment members associated with a second portion of the inner surface of the plunger body, the plurality of alignment members each having at least one alignment surface for guiding the plunger body into self-orienting alignment with a piston of an fluid injector,
- wherein the conical-shaped portion of the plunger body comprises one or more radial openings arranged around the conical-shaped portion.

* * * * *

UNITED STATES PATENT AND TRADEMARK OFFICE
CERTIFICATE OF CORRECTION

PATENT NO. : 10,512,721 B2
APPLICATION NO. : 15/334644
DATED : December 24, 2019
INVENTOR(S) : Swantner et al.

It is certified that error appears in the above-identified patent and that said Letters Patent is hereby corrected as shown below:

In the Specification

In Column 30, Lines 12-13, delete "in the groove 1030 of the second cam member" and insert -- in the groove of the second cam member -- therefor.

In Column 30, Lines 53-54, delete "of the grooves 101 of the second cam member" and insert -- of the grooves of the second cam member -- therefor.

Signed and Sealed this
Third Day of March, 2020

Andrei Iancu
*Director of the United States Patent and Trademark Office*